US011260120B2

(12) United States Patent
Aman et al.

(10) Patent No.: US 11,260,120 B2
(45) Date of Patent: Mar. 1, 2022

(54) IMMUNOGENIC COMPOSITION COMPRISING A FUSION PEPTIDE DERIVED FROM SUPERANTIGEN TOXOIDS

(71) Applicant: INTEGRATED BIOTHERAPEUTIC VACCINES, INC., Rockville, MD (US)

(72) Inventors: Mohammad Javad Aman, Rockville, MD (US); Thomas Kort, Rockville, MD (US); Arundhathi Venkatasubramaniam, Rockville, MD (US); Nils Williston, Rockville, MD (US); Rajan Prasad Adhikari, Rockville, MD (US); Frederick W. Holtsberg, Rockville, MD (US)

(73) Assignee: INTEGRATED BIOTHERAPEUTIC VACCINES, INC., Rockville, MD (US)

( * ) Notice: Subject to any disclaimer, the term of this patent is extended or adjusted under 35 U.S.C. 154(b) by 0 days.

(21) Appl. No.: 16/633,664

(22) PCT Filed: Jul. 25, 2018

(86) PCT No.: PCT/US2018/043687
§ 371 (c)(1),
(2) Date: Jan. 24, 2020

(87) PCT Pub. No.: WO2019/023341
PCT Pub. Date: Jan. 31, 2019

(65) Prior Publication Data
US 2020/0206335 A1 Jul. 2, 2020

Related U.S. Application Data

(60) Provisional application No. 62/537,706, filed on Jul. 27, 2017.

(51) Int. Cl.
*A61K 39/085* (2006.01)
*A61P 31/04* (2006.01)
*C12N 15/70* (2006.01)
*A61K 39/00* (2006.01)

(52) U.S. Cl.
CPC .......... *A61K 39/085* (2013.01); *A61P 31/04* (2018.01); *C12N 15/70* (2013.01); *A61K 2039/53* (2013.01); *A61K 2039/55505* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 6,399,332 B1 | 6/2002 | Ulrich et al. | |
| 6,713,284 B2 | 3/2004 | Ulrich et al. | |
| 7,087,235 B2 | 8/2006 | Ulrich | |
| 7,226,595 B2 | 6/2007 | Antonsson et al. | |
| 7,378,257 B2 | 5/2008 | Ulrich et al. | |
| 7,750,132 B2 | 7/2010 | Ulrich | |
| 7,754,225 B2 | 7/2010 | Fattom et al. | |
| 8,067,202 B2 | 11/2011 | Ulrich et al. | |
| 9,815,872 B2 | 11/2017 | Aman et al. | |
| 2003/0009015 A1 | 1/2003 | Ulrich et al. | |
| 2004/0043037 A1 | 3/2004 | Kunsch et al. | |
| 2007/0087014 A1 | 4/2007 | Pavliak et al. | |
| 2010/0111978 A1 | 5/2010 | Forsberg et al. | |
| 2010/0119477 A1 | 5/2010 | Otto et al. | |
| 2011/0027265 A1 | 2/2011 | Bubeck-Wardenburg et al. | |
| 2016/0185829 A1 | 6/2016 | Aman et al. | |

FOREIGN PATENT DOCUMENTS

| | | |
|---|---|---|
| EP | 2011877 A2 | 1/2009 |
| JP | 2002502363 A | 1/2002 |
| JP | 2005524381 A | 8/2005 |
| WO | 1997/36932 A1 | 10/1997 |
| WO | 00/02523 A2 | 1/2000 |
| WO | 2003/012111 A2 | 2/2003 |
| WO | 2003056015 A1 | 7/2003 |
| WO | 2012/109167 A1 | 8/2012 |
| WO | 2012170097 A2 | 12/2012 |
| WO | 2013/082558 A1 | 6/2013 |
| WO | 2014/205111 A1 | 12/2014 |

OTHER PUBLICATIONS

Cruse et al., Illustrated Dict. of Immunology, 2nd ed., CRC Press, 2003.*
McGuinness et al. (Mol. Microbiol., 7:505-514, 1993).*
Moudallal et al. (EMBO Journal, 1:1005-1010, 1982).*
Abaza et al. (J. Prot. Chem., 11:433-444, 1992).*
McElroy, et al., "Alpha-toxin damages the air-blood barrier of the lung in a rat model of *Staphylococcus aureus*-induced pneumonia," 1999, Infect Immun, 67 (10):5541-5544.
McKenney D. et al., "Broadly Protective Vaccine for *Staphylococcus aureus* Based on an in Vivo-Expressed Antigen," Science, 284(5419):1523-1527, May 28, 1999.
McKenney D. et al., "Vaccine potential of poly-1-6 beta-D-N-succinylglucosamine, an immunoprotective surface polysaccharide of *Staphylococcus aureus* and *Staphylococcus epidermidis*," J. Biotechnol. Sep. 29, 2000;83(1-2):37-44.
Menzies and Kemodle, "Passive immunization with antiserum to a nontoxic alpha-toxin mutant from *Staphylococcus aureus* is protective in a murine model," 1996; Infect Immun, 64 (5):1839-1841.

(Continued)

*Primary Examiner* — Brian Gangle
(74) *Attorney, Agent, or Firm* — Thompson Coburn LLP; William A. Holtz

(57) ABSTRACT

The present disclosure provides immunogenic compositions useful in prevention and treatment of *Staphylococcus aureus* infection. In particular, the disclosure provides multivalent oligopeptides, fusion proteins comprising two or more staphylococcal superantigen (SAg) proteins, or any fragments, variants, or derivatives thereof fused together as a single polypeptide in any order.

44 Claims, 7 Drawing Sheets

Figure 2:
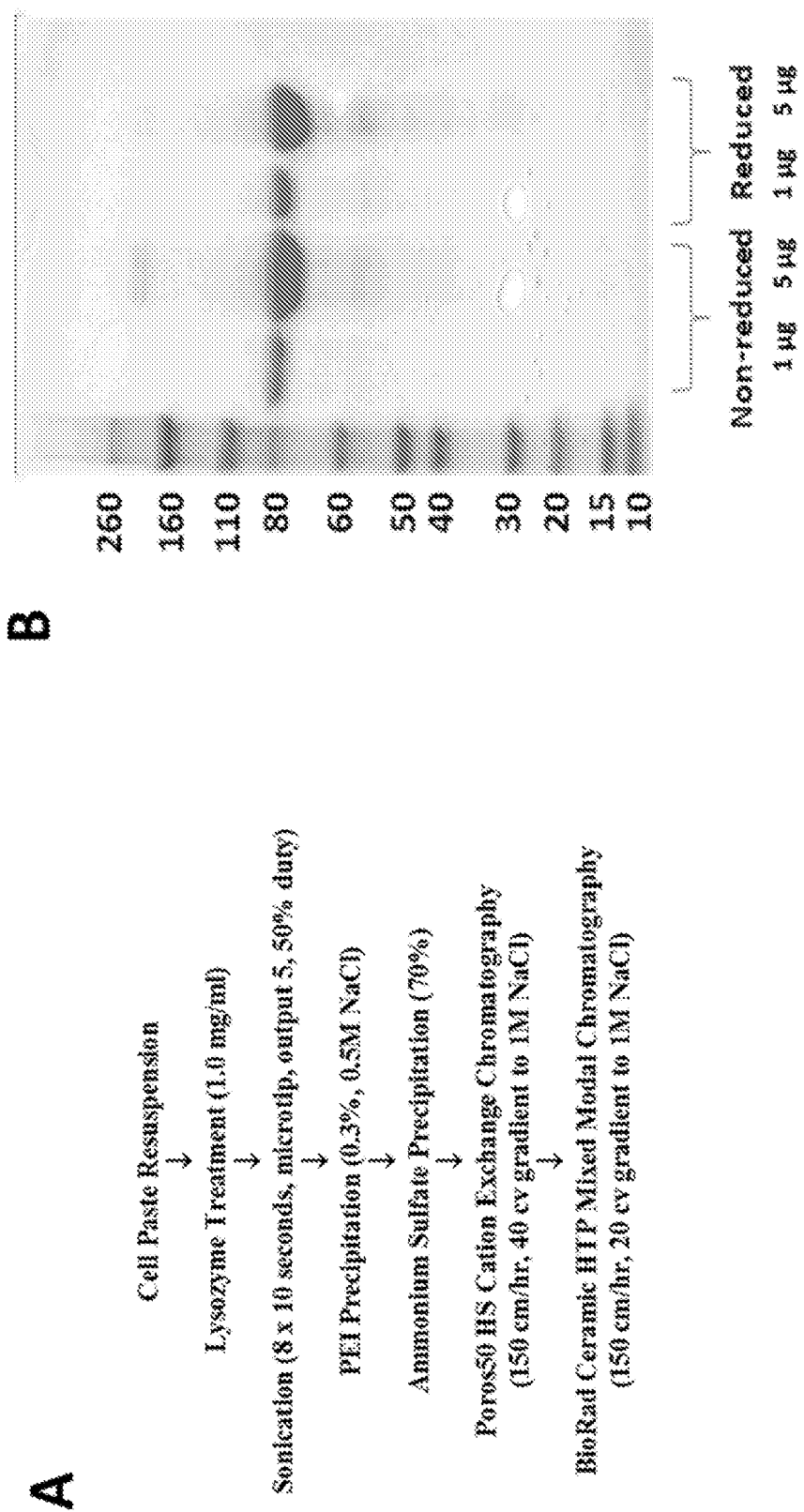

Specification includes a Sequence Listing.

(56) References Cited

OTHER PUBLICATIONS

Miles et al., "Subunit Composition of a Bicomponent Toxin: Staphylococcal Leukocidin Forms an Octameric Transmembrane Pore", Protein Science, 2002, pp. 894-902, vol. 11.
Neuhaus, F.C. and J. Baddiley, "A continuum of anionic charge: structures and functions of D-alanyl-teichoic acids in gram-positive bacteria," Microbiol Mol Biol Rev, 67(4):686-723(2003).
Novick et al., Synthesis of staphylococcal virulence factors is controlled by a regulatory RNA molecule EMBO Journal 12(10):3967-3975 (1993).
Novick, "Autoinduction and signal transduction in the regulation of staphylococcal virulence," Mol Microbiol 48 (6) 1429-1449 (2003).
O'Riordan and Lee, "*Staphylococcus aureus* Capsular Polysaccharides," Clinical Microbiology Reviews, Jan. 2004, p. 218-234, vol. 17, No. 1.
Office Action for U.S. Appl. No. 14/899,993 dated Feb. 15, 2017.
Office Action for U.S. Appl. No. 15/810,419 dated Apr. 3, 2018.
Omae et al., "Inhibition of Colony-spreading Activity of *Staphylococcus aureus* by Secretion of Delta-Hemolysin," J Biol Chem, 287 (19):15570-15579 (2012).
Omoe et al., "Detection of seg, seh, and sei genes in *Staphylococcus aureus* Isolates and Determination of the Enterotoxin Productivities of *S. aureus* Isolates Harboring seg, seh, or sei Genes," (2002) J Clin Microbiol 40 (3):857-862.
Periasamy et al., "How *Staphylococcus aureus* biofilms develop their characteristic structure," Proc Natl Acad Sci 109 (4):1281-1286 (2012).
Poutrel and Sutra, "Type 5 and 8 capsular polysaccharides are expressed by *Staphylococcus aureus* isolates from rabbits, poultry, pigs, and horses," J Clin Microbiol. Feb. 1993;31(2):467-469.
Reddy et al., "A Simple and Universal Ligation Mediated Fusion of Genes Based on Hetero-Staggered PCR for Generating Immunodominant Chimeric Proteins", Gene, Aug. 16, 2012, pp. 104-109, vol. 509.
Salgado-Pabon et al., "*Staphylococcus aureus* Beta-toxin Production is Common in Strains With the Beta-toxin Gene Inactivated by Bacteriophage", Journal of Infectious Diseases, 2014, pp. 784-792, vol. 210 No. 5.
Schmitz et al., Delta-Toxin from *Staphylococcus aureus* as a Costimulator of Human Neutrophil Oxidative Burst (1997) J Infect Dis 176 (6):1531-1537.
Shinefield H et al., "Use of a *Staphylococcus aureus* conjugate vaccine in patients receiving hemodialysis," N Engl J Med. Feb. 14, 2002;346(7):491-6.
Shukla, et al., "Virulence genes and genotypic associations in nasal carriage, community-associated methicillin-susceptible and methicillin-resistant USA400 *Staphylococcus aureus* isolates," 2010, J Clin Microbiol, 48 (10):3582-3592.
Shylaja et al., "Application of a Chimeric Protein Construct Having Enterotoxin B and Toxic Shock Syndrome Toxin Domains of *S. aureus* in Immunodiagnostics", Indian Journal of Microbiology, Jul.-Sep. 2012, pp. 449-455, vol. 52, No. 3.
Spaulding et al., "Immunity to *Staphylococcus aureus* Secreted Proteins Protects Rabbits from Serious Illnesses", Vaccine, Jul. 20, 2012, pp. 5099-5109, vol. 30, No. 34.
Thakker, M., et al., "*Staphylococcus aureus* serotype 5 capsular polysaccharide is antiphagocytic and enhances bacterial virulence in a murine bacteremia model," Infect Immun, 1998 66(11):5183-5189.
Thiaudiere et al., "The Amphiphilic Alpha-Helix Concept. Consequences on the Structure of Staphylococcal Delta-Toxin in Solution and Bound to Lipids", European Journal of Biochemistry, Jan. 1, 1991, pp. 203-213, vol. 195 No. 1.
Todd et al., Toxic-shock syndrome associated with phage-group-I *Staphylococci*, Lancet 2, (8100):1116-1118 (1978).
Tollersrud et al., "Genetic and Serologic Evaluation of Capsule Production by Bovine Mammary Isolates of *Staphylococcus aureus* and Other *Staphylococcus* spp. from Europe and the United States," J Clin Microbiol. Aug. 2000;38(8):2998-3003.

Tuchscherr LP. et al., "Antibodies to capsular polysaccharide and clumping factor A prevent mastitis and the emergence of unencapsulated and small-colony variants of *Staphylococcus aureus* in mice," Infect Immun. Dec. 2008;76(12):5738-44.
Ulrich, et al., Development of engineered vaccines effective against structurally related bacterial superantigens, 1998, Vaccine, 16 (19):1857-1864.
Verghese A. et al., "LY146032 in a Hamster Model of *Staphylococcus aureus* Pneumonia—Effect on in vivo Clearance and Mortality and in vitro Opsonophagocytic Killing," Chemotherapy. 34:497-503 (1988).
Wang et al., "Identification of novel cytolytic peptides as key virulence determinants for community-associated MRSA," Nat. Med. Dec. 2007; 13(12):1510-1514, Epub Nov. 11, 2007.
Wang et al., "*Staphylococcus epidermidis* surfactant peptides promote biofilm maturation and dissemination of biofilm-associated infection in mice," J Clin Invest. 2011; 121(1):238-248.
Wu and Park, "Chemical Characterization of a New Surface Antigenic Polysaccharide from a Mutant of *Staphylococcus aureus*," 1971. J. Bacterial. 108(2):874-884.
Yang, Z. et al., "Overcoming Immunity to a Viral Vaccine by DNA Priming before Vector Boosting," J Virol. 77 (1):799-803, 2003.
A Fattom et al., "A *Staphylococcus aureus* capsular polysaccharide (CP) vaccine and CP-specific antibodies protect mice against bacterial challenge," Infect Immun. May 1996; 64(5): 1659-1665.
A Fattom et al., "Laboratory and clinical evaluation of conjugate vaccines composed of *Staphylococcus aureus* type 5 and type 8 capsular polysaccharides bound to Pseudomonas aeruginosa recombinant exoprotein A," Infect Immun. Mar. 1993; 61(3): 1023-1032.
Aarestrup, et al., "Frequency of alpha- and beta-haemolysin in *Staphylococcus aureus* of bovine and human origin—A comparison between pheno- and genotype and variation in phenotypic expression," 1999, APMIS, 107 (4):425-430.
Abrahmsen et al., "Characterization of Two Distinct MHC Class II Binding Sites in the Superantigen Staphylococcal Enterotoxin A", The EMBO Journal, Jul. 3, 1995, vol. 14, No. 13, pp. 2978-2986.
Adhikari et al., "Lower Antibody Levels to *Staphylococcus aureus* Exotoxins Are Associated With Sepsis in Hospitalized Adults With Invasive *S. aureus* Infections," J Infec Dis, 206 (6):915-923 (2012).
Adhikari, et al., "Novel structurally designed vaccine for *S. aureus* alpha-hemolysin: protection against bacteremia and pneumonia," 2012, PLoS One, 7 (6): e38567.
Bavari and Ulrich, Staphylococcal enterotoxin A and toxic shock syndrome toxin compete with CD4 for human major histocompatibility complex class II binding, Infect Immun, 63 (2):423-429 (1995).
Bavari, et al., Superantigen vaccines: a comparative study of genetically attenuated receptor-binding mutants of staphylococcal enterotoxin A, 1996, J Infect Dis, 174:338-345.
Bhakdi and Tranum-Jensen, "Alpha-toxin of *Staphylococcus aureus*," 1991, Microbiol Rev, 55 (4):733-751.
Bohach et al., "Staphylococcal and streptococcal pyrogenic toxins involved in toxic shock syndrome and related illnesses,"(1990) Crit Rev Microbiol, 12(4):251-272.
Boles, et al., Correlation of body temperature with protection against staphylococcal enterotoxin B exposure and use in determining vaccine dose-schedule, 2003, Vaccine, 21 (21-22):2791-2796.
Boles, et al.. Generation of protective immunity by inactivated recombinant staphylococcal enterotoxin B vaccine in nonhuman primates and identification of correlates of immunity 2003 Clin Immunol, 108 (1):51-59.
Brown and Pattee, "Identification of a chromosomal determinant of alpha-toxin production in *Staphylococcus aureus*," 1980, Infect Immun, 30 (1):36-42.
Bubeck Wardenburg and Schneewind, Vaccine protection against *Staphylococcus aureus* pneumonia J Exp Med, 205 (2):287-294 (2008).
Bubeck-Wardenburg J. et al., "Surface Proteins and Exotoxins Are Required for the Pathogenesis of *Staphylococcus aureus* Pneumonia," Infect Immun. vol. 75(2):1040-4 (2007).
Chatterjee et al., "Distribution and Regulation of the Mobile Genetic Element-Encoded Phenol-Soluble Modulin PSM-mec in Methicillin-Resistant *Staphylococcus aureus*," PLoS One, 6 (12):e28781 (2011).

(56) References Cited

OTHER PUBLICATIONS

Cheung et al., "Direct and synergistic hemolysis caused by *Staphylococcus* phenol-soluble modulins: implications for diagnosis and pathogenesis," Microbes Infect 14 (4):380-386 (2012).
Cheung et al., "Staphylococcus Epidermidis Strategies to Avoid Killing by Human Neutrophils", PLoS Pathogens, Oct. 7, 2010, pp. e1001133, vol. 6 No. 10.
Choi, et al., "Interaction of *Staphylococcus aureus* toxin "superantigens" with human T cells," 1989, Proc Natl Acad Sci U S A, 86 (22):8941-8945.
Cunnion KM et al., "Capsule production and growth phase influence binding of complement to *Staphylococcus aureus*," Infect Immun. Nov. 2001;69(11):6796-803.
Database Accession No. A7WKH1 dated Oct. 23, 2007, Putative Uncharacterized Protein, XP-002765826.
Database Accession No. B6K4A7 dated Dec. 16, 2008, snRNP-Associated Protein Lsm3, XP-002765832.
Database Accession No. B9MYD5 dated Mar. 24, 2009, Uncharacterized Protein, XP-002765831.
Database Accession No. C2CFF8 dated Jun. 16, 2009, LemA Family Protein, XP-002765827.
Database Accession No. E9G462 dated Apr. 5, 2011, Putative Uncharacterized Protein, XP-002765828.
Database Accession No. G1VLX9 dated Nov. 16, 2011, Uncharacterized Protein, XP-002765830.
Database Accession No. J4VWK9 dated Oct. 31, 2012, Tail Tape Measure Protein, XP-002765829.
Diep and Otto, "The role of virulence determinants in community-associated MRSA pathogenesis," Trends Microbiol, 16 (8):361-369 (2008).
Enkhbaatar P. et al., "Novel Ovine Model of Methicillin-Resistant *Staphylococcus aureus*-Induced Pneumonia and Sepsis," Shock 29(5):642-49 (2008).
Fattom Ali et al., "Development of StaphVAX TM, a polysaccharide conjugate vaccine against *S. aureus* infection: from the lab bench to phase III clinical trials," Vaccine. Feb. 17, 2004;22(7):880-7.
Fournier et al., Isolation of Type 5 Capsular Polysaccharide From the *Staphylococcus aureus*, Ann. Inst. Pasteur/Microbiol., vol. 138, pp. 561-567 (1987).
Fournier, J. M., et al., "Purification and characterization of *Staphylococcus aureus* type 8 capsular polysaccharide," Infect. Immun. 45(1):87-93 (1984).
Gautier, et al., "HELIQUEST: a web server to screen sequences with specific a-helical properties," 2008, Bioinformatics, 24 (18):2101-2102.
Giese et al., "Expression of delta-toxin by *Staphylococcus aureus* mediates escape from phago-endosomes of human epithelial and endothelial cells in the presence of beta-toxin," Cell Microbiol 13 (2):316-329 (2011).
Hudson et al., "Staphylococcal Enterotoxin A Has Two Cooperative Binding Sites on Major Histocompatibility Complex Class II", Journal of Experimental Medicine, Sep. 1, 1995, vol. 182, No. 3, pp. 711-720.
Husmann, et al., "Elimination of a bacterial pore-forming toxin by sequential endocytosis and exocytosis," 2009, FEBS Lett, 583 (2):337-344.
International Preliminary Report on Patentability (Chapter I) for PCT/US2014/042999 dated Dec. 30, 2015.
International Search Report and Written Opinion for PCT/US2014/042999 dated Oct. 23, 2014.
International Search Report and Written Opinion for PCT/US2018/043687 dated Oct. 15, 2018.
Johns and Khan, "Staphylococcal enterotoxin B gene is associated with a discrete genetic element," 1988, J Bacteriol, 170 (9):4033-4039.
Kaito et al., "Transcription and Translation Products of the Cytolysin Gene psm-mec on the Mobile Genetic Element SCCmec Regulate *Staphylococcus aureus* Virulence," PLoS Pathog, 7 (2):e1001267 (2011).
Karauzum, et al., Structurally Designed Attenuated Subunit Vaccines for *S. aureus* LukS-PV and LukF-PV Confer Protection in a Mouse Bacteremia Model2013, PLoS ONE, 8 (6):e65384.
Kennedy et al., "Targeting of Alpha-Hemolysin by Active or Passive Immunization Decreases Severity of USA300 Skin Infection in a Mouse Model," J Infect Dis 202, (7):1050-1058 (2010).
Kephart, et al. "Comparison of the Investigational drug, LY146032, with vancomycin in experimental pneumonia due to methicillin-resistant *Staphylococcus aureus*," J Antimicrob Chemother. 21:33-9, (1988).
Kozono et al., "Multiple Binding Sites for Bacterial Superantigens on Soluble Class II MHC Molecules", Immunity, Aug. 1995, pp. 187-196, vol. 3.
Kreger et al., "Purification and Properties of Staphylococcal Delta Hemolysin," Infect Immun 3 (3):449-465 (1971).
Krupka et al., "Structural Basis for Abrogated Binding Between Staphylococcal Enterotoxin A Superantigen Vaccine and MHC-lla", Protein Science, Mar. 31, 2002, vol. 11, No. 3, pp. 642-651.
Lee et al., "Protective efficacy of antibodies to the *Staphylococcus aureus* type 5 capsular polysaccharide in a modified model of endocarditis in rats," Infect Immun. Oct. 1997; 65(10): 4146-4151.
Maira-Litran T et al., "Comparative Opsonic and Protective Activities of *Staphylococcus aureus* Conjugate Vaccines Containing Native or Deacetylated Staphylococcal Poly-N-Acetyl-P-(1-6)-Glucosamine," Infect Immun. Oct. 2005;73 (10):6752-62.
Marrack et al., "The Staphylococcal Enterotoxins and Their Relatives," Science, vol. 248, No. 1, (1990).
Extended European Search Report for European Application No. 18838475.4 dated May 17, 2021.
Tiedemann et al., "Cross-Linking of MHC Class II Molecules by Staphylococcal Enterotoxin A is Essential for Antigen-Presenting Cell and T Cell Activation", The Journal of Immunology, 1996, vol. 157, pp. 3958-3966.
Venkatasubramaniam et al., "TBA225, a Fusion Toxoid Vaccine for Protection and Broad Neutralization of Staphylococcal Superantigens", Scientific Reports, 2019, pp. 1-13, vol. 9, No. 3279.
Office Action for Canadian Application 2916231 dated Jul. 7, 2021.

* cited by examiner

Figure 1

IMMUNOGENIC COMPOSITION COMPRISING A FUSION PEPTIDE DERIVED FROM SUPERANTIGEN TOXOIDS

CROSS-REFERENCE TO RELATED APPLICATIONS

This application is a U.S. National Phase application of PCT/US2018/043687, filed on Jul. 25, 2018, which claims the benefit of U.S. Provisional Application No. 62/537,706, filed Jul. 27, 2017, both of which are incorporated herein by reference in their entirety.

This application is related to U.S. patent application Ser. No. 14/899,993, filed Dec. 18, 2015, now U.S. Pat. No. 9,815,872, which is incorporated by reference herein in its entirety.

GOVERNMENT RIGHTS

This invention was made with Government support under AI111205 awarded by the National Institutes of Health. The Government has certain rights in the invention.

INCORPORATION OF SEQUENCE LISTING

A sequence listing containing the file named "IBV_193252_Substitute_SeqList_ST25.txt", which is 35,037 bytes (measured in MS-Windows®), contains 12 sequences, and was created on Apr. 20, 2021, is provided herewith and is incorporated herein by reference in its entirety.

BACKGROUND

*Staphylococcus aureus* (SA) is a gram-positive human pathogen that causes a wide range of infections from skin and soft tissue infections (SST1) to life threatening sepsis and pneumonia. It is a leading cause of hospital- and community-associated infections worldwide (Brown et al., 2009, Journal/Clin Microbiol Infect, 15(2): 156-164). The range of pathologies reflects the diverse abilities of SA to escape the immune response using a plethora of virulence factors: the superantigenic and pore-forming toxins, coagulase, capsular polysaccharide, adhesins, proteases, complement inactivating exoproteins, and other innate response modifiers (Powers and Wardenburg, 2014, Journal/PLOS Pathogens, 10(2):e1003871).

Since its first emergence in the 1960s methicillin-resistant SA (MRSA) has become endemic in healthcare settings worldwide (Diep, et al. 2006, *J Infect Dis,* 193 (11): 1495-1503). Since the 1990s, community associated MRSA strains (CA-MRSA) emerged, and are posing a major global challenge (Bassetri, et al., 2009, *Int J Antimicrob Agents,* 34 Suppl 1:S 15-19; Bradley, 2005, *Semin Respir Crit Care Med,* 26 (6):643-649; Chambers, 2005, *N. Engl J Med,* 352 (14): 1485-1487.). There have hence been increasing efforts directed towards the development of vaccines and therapeutics for *S. aureus* infections.

Alpha hemolysin (α-toxin, Hla) is a major virulence factor in SA pneumonia and SSTI (Bubeck Wardenburg and Schneewind, 200K, *J Exp Med,* 205 (2):2K7-294; Kennedy, et al., 2010, *J Infect Dis,* 202 (7): 1050-1058). Recently, cytolytic short peptides known as phenol soluble modulins (PSMs) were identified as key virulence factors that lyse neutrophils, the main line of defense against *S. aureus* (Wang, et al., 2007, *Nat Med,* 13 (12):1510-1514). Another related cytolytic short peptide of staphylococci is known as delta hemolysin or delta toxin (δtoxin) the key marker of *S. aureus* quorum sensing system (agr) (Novick, et al., 1993, *EMBO J,* 12 (10):3967-3975). A recent epidemiological study in a cohort of patients with SA bacteremia shows inverse correlation between probability of sepsis and pre-existing antibodies to Hla, PSM-α3, as well as δ-toxin (Adhikari, et al., 2012, *J Infect Dis,* 206 (6):915-923).

Superantigens (SAgs) constitute a large family of pyrogenic toxins composed of staphylococcal enterotoxins (SEs) and toxic shock syndrome toxin 1 (TSST-1). In contrast to conventional antigens that undergo proteolytic processing by antigen presenting cells and am presented as MHC/peptide complex to T cells, SAgs cross link T cell receptor (TCR) with MHC Class II and activate up to 30% of T cells (Schlievert, 1993, Journal/The Journal of Infectious Diseases, 167(5):997-1002) leading to massive release of cytokines and chemokines, enhanced expression as well as activation of cell-adhesion molecules, increased T-cell proliferation, and eventually T-cell apoptosis/anergy. This sequence of events can culminate in Toxic Shock Syndrome (TSS), a life-threatening condition characterized by rash, hypotension, fever, and multisystem dysfunction (Bohach et al., 1990, Journal/Crit Rev Microbiol, 17(4):251-272). Antibodies play an important rote in protection against TSS, thus individuals that do not seroconvert towards the offending toxin due to hypo responsive T-cells (Mahlknecht et al., 1996, Journal/Hum Immunol. 45(1):42-45) and/or T-cell dependent B-cell apoptosis (Hofer et al., 1996. Journal/Proc Natl Acad Sci USA, 93(11):5425-5430) are more likely to experience recurring bouts. Furthermore, at lower non-TSS inducing concentrations SAgs impact the virulence of *S. aureus* strains through induction of a local excessive inflammatory response.

A major challenge in development of multivalent *S. aureus* vaccines including superantigens is that there are more than 20 different SAgs and there is a wide range of variability in SAg presence in clinical isolates because most SAgs are on mobile genetic elements, such as plasmids or pathogenicity islands (Staphylococcal enterotoxin K (SEK), Staphylococcal enterotoxin Q (SEQ)), lysogenic phages (Staphylococcal enterotoxin A (SEA)), or antibiotic resistance cassettes, like SCC mec Staphylococcal enterotoxin H (SEH) (Omoe et al., 2002, Journal/J Clin Microbiol. 40(3): 857-862). Based on an extensive literature review encompassing over 6000 clinical isolates, the most widely represented super antigens (SAgs) appear to be toxic shock syndrome toxin 1 (TSST-1) and Staphylococcal enterotoxin C (SEC), followed by SEA, Staphylococcal enterotoxin D (SED), and Staphylococcal enterotoxin B (SEB). More recent studies show the emergence of SEK and SEQ, primarily due to circulation of the USA300 clone (Prott and Fraser, 2003, Journal/Clinical and Experimental Immunology, 133(3):299-306). Monoclonal antibodies and vaccination against multiple SAgs have been found to partially protect against SA sepsis in mice. Significant protection has been reported against pneumonia in rabbits using multivalent immunization with various combinations of detoxified SAgs and cytolysins (Spaulding et al., 2012, Vaccine 30(34): 5099-109; Salgado-Pabón et al., 2014, J Infec Dis, 210 (5):784-792).

SUMMARY

In one aspect, this disclosure provides for an attenuated *Staphylococcus aureus*-derived superantigen (SAg) SEA toxoid or an immunogenically or antigenically active fragment, variant, or derivative thereof, comprising four mutations relative to wild-type SEA, the four mutations corresponding to the L48R, D70R, Y92A, and H225A mutations in SEQ ID NO: 4. In certain aspects, the toxoid or fragment, variant, or derivatives thereof, has decreased superantigenic activity and/or is less virulent than a SEA toxoid comprising SEQ ID NO: 3, while maintaining immunogenicity. In certain aspects, the attenuated SEA toxoid or fragment, variant, or derivative thereof comprises an amino acid sequence that is at least 90% identical to SEQ ID NO: 4. In certain aspects, the attenuated SEA toxoid or fragment, variant, or derivative thereof comprises SEQ ID NO: 4. And, in certain aspects, the attenuated SEA toxoid or fragment, variant, or derivative thereof has less than 50%, less than 40%, less than 30%, less than 20%, less than 10%, less than 5%, less than 3%, less than 2%, or less than 1% of the superantigenic activity of a SEA toxoid comprising SEQ ID NO: 3. It will be understood that the nomenclature used herein to describe point mutations (e.g. "L48R") are in comparison to wild-type SAg proteins which do not contain the N-terminal Methionine that was required for heterologous expression.

In another aspect, the disclosure further provides for a multivalent oligopeptide comprising a fusion of two or more attenuated (*Staphylococcus aureus*-derived superantigen (SAg) toxoids or immunogenically or antigenically active fragments, variants, or derivatives thereof as described elsewhere herein arranged in any order, wherein the SAg toxoids or fragments, variants, or derivatives thereof can be the same or different, and wherein at least one of the SAg toxoids is a SEA toxoid described elsewhere herein. In certain aspects, the oligopeptide comprises a fusion of three or more SAg toxoids or fragments, variants, or derivatives thereof. In certain aspects, the oligopeptide has decreased superantigenic activity and/or is less virulent than a SAg fusion protein comprising SEQ ID NO: 5. In certain aspects, the oligopeptide maintains the immunogenicity of the SAg fusion protein comprising SEQ ID NO: 5. In certain aspects, the oligopeptide has less titan 50%, less than 40%, less than 30%, less than 20%, less than 10%, less than 5%, less than 3%, less than 2%, or less than 1% of the superantigenic activity of a SAg fusion protein comprising SEQ ID NO: 5. And, in certain aspects, the oligopeptide is completely attenuated.

In certain aspects, the multivalent oligopeptide comprises one or more of a staphylococcal toxic shock syndrome toxin-1 (TSST-1) attenuated toxoid; a staphylococcal enterotoxin B (SEB) attenuated toxoid; or any combination thereof. In certain aspects, the TSST-1 attenuated toxoid comprises three mutations relative to wild-type TSST-1, the three mutations corresponding to the L30R, D27A, and I46A mutations in SEQ ID NO: 1 and an amino acid sequence at least 90% identical to SEQ ID NO: 1. In certain aspects, the SEB attenuated toxoid comprises three mutations relative to wild-type SEB, the three mutations corresponding to the L45R, Y89A. and Y94A mutations in SEQ ID NO: 2 and an amino acid sequence at least 90% identical to SEQ ID NO: 2. In certain aspects, the SEA attenuated toxoid comprises four mutations relative to wild-type SEA, the four mutations corresponding to the L48R, D70R, Y92A, and H225A mutations in SEQ ID NO: 4 and an amino acid sequence at least 90% identical to SEQ ID NO: 4. In certain aspects, the TSST-1 toxoid comprises the amino acid sequence SEQ ID NO: 1. In certain aspects, the SEB toxoid comprises the amino acid sequence SEQ ID NO: 2. In certain aspects the SEA attenuated toxoid comprises the amino acid sequence SEQ ID NO: 4. In certain aspects, the multivalent oligopeptide comprises the amino acid sequence SEQ ID NO: 6.

In certain aspects, at least two SAg toxoids or fragments, variants, or derivatives thereof described elsewhere herein are each associated via a linker. In certain aspects, the linker comprises at least one, but no more than 50 amino acids selected from the group consisting of glycine, serine, alanine, and a combination thereof. In certain aspects, the linker comprises (GGGS)$_n$ (SEQ ID NO: 13) or (GGGGS)$_n$ (SEQ ID NO: 14), wherein n is a integer from 1 to 10. In certain aspects, the linker comprises (GGGGS)$_n$ (SEQ ID NO: 14). In certain aspects, n is 3 (SEQ ID NO: 15).

The multivalent oligopeptide can Anther comprise a heterologous polypeptide. In certain aspects, the heterologous polypeptide comprises a His-tag, a ubiquitin tag, a NusA tag, a chitin binding domain, a β-tag, a HSB-tag, green fluorescent protein (GFP), a calmodulin binding protein (CBP), a galactose-binding protein, a maltose binding protein (MBP), cellulose binding domains (CBD's), an avidin/streptavidin/Strep-tag, trpE, chloramphenicol acetyltransferase, lacZ (β-Galactosidase), a FLAG™ peptide, an S-tag, a T7-tag, a fragment of any of the heterologous polypeptides, or a combination of two or more of the heterologous polypeptides. In certain aspects, the heterologous polypeptide comprises an immunogen, a T-cell epitope, a B-cell epitope, a fragment thereof, or a combination thereof.

The multivalent oligopeptide can also further comprise an immunogenic carbohydrate. In certain aspects, the immunogenic carbohydrate is a saccharide. In certain aspects, the immunogenic carbohydrate is a capsular polysaccharide or a surface polysaccharide. In certain aspects, the immunogenic carbohydrate is selected from the group consisting of capsular polysaccharide (CP) serotype 5 (CP5), CP8, poly-N-acetylglucosamine (PNAG), poly-N-succinyl glucosamine (PNSG), Wall Teichoic Acid (WTA), Lipoteichoic acid (LTA), a fragment of any of the immunogenic carbohydrates, and a combination of two or more of the immunogenic carbohydrates. In certain aspects, the immunogenic carbohydrate is conjugated to the oligopeptide.

Further provided for is an isolated polynucleotide comprising a nucleic acid that encodes an attenuated SEA toxoid polypeptide described elsewhere herein or a multivalent oligopeptide described elsewhere herein. In certain aspects, the polynucleotide comprises the nucleotide sequence SEQ ID NO: 8. The polynucleotide can further comprise a heterologous nucleic acid. In certain aspects, the heterologous nucleic acid comprises a promoter operably associated with the nucleic acid encoding the oligopeptide. Also provided for is a vector comprising the polynucleotide, in certain aspects, the vector is a plasmid. Also provided for is a host cell comprising the vector. In certain aspects, foe host cell is a bacterium, an insect cell, a mammalian cell, or a plant cell. In certain aspects, the bacterium is *Escherichia coli*.

Further provided is a method of producing a multivalent oligopeptide. In certain aspects, the method comprises culturing a host cell described elsewhere herein and recovering the oligopeptide.

Further provided is a composition, such as a therapeutic, immunogenic, and/or antigenic composition, comprising an attenuated SEA toxoid or multivalent oligopeptide described elsewhere herein, or any combination thereof, and a carrier. The composition can further comprise an adjuvant. In certain aspects, the adjuvant is alum, aluminum hydroxide, aluminum phosphate, or a glucopyranosyl lipid A-based adjuvant. The composition can also further comprise an additional immunogen. In certain aspects, the additional immunogen is a bacterial antigen. In certain aspects, the bacterial antigen is selected from the group consisting of a pore forming toxin, a superantigen, a cell surface protein, a fragment of any of the bacterial antigens, and a combination of two or more of the bacterial antigens.

Further provided is a method of inducing a host immune response against *Staphylococcus aureus*. In certain aspects, the method comprises administering to a subject in need of the immune response an effective amount of an immunogenic or antigenic composition described elsewhere herein. In certain aspects, the immune response is selected from the group consisting of an innate response, a humoral response, an antibody response, a cellular response, and a combination of two or more of the immune responses. In certain aspects, the immune response is an antibody response.

Further provided is a method of preventing or treating a Staphylococcal disease or infection in a subject. In certain aspects, the method comprises administering to a subject in need thereof a composition described elsewhere herein. In certain aspects, the infection is a localized or systemic infection of skin, soft tissue, blood, or an organ, or is auto-immune in nature. In certain aspects, the disease is a respiratory disease, for example, pneumonia. In certain aspects, the disease is sepsis.

A subject in any of the methods disclosed herein can be a mammal. In certain aspects, the mammal is a human. In certain aspects, the mammal is bovine or canine.

A composition for administration in any of the methods disclosed herein can be administered via intramuscular injection, intradermal injection, intraperitoneal injection, subcutaneous injection, intravenous injection, oral administration, mucosal administration, intranasal administration, or pulmonary administration.

Further provided for is a composition for use in inducing a host immune response against *Staphylococcus aureus* in a subject. Further provided for is a composition for use in preventing or treating a Staphylococcal disease or infection in a subject. Further provided for is a method of producing a vaccine against *S. aureus* infection. In certain aspects, the method comprises isolating an attenuated SEA toxoid described elsewhere herein, a multivalent oligopeptide described elsewhere herein, or any combination thereof; and combining the toxoid, oligopeptide, or any combination thereof, with an adjuvant.

BRIEF DESCRIPTION OF THE DRAWINGS/FIGURES

Figure 1:
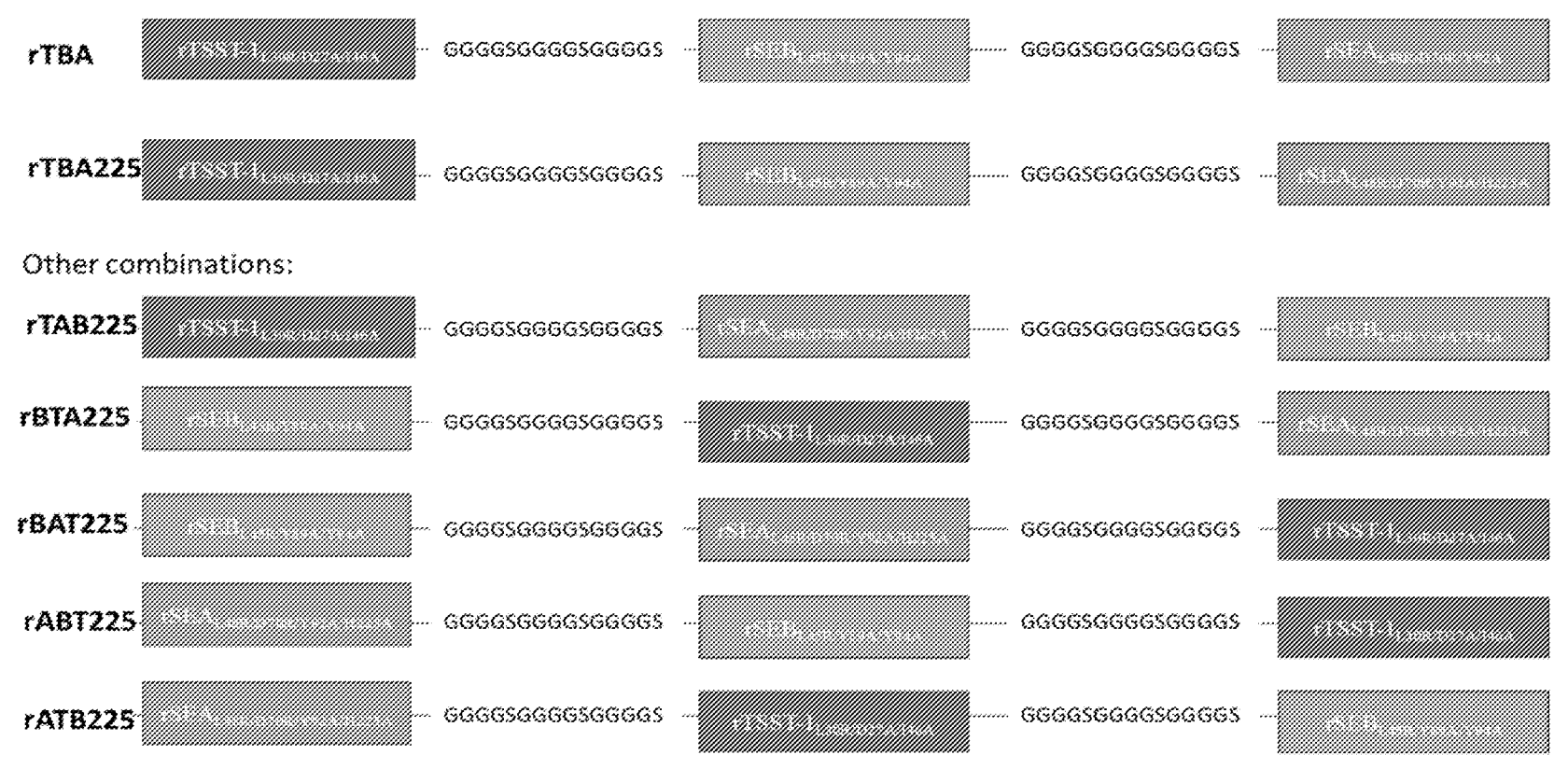

FIG. 1 is a schematic of rTBA and rTBA225 constructs. Additional potential configurations of the fusion peptide are also shown. Linker: three repeats of the linker GGGGS (4GS) (SEQ ID NO: 15).

FIG. 2A-B illustrates purification of rTBA. FIG. 2A) Process for purification of rTBA and rTBA 225. FIG. 2B) SDS-PAGE analysis of rTBA.

Figure 3:
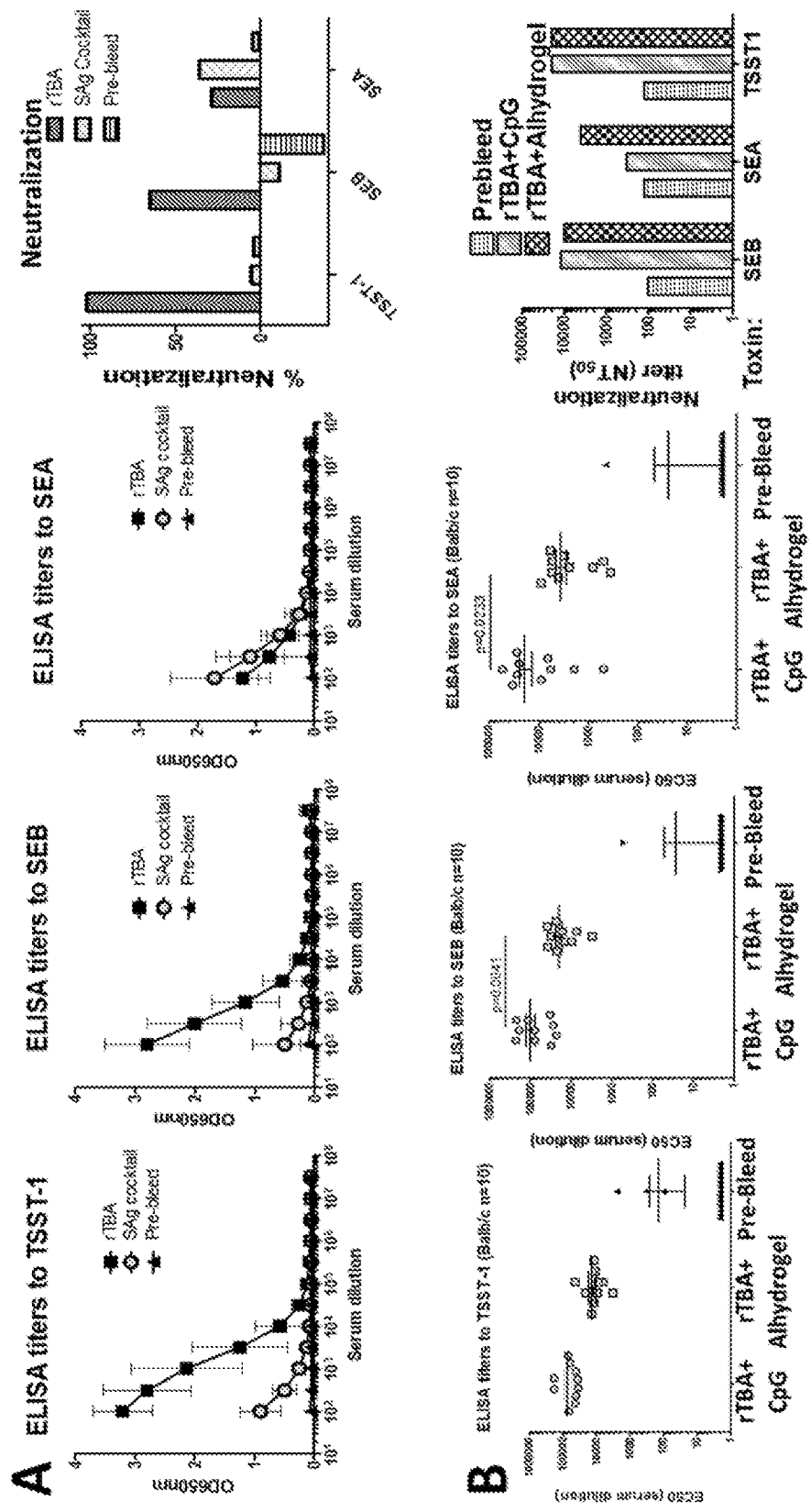

FIG. 3 shows the comparative immunogenicity of rTBA versus a cocktail of the three individual toxoids in mice. A) ELISA and toxin neutralization assay (TNA) were performed on pooled sera from 5 immunized mice per group for the three SAgs. B) Groups of 10 mice were immunized 3 times with rTBA formulated either in CpG or Alhydrogel and immunogenicity was determined in ELISA and TNA assays. Data shown are ELISA $EC_{50}$ and TNA $NT_{50}$ values.

Figure 4:
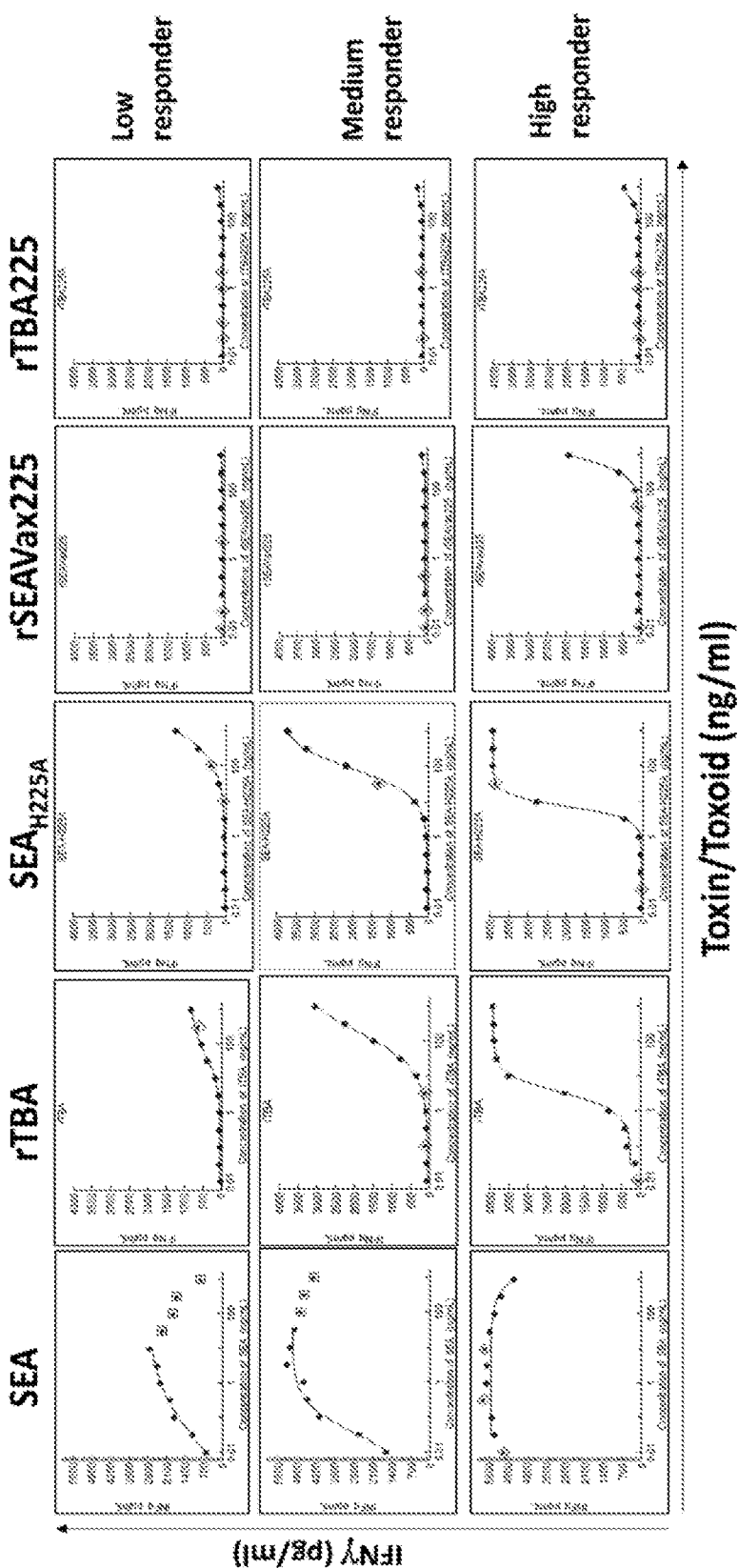

FIG. 4 shows rTBA and rTBA225 safety profiles. Response of human PBMC from three donors to SEA, rTBA, SEAH225A, rSEA225, and rTBA225.

Figure 5:
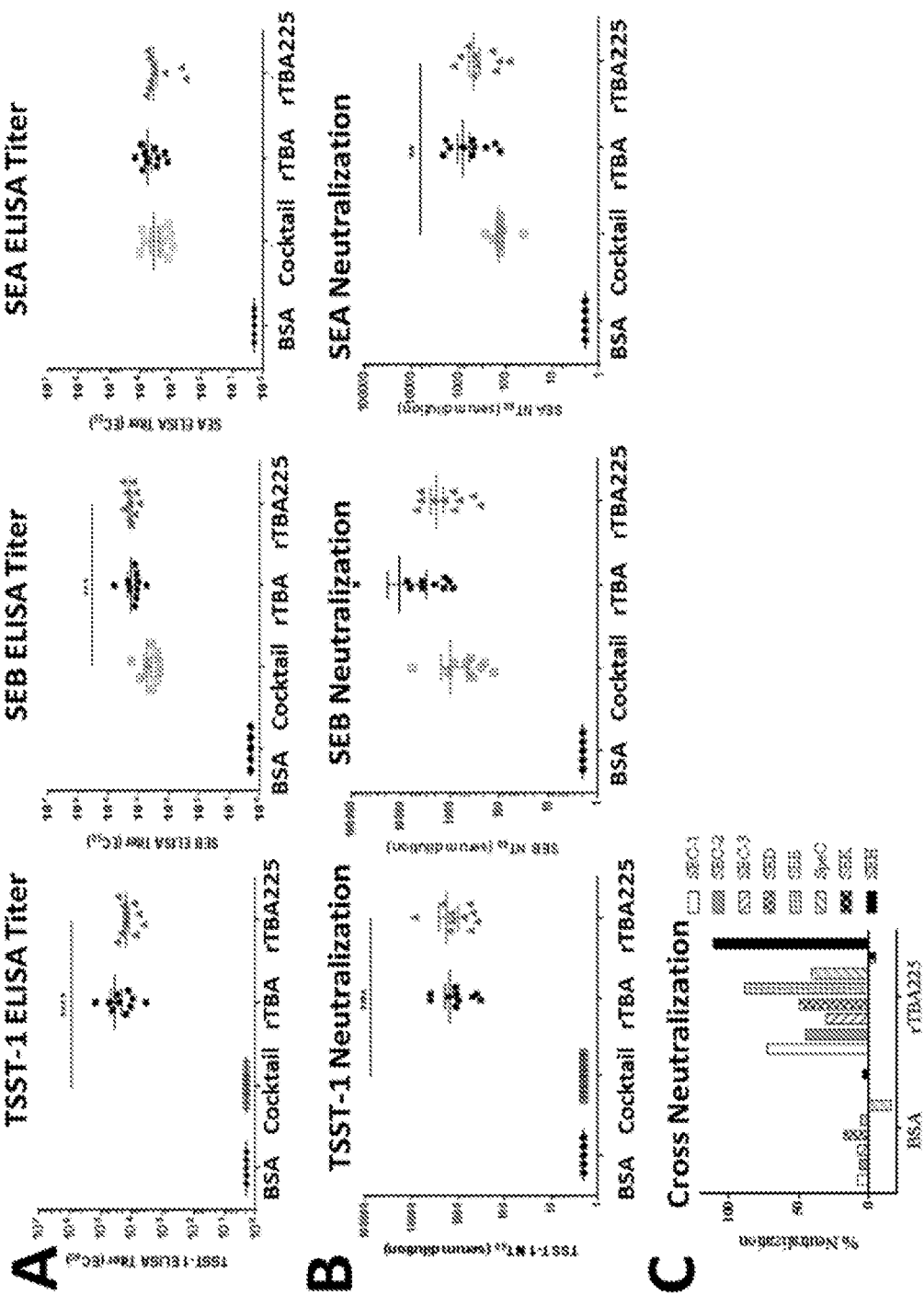

FIG. 5 shows the comparative immunogenicity of rTBA225 versus rTBA versus a cocktail of the three individual toxoids in mice. ELISA and toxin neutralization assay (TNA) were performed on individual sera from 10 immunized mice per group for SEA, SEB and TSST-1. Data shown are ELISA $EC_{50}$ (A) and TNA $NT_{50}$ values (B). TNA to test for cross-neutralization against other super antigens were also performed on pooled sera from the immunized mice. Data shown is percentage neutralization at 1:40 serum dilution (C). Error bars represent standard errors of mean and the asterisks show statistical difference between rTBA225 and SAg cocktail immunized mice sera as determined by the Mann-Whitney non-parametric test.

Figure 6:
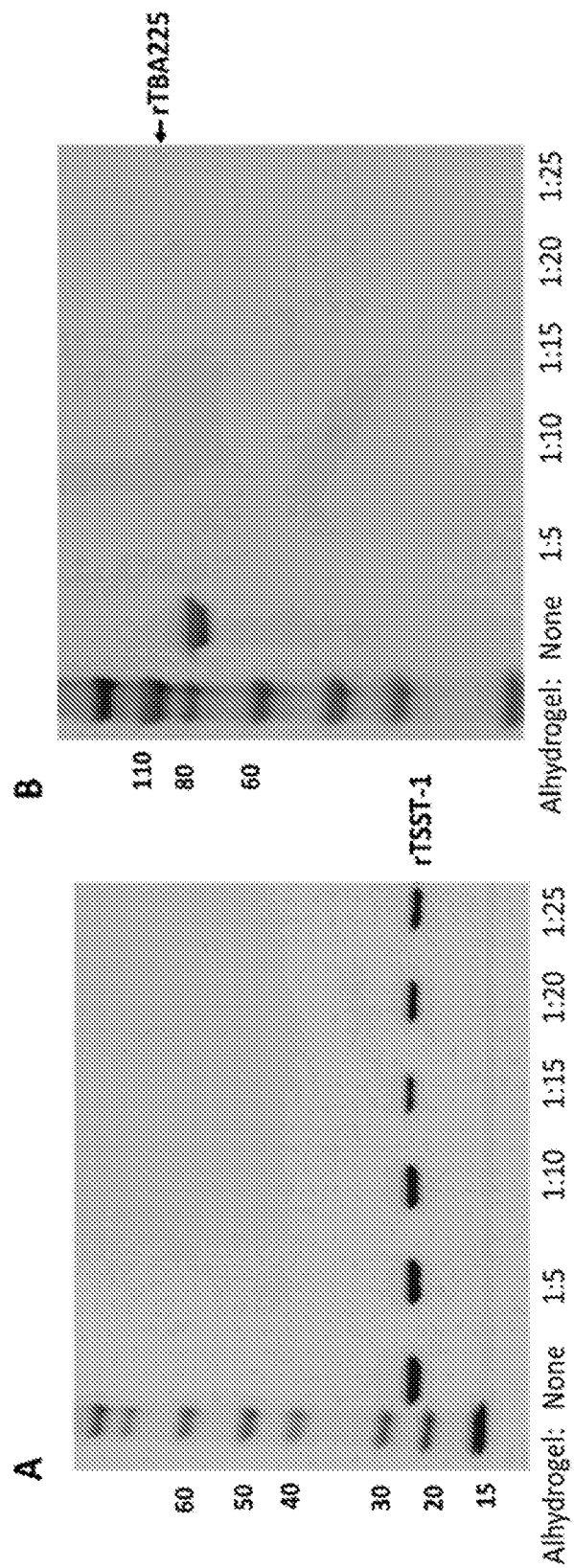

FIG. 6 shows adsorption of rTSST-1 (A) and rTBA225 (B) by Alhydrogel. The proteins were incubated alone (left lanes) or with Alhydrogel at the indicated ratios (protein: Alhydrogel) for 30 minutes at room temperature. Following the incubation the samples were centrifuged to precipitate the adsorbed protein. The supernatant was then subjected to SDS-PAGE analysis and visualized by Coomassie staining. Lack of detectable protein band indicates binding to Alhydrogel.

Figure 7:
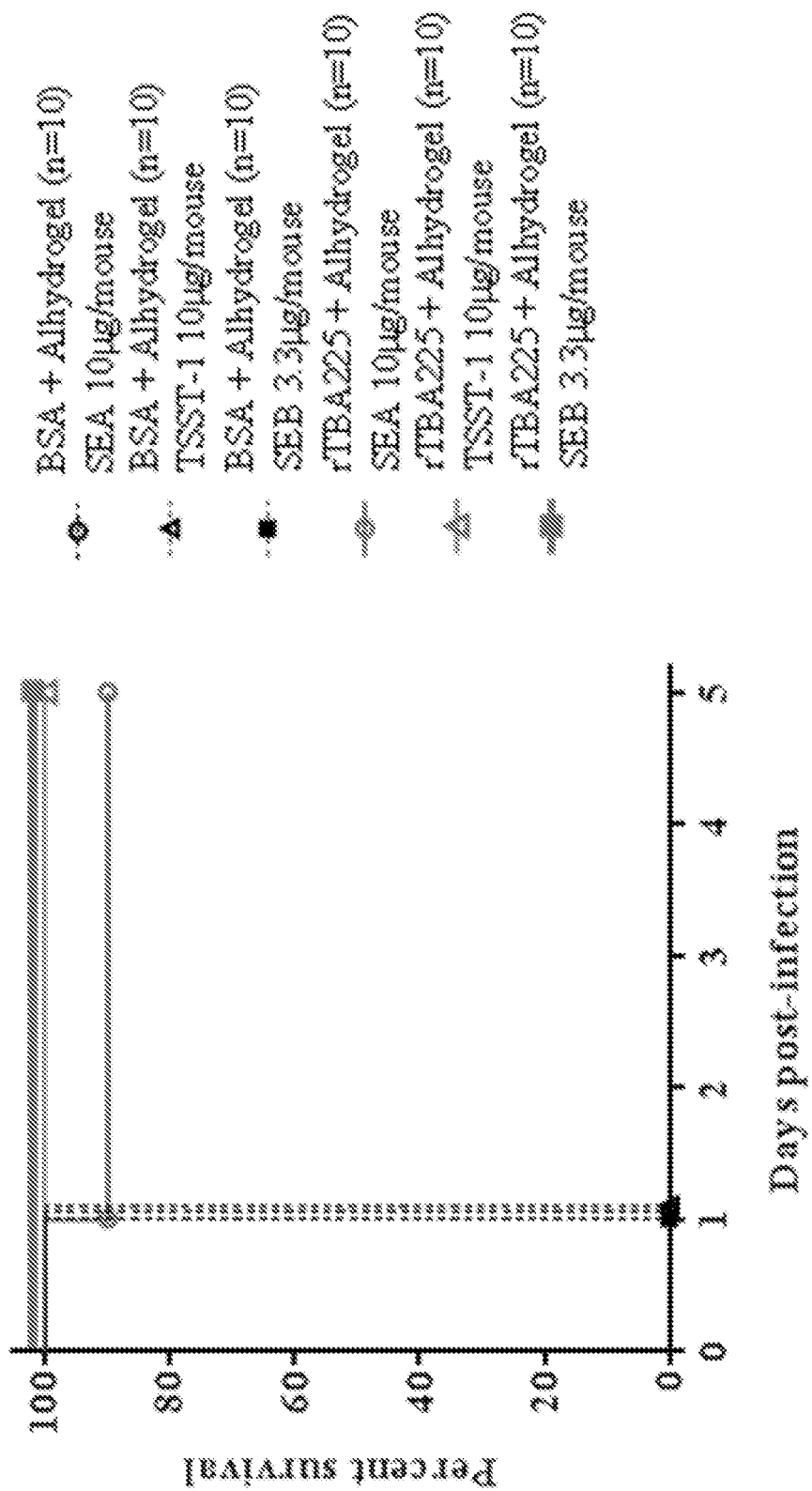

FIG. 7 shows protection provided by rTBA225 against toxin challenge. Groups of 10 mice were vaccinated three times with BSA as a control or rTBA225 formulated in Alhydrogel and challenged with the indicated doses of wild-type TSST-1, SEA, or SEA. Animals were monitored for 5 days for mortality and morbidity.

DETAILED DESCRIPTION

I. Definitions

It is to be noted that the tom "a" or "an" entity refers to one or more of that entity; for example, "a polynucleotide," is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology. Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology. Revised, 2000, Oxford University Press, provide one of skill with a general dictionary of many of the terms used in this disclosure.

Units, prefixes, and symbols are denoted in their Système International dc Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

Wherever aspects or embodiments are described with the language "comprising," otherwise analogous aspects or embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

The terms "nucleic acid" or "nucleic acid fragment" refers to any one or more nucleic acid segments, e.g., DNA or RNA fragments, present in a polynucleotide or construct. Two or more nucleic acids of the disclosure can be present in a single polynucleotide construct, e.g., on a single plasmid, or in separate (non-identical) polynucleotide constructs, e.g., on separate plasmids. Furthermore, any nucleic acid or nucleic acid fragment can encode a single polypeptide, e.g., a single antigen, cytokine, or regulatory polypeptide, or can encode more than one polypeptide, e.g., a nucleic acid can encode two or more polypeptides. In addition, a nucleic acid can encode a regulatory element such as a promoter or a transcription terminator, or can encode a specialized element or motif of a polypeptide or protein, such as a secretory signal peptide or a functional domain.

The term "polynucleotide" is intended to encompass a singular nucleic acid or nucleic acid fragment as well as plural nucleic acids or nucleic acid fragments, and refers to an isolated molecule or construct, e.g., a virus genome (e.g., a non-infectious viral genome), messenger RNA (mRNA), plasmid DNA (pDNA), or derivatives of pDNA (e.g., minicircles as described in (Darquet, A-M et al., *Gene Therapy* 4:1341-1349, 1997) comprising a polynucleotide. A polynucleotide can be provided in linear (e.g., mRNA), circular (e.g., plasmid), or branched form as well as double-stranded or single-stranded forms. A polynucleotide can comprise a conventional phosphodiester bond or a non-conventional bond (e.g., an amide bond, such as found in peptide nucleic acids (PNA)).

As used herein, the term "polypeptide" is intended to encompass a singular "polypeptide" as well as plural "polypeptides," and comprises any chain or chains of two or more amino acids. Thus, as used herein, a "peptide," an "oligopeptide," a "dipeptide," a "tripeptide," a "protein," an "amino acid chain," an "amino acid sequence," "a peptide subunit," or any other term used to refer to a chain or chains of two or more amino acids, are included in the definition of a "polypeptide," (even though each of these terms can have a more specific meaning) and the term "polypeptide" can be used instead of, or interchangeably with any of these terms. The term further includes polypeptides which have undergone post-translational modifications, for example, glycosylation, acetylation, phosphorylation, amidation, derivatization by known protecting/blocking groups, proteolytic cleavage, or modification by non-naturally occurring amino acids.

The term "multivalent oligopeptide" as used herein refers to a fusion protein comprising two or more attenuated staphylococcal proteins, e.g., superantigen (SAg) toxoids or any fragments, variants, or derivatives thereof fused together as a single polypeptide in any order. An oligopeptide can include other heterologous peptides as described elsewhere herein. Other peptides for inclusion in a multivalent oligopeptide provided herein include various other staphylococcal toxoids or fragments, variants, or derivatives thereof, described elsewhere herein or in PCT Publication Nos. WO 2012/109167A1 and WO 2013/082558 A1, which are both incorporated by reference herein in their entireties.

The collection of toxoids and oligopeptides of fusions of toxoids provided by the disclosure are collectively referred to herein as a "multivalent oligopeptide and/or SAg toxoid," or a "multivalent oligopeptide, SAg toxoid, or any combination thereof." These collective references are meant to include, without limitation, any one toxoid or oligopeptide as provided herein, or two, three, four, or more toxoids or oligopeptides as provided herein.

The terms "fragment," "derivative," or "variant" when referring to a multivalent oligopeptide and/or SAg toxoid of the present disclosure include any polypeptide which retains at least some of the immunogenicity or antigenicity of the source protein or proteins. Fragments of multivalent oligopeptides and/or SAgs as described herein include proteolytic fragments, deletion fragments or fragments that exhibit increased solubility during expression, purification, and/or administration to an animal. Fragments of multivalent oligopeptides and/or SAgs as described herein further include proteolytic Augments or deletion fragments which exhibit reduced pathogenicity or toxicity when delivered to a subject. Polypeptide fragments further include any portion of the polypeptide which comprises an antigenic or immunogenic epitope of the source polypeptide, including linear as well as three-dimensional epitopes.

An "epitopic fragment" of a polypeptide is a portion of the polypeptide dial contains an epitope. An "epitopic fragment" can, but need not, contain amino acid sequence in addition to one or more epitopes.

The term "variant," as used herein, refers to a polypeptide that differs from the recited polypeptide due to amino acid substitutions, deletions, insertions, and/or modifications. Non-naturally occurring variants can be produced using art-known mutagenesis techniques. In some aspects, variant polypeptides differ from an identified sequence by substitution, deletion or addition of three amino acids or fewer. Such variants can generally be identified by modifying a polypeptide sequence, and evaluating the antigenic or pathogenic properties of the modified polypeptide using, for example, the representative procedures described herein, in some aspects, variants of a multivalent oligopeptide and/or SAg toxoid form a protein complex which is less toxic than the wild-type complex.

Polypeptide variants disclosed herein exhibit at least about 85%, 90%, 94%, 95%, 96%, 97%, 98%, 99% or 99.9% sequence identity with identified polypeptide. Variant polypeptides can comprise conservative or non-conservative amino acid substitutions, deletions or insertions. Variants can comprise multivalent oligopeptides and/or SAgs identical to the various wild-type staphylococcal proteins except for at least 1, 2, 3, 4, 5, 6, 7, 8, 9, 10, 15, 20, or more amino acid substitutions, including specific mutations described elsewhere herein, where the substitutions render complex less toxic than a corresponding wild-type protein complex. Derivatives of multivalent oligopeptides and/or SAgs as described herein are polypeptides which have been altered so as to exhibit additional features not found on the native polypeptide. Examples include fusion proteins. An analog is another form of a multivalent oligopeptide and/or SAg toxoid described herein. An example is a proprotein which can be activated by cleavage of the proprotein to produce an active mature polypeptide.

Variants can also, or alternatively, contain other modifications, whereby, for example, a polypeptide can be conjugated or coupled, e.g., fused to a heterologous amino acid sequence, e.g., a signal (or leader) sequence at the N-terminal end of the protein which co-translationally or post-translationally directs transfer of the protein. The polypeptide can also be conjugated or produced coupled to a linker or other sequence for case of synthesis, purification or identification of the polypeptide (e.g., 6-His), or to enhance binding of the polypeptide to a solid support. For example, the polypeptide can be conjugated or coupled to an immunoglobulin Fc region. The polypeptide can also be conjugated or coupled to a sequence that imparts or modulates the immune response to the polypeptide (e.g., a T-cell epitope, B-cell epitope, cytokine, chemokine, etc.) and/or enhances uptake and/or processing of the polypeptide by antigen presenting cells or other immune system cells. The polypeptide can also be conjugated or coupled to other polypeptides/epitopes from *Staphylococcus* sp. and/or from other bacteria and/or other viruses to generate a hybrid immunogenic protein that alone or in combination with various adjuvants can elicit protective immunity to other pathogenic organisms. The polypeptide can also be conjugated or coupled to moieties which confer greater stability or improve half life such as, but not limited to albumin, an immunoglobulin Fc region, polyethylene glycol (PEG), and the like. The polypeptide can also be conjugated or coupled to moieties (e.g., immunogenic carbohydrates, e.g., a capsular polysaccharide or a surface polysaccharide) from *Staphylococcus* sp. and/or from other bacteria and/or other viruses to generate a modified immunogenic protein that alone or in combination with one or more adjuvants can enhance and/or synergize protective immunity. In certain aspects, the polypeptide described herein further comprises an immunogenic carbohydrate. In one aspect, the immunogenic carbohydrate is a saccharide.

The term "saccharide" throughout this specification can indicate polysaccharide or oligosaccharide and includes both. Polysaccharides of the disclosure can be isolated from bacteria and can be sized by known methods. For example, full length polysaccharides can be "sized" (e.g., their size can be reduced by various methods such as acid hydrolysis treatment, hydrogen peroxide treatment, sizing by EMULSIFLEX® followed by a hydrogen peroxide treatment to generate oligosaccharide fragments or microfluidization). Polysaccharides can be sized in order to reduce viscosity in polysaccharide samples and/or to improve filterability for conjugated products. Oligosaccharides have a low number of repeat units (e.g., 5-30 repeat units) and are typically hydrolyzed polysaccharides. Polysaccharides of the disclosure can be produced recombinantly.

*S. aureus* capsular antigens are surface associated, limited in antigenic specificity, and highly conserved among clinical isolates. In one aspect, the immunogenic carbohydrate of the disclosure is a capsular polysaccharide (CP) of *S. aureus*. In one aspect, a capsular saccharide can be a full length polysaccharide, however in other aspects it can be one oligosaccharide unit, or a shorter than native length saccharide chain of repeating oligosaccharide units. Serotyping studies of staphylococcal isolates have revealed several putative capsular serotypes, with types 5 and 8 (CP5 and CP8) being the most prevalent among isolates from clinical infections, accounting for about 25% and 50% of isolates recovered from humans, respectively (O'Riordan and Lee, Clinical Microbiology Reviews, January 2004, p. 218-234, Vol. 17, No. 1; Poutrel and Sutra, J Clin Microbiol. 1993 February; 31(2):467-9). The same isolates were also recovered from poultry, cows, horses and pigs (Tollersrud et al., J Clin Microbiol. 2000 August; 38(8):2998-3003; Cunnion KM et al., Infect Immun, 2001 November; 69(11):6796-803). Type 5 and 8 capsular polysaccharides purified from the prototype strains Reynolds and Becker, respectively, are structurally very similar to each other and to the capsule made by strain T, described previously by Wu and Park (Wu and Park. 1971. J. Bacteriol. 108:874-884). Type 5 has the structure (→4)-3-O-Ac-β-D-ManNAcA-(1→4)-α-L-FucNAc-(1→3)-β-D-FucNAc-(1→)$_n$ (Fournier, J. M., et al., 1987. Ann. Inst. Pasteur Microbiol. 138:561-567; Moreau, M., et al., 1990. Carbohydr. Res. 201:285-297), and type 8 has the structure. (→3)-4-O-Ac-β-D-ManNAcA-(1→3)-α-L-FucNAc-(1→3)-β-D-FucNAc-(1→)$_n$ (Fournier, J. M., et al., 1984. Infect. Immun. 45:87-93). Type 5 and 8 polysaccharides differ only in the linkages between the sugars and in the sites of O-acetylation of the mannosaminuronic acid residues, yet they are serologically distinct.

Type 5 and 8 CP conjugated to a detoxified recombinant *Pseudomonas aeruginosa* exotoxin A carrier were shown to be highly immunogenic and protective in a mouse model (A Fattom et al., Infect Immun. 1993 March; 61(3): 1023-1032; A Fattom et al., Infect Immun. 1996 May; 64(5): 1659-1665) and passive transfer of the CP5-specific antibodies from the immunized animals induced protection against systemic infection in mice (Lee et al., Infect Immun. 1997 October; 65(10): 4146-4151) and against endocarditis in rats challenged with a serotype 5 *S. aureus* (Shinefield H et al., N Engl J Med. 2002 Feb 14; 346(7):491-6). A bivalent CP5 and CP8 conjugate vaccine (StaphVAX®, Nabi Biopharmaceutical) was developed that provided 75% protection in mice against *S. aureus* challenge. The vaccine has been tested on humans (Fattom A I et al., Vaccine. 2004 Feb. 17; 22(7): 880-7; Maira-Litrán T et al., Infect Immun. 2005 October; 73(10):6752-62). In certain aspects, the recombinant peptide or multivalent oligopeptide of the disclosure is combined with or conjugated to an immunogenic carbohydrate (e.g., CP5, CP8, a CP fragment or a combination thereof).

Immunization with poly-N-acetylglucosamine (PNAG) (McKenney D. et al., Science. 1999 May 28; 284(5419): 1523-7) or poly-N-succinyl glucosamine (PNSG) (Tuchscherr L P. et al., Infect Immun. 2008 December; 76(12): 5738-44. Epub 2008 Sep. 22), both *S. aureus* surface carbohydrates, has been shown to generate at least partial protection against *S. aureus* challenge in experimental animal models. PNSG was identified as the chemical form of the *S. epidermidis* capsular polysaccharide/adhesin (PS/A) which mediates adherence of coagulase-negative staphylococci (CoNS) to biomaterials, serves as the capsule for strains of CoNS that express PS/A, and is a target for protective antibodies. PNSG is also made by *S. aureus*, where it is an environmentally regulated, in vivo-expressed surface polysaccharide and similarly serves as a target for protective immunity (McKenney D. et al., J. Biotechnol. 2000 Sep. 29; 83(1-2): 37-44). In certain aspects of the disclosure, the immunogenic carbohydrate is a surface polysaccharide, e.g., poly-N-acetylglucosamine (PNAG), poly-N-succinyl glucosamine (PNSG), a surface polysaccharide fragment or a combination thereof.

Wall Teichoic Acid (WTA) is a prominent polysaccharide widely expressed on *S. aureus* strains (Neuhaus, F. C. and J. Baddiley, Microbiol Mol Biol Rev, 2003. 67(4):686-723) and antisera to WTA have been shown to induce opsonophagocytic killing alone and in presence of complement ((Thakker, M., et al., Infect Immun, 1998. 66(11): 5183-9), and Fattom et al, U.S. Pat. No. 7,754,225). WTA is linked to peptidoglycans and protrudes through the cell wall becoming prominently exposed on non-encapsulated strains such as USA300 responsible for most cases of community acquired MRSA (CA MRSA) in the US (Hidron, A. I., et al., Lancet Infect Dis, 2009. 9(6):384-92).

Lipoteichoic acid (LTA) is a constituent of the cell wall of Gram-positive bacteria, e.g., *Staphylococcus aureus*. LTA can bind to target cells non-specifically through membrane phospholipids, or specifically to CD14 and to Toll-like receptors. Target-bound LTA can interact with circulating antibodies and activate the complement cascade to induce a passive immune kill phenomenon. It also triggers the release from neutrophils and macrophages of reactive oxygen and nitrogen species, acid hydrolases, highly cationic proteinases, bactericidal cationic peptides, growth factors, and cytotoxic cytokines, which can act in synergy to amplify cell damage.

In certain aspects, a surface polysaccharide is combined with or conjugated to a polypeptide of the disclosure. In certain aspects the surface polysaccharide is, e.g., poly-N-acetylglucosamine (PNAG), poly-N-succinyl glucosamine (PNSG), Wall Teichoic Acid (WTA), Lipoteichoic acid (LPA), a fragment of any of said surface polysaccharides, or a combination of two or more of said surface polysaccharides.

The term "sequence identity" as used herein refers to a relationship between two or more polynucleotide sequences or between two or more polypeptide sequences. When a position in one sequence is occupied by the same nucleic acid base or amino acid in the corresponding position of the comparator sequence, the sequences are said to be "identical" at that position. The percentage "sequence identity" is calculated by determining the number of positions at which the identical nucleic acid base or amino acid occurs in both sequences to yield the number of "identical" positions. The number of "identical" positions is then divided by the total number of positions in the comparison window and multiplied by 100 to yield the percentage of "sequence identity." Percentage of "sequence identity" is determined by comparing two optimally aligned sequences over a comparison window and a homologous polypeptide from another isolate. In order to optimally align sequences for comparison, the portion of a polynucleotide or polypeptide sequence in the comparison window can comprise additions or deletions termed gaps while the reference sequence is kept constant. An optimal alignment is that alignment which, even with gaps, produces the greatest possible number of "identical" positions between the reference and comparator sequences. Percentage "sequence identity" between two sequences can be determined using the version of the program "BLAST 2 Sequences" which is available from the National Center for Biotechnology Information as of Sep. 1, 2004, which program incorporates the programs BLASTN (for nucleotide sequence comparison) and BLASTP (for polypeptide sequence comparison), which programs are based on the algorithm of Karlin and Altschul (*Proc. Natl. Acad. Sci. USA* 90(12):5873-5877, 1993). When utilizing "BLAST 2 Sequences," parameters that were default parameters as of Sep. 1, 2004, can be used for word size (3), open gap penalty (11), extension gap penalty (1), gap drop-off (50), expect value (10) and any other required parameter including but not limited to matrix option.

The term "epitope," as used herein, refers to portions of a polypeptide having antigenic or immunogenic activity in an animal for example a mammal, for example, a human. An "immunogenic epitope," as used herein, is defined as a portion of a protein that elicits an immune response in an animal, as determined by any method known in the art. The term "antigenic epitope," as used herein, is defined as a portion of a protein to which an antibody or T-cell receptor can immunospecifically bind its antigen as determined by any method well known in the art. Immunospecific binding excludes non-specific binding but does not necessarily exclude cross-reactivity with other antigens. Whereas all immunogenic epitopes are antigenic, antigenic epitopes need not be immunogenic.

As used herein, a "coding region" is a portion of nucleic acid which consists of codons translated into amino acids. Although a "stop codon" (TAG, TGA, or TAA) is not translated into an amino acid, it can be considered to be part of a coding region, but any flanking sequences, for example promoters, ribosome binding sites, transcriptional terminators, and the like, are outside the coding region.

The term "codon optimization" is defined herein as modifying a nucleic acid sequence for enhanced expression in the cells of the host of interest by replacing at least one, more than one, or a significant number, of codons of the native sequence with codons that are more frequently or most frequently used in the genes of that host Various species exhibit particular bias for certain codons of a particular amino acid.

The terms "composition" or "pharmaceutical composition" can include compositions containing immunogenic polypeptides of the disclosure along with e.g., adjuvants or pharmaceutically acceptable carriers, excipients, or diluents, which are administered to an individual already suffering from *S. aureus* infection or an individual in need of immunization against *S. aureus* infection.

The term "pharmaceutically acceptable" refers to compositions that are, within the scope of sound medical judgment, suitable for contact with the tissues of human beings and animals without excessive toxicity or other complications commensurate with a reasonable benefit/risk ratio. In some aspects, the polypeptides, polynucleotides, compositions, and vaccines described herein are pharmaceutically acceptable.

An "effective amount" is that amount the administration of which to an individual, either in a single dose or as part of a series, is effective for treatment or prevention. An amount is effective, for example, when its administration results in a reduced incidence of *S. aureus* infection relative to an untreated individual, as determined, after infection or challenge with infectious *S. aureus*, including, but is not limited to reduced bacteremia, reduced toxemia, reduced sepsis, reduced symptoms, increased immune response, modulated immune response, or reduced time required for recovery. This amount varies depending upon the health and physical condition of the individual to be treated, the taxonomic group of individual to be treated (e.g., human, non-human primate, primate, etc.), the responsive capacity of the individual's immune system, the extern of treatment or protection desired the formulation of the vaccine, a professional assessment of the medical situation, and other relevant factors. It is expected that the effective amount will foil in a relatively broad range that can be determined through routine trials. Typically a single dose is from about 10 µg to 10 mg/kg body weight of purified polypeptide or an amount of a modified carrier organism or virus, or a fragment or remnant thereof, sufficient to provide a comparable quantity of recombinantly expressed multivalent oligopeptide and/or SAg toxoid as described herein. The term "peptide vaccine" or "subunit vaccine" refers to a composition comprising one or more polypeptides described herein, which when administered to an animal are useful in stimulating an immune response against staphylococcal *S. aureus*) infection.

The term "subject" is meant any subject, particularly a mammalian subject, for whom diagnosis, prognosis, immunization, or therapy is desired. Mammalian subjects include, but are not limited to, humans, domestic animals, form animals, zoo animals such as bears, sport animals, pet animals such as dogs, cats, guinea pigs, rabbits, rats, mice, horses, cattle, bears, cows; primates such as apes, monkeys, orangutans, and chimpanzees; canids such as dogs and wolves; felids such as cats, lions, and tigers; equids such as horses, donkeys, and zebras: food animals such as cows, pigs, and sheep; ungulates such as deer and giraffes; rodents such as mice, rats, hamsters and guinea pigs; and so on. In one aspect, the subject is a human subject.

As used herein, a "subject in need thereof" refers to an individual for whom it is desirable to treat, i.e., to prevent, cure, retard, or reduce the severity of staphylococcal (e.g., *S. aureus*) disease symptoms, or result in no worsening of disease cause by *S. aureus* over a specified period of time, or both.

The terms "priming" or "primary" and "boost" or "boosting" as used herein refer to the initial and subsequent immunizations, respectively, i.e., in accordance with the definitions these terms normally have in immunology. However, in certain aspects, e.g., where the priming component and boosting component are in a single formulation, initial and subsequent immunizations are not be necessary as both the "prime" and the "boost" compositions are administered simultaneously.

As used herein, "superantigenic activity" is a measure of a multivalent oligopeptide's or SAg toxoid's residual toxicity and can be measured in comparison to that of a wild-type SAg toxin or to another reference SAg toxoid or SAg toxoid containing multivalent oligopeptide. For purposes of this disclosure, an increase or decrease in "superantigenic activity" in comparison to a reference polypeptide can be determined by measuring the activity of a SAg toxin, toxoid, or oligopeptide against isolated peripheral blood mononuclear cells (PBMCs) in an in vitro stimulation assay as described elsewhere herein.

II. Superantigen (SAg) Toxoids and Multivalent Oligopeptides

This disclosure provides for recombinant oligopeptide fusion proteins comprised of attenuated polypeptide subunits, referred to herein as "toxoids," derived from Staphylococcal superantigens. In certain aspects, the SAg toxoid is attenuated by one or more mutations to decrease its superantigenic activity, toxicity, and/or virulence, while maintaining its immunogenicity. Accordingly, this disclosure provides for an attenuated *Staphylococcus aureus*-derived superantigen (SAg) Staphylococcal enterotoxin A (SEA) toxoid or fragment, variant, or derivative thereof, comprising four mutations relative to wild-type SEA corresponding to L48R, D70R, Y92A, and H225A mutations in SEQ ID NO: 4. In certain aspects, the attenuated SEA toxoid or fragment, variant, or derivative thereof, having the four specified mutations, comprises an amino acid sequence that is at least 90% identical to SEQ ID NO: 4. In certain aspects, the attenuated SEA toxoid or fragment, variant, or derivative thereof comprises and/or consists of SEQ ID NO: 4. It will be understood that the nomenclature used herein to describe point mutations (e.g. "L48R") are in comparison to wild-type SAg proteins which do not contain the N-terminal Methionine that was required for heterologous expression.

In certain aspects, the SEA toxoid or fragment, variant, or derivatives thereof, having the four specified mutations, has decreased superantigenic activity, decreased toxicity, and/or is less virulent than a wild-type SEA toxin. In certain aspects, the SEA toxoid or fragment, variant, or derivatives thereof, having the four specified mutations, has decreased superantigenic activity, decreased toxicity, and/or is less virulent than a SEA toxoid comprising SEQ ID NO: 3 ($SEA_{L48R/D70R/Y92A}$). In certain aspects, the SEA toxoid or fragment, variant, or derivatives thereof, having the four specified mutations, has decreased superantigenic activity, decreased toxicity, and/or is less virulent than a SEA toxoid consisting of SEQ ID NO: 3.

In certain aspects, the attenuated SEA toxoid or fragment, variant, or derivative thereof, having the four specified mutations, has less than 50%, less than 40%, less than 30%, less than 20%, less than 10%, less than 5% less than 3%, less than 2%, or less than 1% of the superantigenic activity of a wild-type SEA toxin. In certain aspects, the attenuated SEA toxoid or fragment, variant, or derivative thereof having the four specified mutations, has less than 50%, less than 40%, less than 30%, less than 20%, less than 10%, less than 5%, less than 3%, less than 2%, or less than 1% of the superantigenic activity of a SEA toxoid comprising SEQ ID NO: 3. In certain aspects, the attenuated SEA toxoid or fragment, variant, or derivative thereof, having the four specified mutations, has less than 50%, less than 40%, less than 30%, less than 20%, less than 10%, less than 5%, less than 3%, less than 2%, or less than 1% of the superantigenic activity of a SEA toxoid consisting of SEQ ID NO: 3.

In certain aspects of any of the attenuated SEA toxoids or fragments, variants, or derivatives thereof, comprising four mutations relative to wild-type SEA corresponding to the L48R, D70R, Y92A, and H225A mutations in SEQ ID NO: 4 as disclosed herein, immunogenicity is maintained as compared to a wild-type SEA toxin, a SEA toxoid comprising SEQ ID NO: 3, and/or a SEA toxoid consisting of SEQ ID NO: 3. In certain aspects, immunization with the SEA toxoid or fragment, variant, or derivative thereof comprising the four specified mutations, elicits neutralizing antibodies against a wild-type SEA toxin.

Further, in certain aspects, this disclosure provides a multivalent oligopeptide comprising a fusion of two or more, e.g., two, three, four, five, six, seven, eight, nine, ten or more *Staphylococcus aureus*-derived toxoids or fragments, variants, or derivatives thereof arranged in any order. The two or more *Staphylococcus aureus*-derived toxoids or fragments, variants, or derivatives thereof of the multivalent oligopeptide can be the same or different.

U.S. Publication No. 2016/0185829 A1 (incorporated herein by reference) describes a simplified Superantigen (SAg) toxoid vaccine comprising a fusion oligopeptide of mutants of Superantigens, namely recombinant TS-ST-$1_{L30R/D27A/I46A}$ (SEQ ID NO: 1), $SEB_{L45R/Y89A/Y94A}$ (SEQ ID NO: 2), and $SEA_{L48R/D70R/Y92A}$ (SEQ ID NO: 3). This multivalent oligopeptide is referred to herein as rTBA (FIG. 1) and has the amino acid sequence SEQ ID NO: 5. The rTBA construct was capable of inducing broad neutralizing antibodies. This fusion protein induced a better total antibody and neutralizing response compared to a simple mixture of the three individual toxoids, but it retained some residual superantigenic activity.

Provided herein is a multivalent oligopeptide that improves upon rTBA. In certain aspects, the multivalent oligopeptide comprises a fusion protein of two or more SAg toxoids having reduced superantigenic activity, toxicity, and/or virulence relative to a SAg fusion protein comprising and/or consisting of SEQ ID NO: 5. In certain aspects, the multivalent oligopeptide Has less than 50%, less than 40%, less than 30%, less than 20%, less than 10%, less than 5%, less than 3%, less than 2%, or less than 1% of the superantigenic activity, toxicity, and/or virulence of a wild-type SEA toxin and/or a SAg fusion protein comprising SEQ ID NO: 5 (FIG. 4). In certain aspects, the multivalent oligopeptide maintains the immunogenicity of the SAg fusion protein comprising and/or consisting of SEQ ID NO: 5. In certain aspects, immunization with the multivalent oligopeptide elicits neutralizing antibodies against a SAg TSST-1 toxin, a SAg SEB toxin, a SAg SEA toxin, or any combination thereof. In certain aspects, immunization with the multivalent oligopeptide elicits neutralizing antibodies to SAg toxins other than TSST-1, SEB, or SEA. In certain aspects, the multivalent oligopeptide exhibits greater and/or broader immunogenicity than an equimolar cocktail of the individual SAg toxoids from which it is composed (FIG. 5). In certain aspects, immunization of a subject with the multivalent oligopeptide provides protection against at least one or more of wild-type SAg TSST-1 toxin, wild-type SAg SEB toxin, and wild-type SAg SEA toxin (FIG. 7). In certain aspects, the multivalent oligopeptide or a composition comprising the oligopeptide can be used to treat or prevent a Staphylococcal disease or infection.

In certain aspects of this disclosure, a multivalent oligopeptide includes a staphylococcal SAg toxoid or fragment, variant, or derivative thereof including, without limitation, a toxoid derivative of staphylococcal enterotoxin A (SEA), staphylococcal enterotoxin B (SEB), staphylococcal enterotoxins C1-3 (SECI-3), staphylococcal enterotoxin E (SEE), staphylococcal enterotoxin H (SHE), staphylococcal enterotoxin I (SEI), staphylococcal enterotoxin K (SEK), staphylococcal toxic shock syndrome toxin-1 (TSST-1), streptococcal pyrogenic exotoxin C (SpeC), staphylococcal enterotoxin D (SED), streptococcal pyrogenic exotoxin A (SpeA), or any combination thereof, in any order.

In certain aspects, the multivalent oligopeptide includes a staphylococcal toxic shock syndrome toxin-1 (TSST-1) toxoid or fragment, variant, or derivative thereof. In certain aspects, the TSST-1 toxoid is the attenuated toxoid TSST-$1_{L30R/D27A/I46A}$ (SEQ ID NO: 1), or a TSST-1 toxoid comprising the three attenuating mutations relative to wild-type TSST-1 corresponding to the L30R, D27A, and I46A mutations in SEQ ID NO: 1 and an amino acid sequence at least 75%, 80%, 85%, 90%, 95%, 96%, 97%, 98%, or 99% identical to SEQ ID NO: 1. In certain aspects, the oligopeptide includes a staphylococcal enterotoxin B (SEB) toxoid or fragment, variant, or derivative thereof. In certain aspects, the SEB toxoid is the attenuated toxoid $SEB_{L45R/Y89A/Y94A}$ (SEQ ID NO: 2), or a SEB toxoid comprising the three attenuating mutations relative to wild-type SEB corresponding to the L45R, Y89A, and Y94A mutations in SEQ ID NO: 2 and an amino acid sequence at least 75%, 80%, 85%, 90%, 95%, 96%, 97%, 98%, or 99% identical to SEQ ID NO: 2. In certain aspects, the oligopeptide includes a staphylococcal enterotoxin A (SEA) toxoid or fragment, variant, or derivative thereof. In certain aspects, the SEA toxoid is the attenuated toxoid $SEA_{L48R/D70R/Y92A/H225A}$ (SEQ ID NO: 4), or an SEA toxoid comprising the four attenuating mutations relative the wild-type SEA corresponding to the L48R, D70R, Y92A, and H225A mutations in SEQ ID NO: 4 and an amino acid sequence at least 75%, 80%, 85%, 90%, 95%, 96%, 97%, 98%, or 99% identical to SEQ ID NO: 4.

In certain aspects, a multivalent oligopeptide as provided herein comprises at least one Staphylococcal enterotoxin A (SEA) attenuated toxoid comprising four mutations relative to wild-type SEA corresponding to the L48R, D70R, Y92A, and H225A mutations in $SEA_{L48R/D70R/Y92A/H225A}$ (SEQ ID NO: 4) as described elsewhere herein. In certain aspects, the multivalent oligopeptide comprises two or more or three or more SAg toxoids or fragments, variants, or derivatives thereof. In certain aspects, the oligopeptide further comprises a staphylococcal enterotoxin B (SEB) attenuated toxoid as described elsewhere herein, a staphylococcal toxic shock syndrome toxin-1 (TSST-1) attenuated toxoid as described elsewhere herein, and any combination thereof. In certain aspects, the TSST-1 toxoid comprises three mutations relative to wild-type TSST-1 corresponding to the L30R, D27A, and I46A mutations in SEQ ID NO: 1 and an amino acid sequence at least 90% identical to SEQ ID NO: 1; the SEB toxoid comprises three mutations relative to wild-type SEB corresponding to the L45R, Y89A, and Y94A mutations in SEQ ID NO: 2 and an amino acid sequence at least 90% identical to SEQ ID NO: 2; and the SEA attenuated toxoid comprises four mutations relative to wild-type SEA corresponding to the L48R, D70R, Y92A, and H225A mutations in the SEA toxoid of SEQ ID NO: 4 and an amino acid sequence at least 90% identical to SEQ ID NO: 4. In certain aspects, the TSST-1 toxoid comprises the amino acid sequence SEQ ID NO: 1; the SEB toxoid comprises the amino acid sequence of SEQ ID NO: 2; and the SEA attenuated toxoid comprises the amino acid sequence SEQ ID NO: 4.

In certain aspects, the multivalent oligopeptide includes the SAg attenuated toxoids $SEB_{L45R/Y89A/Y94A}$ ("B"), $SEA_{L48R/D70R/Y92A/H225A}$ ("A225"), TSST-$1_{L30R/D27A/I46A}$ ("T"), or any combination thereof. In certain aspects, the multivalent oligopeptide includes at least $SEA_{L48R/D70R/Y92A/H225A}$. In certain aspects, the multivalent oligopeptide comprises, consists of, or consists essentially of a "TBA225" fusion (rTBA225; SEQ ID NO: 6), which is a fusion of TSST-$1_{L30R/D27A/I46A}$, $SEB_{L45R/Y89A/Y94A}$, and $SEA_{L48R/D70R/Y92A/H225A}$, in that order. Or the oligopeptide has the attenuating mutations corresponding to those of $SEB_{L45R/Y89A/Y94A}$, $SEA_{L48R/D70R/Y92A/H225A}$, and TSST-$1_{L30R/D27A/I46A}$, wherein the oligopeptide comprises, consists, or consists essentially of an amino acid sequence at least 75%, 80%, 85%, 90%, 95%, 96%, 97%, 98%, or 99% identical to SEQ ID NO: 6.

As noted, in certain aspects, the multivalent oligopeptide is rTBA225 (SEQ IN NO: 6), which is a fusion of the SAg triple mutants TSST-$1_{L30R/D27A/I46A}$ (SEQ ID NO: 1) and $SEB_{L45R/Y89A/Y94A}$ (SEQ ID NO: 2) and SEA quadruple mutant $SEA_{L48R/D70R/Y92A/H225A}$ (SEQ ID NO: 4). rTBA225 retains the superior immunogenicity of rTBA (SEQ ID NO: 5) while having reduced superantigenic activity. Additional possible configurations with different orderings of the aforementioned SAg toxoids are shown in FIG. 1. Also provided for in this disclosure is a method for tag-free purification of rTBA and rTBA225.

The SAg toxoids can be linked together in any order, either with our without linkers, and can be the same or different. In some aspects, the SAg toxoids included in the multivalent oligopeptide can be directly fused to each other. In other aspects, the SAg toxoids included in the multivalent oligopeptide can be associated via a linker. Suitable linkers can be chosen based on their ability to adopt a flexible, extended conformation, or a secondary structure that can interact with joined epitopes, or based on their ability to increase overall solubility of the fusion polypeptide, or based on their lack of electrostatic or water-interaction effects that influence joined peptide regions. In certain aspects, the linker is a peptide linker. In certain aspects, a peptide linker for use in a multivalent oligopeptide as provided herein can include at least one, but no more than 50 amino acids, e.g., small amino acids that provide a flexible chain, e.g., glycine, serine, alanine, or a combination thereof. In certain aspects, a linker for use in a multivalent oligopeptide as provided herein can include $(GGGS)_n$ (SEQ ID NO: 13) or $(GGGGS)_n$ (SEQ ID NO: 14), wherein n is a integer from 1 to 10. In certain aspects, such as in the fusion peptide rTBA225 (SEQ ID NO: 6), the linker is a $(GGGGS)_n$ linker in which n=3 (SEQ ID NO: 15).

In certain aspects the multivalent oligopeptide comprises, consists of, or consists essentially of the amino acid sequence SEQ ID NO: 6.

TABLE 1

SAgs and Multivalent Oligopeptide Protein Sequences

| | | SEQ ID NO |
|---|---|---|
| TSST-1$_{L30R/D27A/I46A}$<br>(Mutations relative to<br>wild-type<br>bold/underlined) | MSTNDNIKDLLDWYSSGSDTFTNSEVLANSRGSMR<br>IKNTDGSISLIAFPSPYYSPAFTKGEKVDLNTKRTKK<br>SQHTSEGTYIHFQISGVTNTEKLPTPIELPLKVKVHG<br>KDSPLKYWPKFDKKQLAISTLDFEIRHQLTQIHGLY<br>RSSDKTGGYWKITMNDGSTYQSDLSKKFEYNTEKP<br>PINIDEIKTIEAEIN | 1 |
| Wild-type TSST-1 | MSTNDNIKDLLDWYSSGSDTFTNSEVLDNSLGSMRI<br>KNTDGSISLIIFPSPYYSPAFTKGEKVDLNTKRTKKS<br>QHTSEGTYIHFQISGVTNTEKLPTPIELPLKVKVHGK<br>DSPLKYWPKFDKKQLAISTLDFEIRHQLTQIHGLYR<br>SSDKIGGYWKITMNDGSTYQSDLSKKFEYNTEKPPI<br>NIDEIKTIEAEIN | 9 |
| SEB$_{L45R/Y89A/Y94A}$<br>(Mutations<br>bold/underlined) | MESQPDPKPDELHKSSKFTGLMENMKVLYDDNHV<br>SAINVKSIDQFRYFDLIYSIKDTKLGNYDNVRVEFK<br>NKDLADKYKDKYVDVFGANAYYQCAFSKKTNDIN<br>SHQTDKRKTCMYGGVTEHNGNQLDKYRSITVRVFE<br>DGKNLLSFDVQTNKKKVTAQELDYLTRHYLVKNK<br>KLYEFNNSPYETGYIKFIENENSFWYDMMPAPGDK<br>FDQSKYLMMYNDNKMVDSKDVKIEVYLTTKKK | 2 |
| Wild-type SEB | MESQPDPKPDELHKSSKFTGLMENMKVLYDDNHV<br>SAINVKSIDQFLYFDLIYSIKDTKLGNYDNVRVEFK<br>NKDLADKYKDKYVDVFGANYYYQCYFSKKTNDIN<br>SHQTDKRKTCMYGGVTEHNGNQLDKYRSITVRVFE<br>DGKNLLSFDVQTNKKKVTAQELDYLTRHYLVKNK<br>KLYEFNNSPYETGYIKFIENENSFWYDMMPAPDK<br>FDQSKYTMMYNDNKMVDSKDVKIEVYLTTKKK | 10 |
| SEA$_{H225A}$<br>(Mutation<br>bold/underlined) | EKSEEINEKDLRKKSELQGTALGNLKQIYYYNEKA<br>KTENKESHDQFLQHTILFKGFFTDHSWYNDLLVDF<br>DSKDIVDKYKGKKVDLYGAYYGYQCAGGTPNKTA<br>CMYGGVTLHDNNRLTEEKKVPINLWLDGKQNTVP<br>LETVKTNKKNVTVQELDLQARRYLQEKYNLYNSD<br>VFDGKVQRGLIVFHTSTEPSVNYDLFGAQGQYSNT<br>LLRIYRDNKTINSENMAIDIYLYTS | 11 |
| SEA$_{L48R/D70R/Y92A}$<br>(Mutations<br>bold/underlined | EKSEEINEKDLRKKSELQGTALGNLKQIYYYNEKA<br>KTENKESHDQFRQHTILFKGFFTDHSWYNDLLVRF<br>DSKDIVDKYKGKKVDLYGAYAGYQCAGGTPNKTA<br>CMYGGVTLHDNNRLTEEKKVPINLWLDGKQNTVP<br>LETVKTNKKNVTVQELDLQARRYLQEKYNLYNSD<br>VFDGKVQRGLIVFHTSTFPSVNYDLFGAQGQYSNT<br>LLRIYRDNKTINSENMAIDIYLYTS | 3 |
| SEA$_{L48R/D70R/Y92A/H225A}$<br>(Mutations<br>bold/underlined) | EKSEEINEKDLRKKSELQGTALGNLKQIYYYNEKA<br>KTENKESHDQFRQHTILFKGFFTDHSWYNDLLVRF<br>DSKDIVDKYKGKKVDLYGAYAGYQCAGGTPNKTA<br>CMYGGVTLHDNNRLTEEKKVPINLWLDGKQNTVP<br>LETVKTNKKNVTVQELDLQARRYLQEKYNLYNSD<br>VFDGKVQRGLIVFHSTEPSVNVDLEGAQGQVSNT<br>LLRIYRDNKTINSENMAIDIYLYTS | 4 |
| Wild-type SEA | EKSEEINEKDLRKKSELQGTALGNLKQIYVYNEKA<br>KTENKESHDQFLQHTILFKGFFTDHSWYNDLLVDF<br>DSKDIVDKVKGKKVDLYGAYYGYQCAGGTPNKTA<br>CMYGGVTLHDNNRLTEEKKVPINLWLDGKQNTVP<br>LETVKTNKKNVTVQELDLQARRYLQEKYNLYNSD<br>VFDGKVQRGLIVFHTSTEPSVNYDLFGAQGQYSNT<br>LLRIYRDNKTINSENMHIDIYLYTS | 12 |

TABLE 1-continued

| SAgs and Multivalent Oligopeptide Protein Sequences | | SEQ ID NO |
|---|---|---|
| rTBA Fusion Protein:<br>TSST-1$_{L30R/D27A/I46A}$-<br>L-SEB$_{L45R/Y89A/Y94A}$-<br>L-SEA$_{L48R/D70R/Y92A}$<br>(Linkers underlined) | MSTNDNIKDLLDWYSSGSDTFTNSEVLANSRGSMRI<br>KNTDGSISLIAFPSPYYSPAFTKGEKVDLNTKRTKKS<br>QHTSEGTYIHFQISGVTNTEKLPTPIELPLKVKVHGK<br>DSPLKYWPKFDKKQLAISTLDFEIRHQLTQIHGLYR<br>SSDKTGGYWKITMNDGSTYQSDLSKKFEYNTEKPPI<br>NIDEIKTIEAEINGGGGSGGGGSGGGGSESQPDPKPD<br>ELHKSSKFTGLMENMKVLYDDNHVSAINVKSIDQF<br>RYFDLIYSIKDTKLGNYDNVRVEFKNKDLADKYKD<br>KYVDVFGANAYYQCAFSKKTNDINSHQTDKRKTC<br>MYGGVTEHNGNQLDKYRSITVRVFEDGKNLLSFDV<br>QTNKKKVTAQELDYLTRHYLVKNKKLYEFNNSPY<br>ETGYIKFIENENSFWYDMMPAPGDKFDQSKYLMM<br>YNDNKMVDSKDVKIEVYLTTKKKGGGGSGGGGSG<br>GGGSEKSEEINEKDLRKKSELQGTALGNLKQIYYYN<br>EKAKTENKESHDQFRQHTILFKGFFTDHSWYNDLL<br>VRFDSKDIVDKYKGKKVDLYGAYAGYQCAGGTPN<br>KTACMYGGVTLHDNNRLTEEKKVPINLWLDGKQN<br>TVPLETVKTNKKNVTVQELDLQARRYLQEKVNLY<br>NSDVFDGKVQRGLIVFHTSTEPSVNYDLFGAQGQY<br>SNTLLRIYRDNKTINSENMHIDIYLYTS | 5 |
| rTBA225 Fusion<br>Protein:<br>TSST-1$_{L30R/D27A/I46A}$-<br>L-SEB$_{L45R/Y89A/Y94A}$-<br>L-SEA$_{L48R/D70R/Y92A/H225A}$<br>(Linkers underlined) | MSTNDNIKDLLDWYSSGSDTFTNSEVLANSRGSMRI<br>KNTDGSISLIAFTSPYYSPAFTKGEKVDLNTKRTKKS<br>QHTSEGTYIHFQISGVTNTEKLPTPIELPLKVKVHGK<br>DSPLKYWPKFDKKQLAISTLDFEIRHQLTQIHGLYR<br>SSDKTGGYWKITMNDGSTYQSDLSKKFEYNTEKPPI<br>NIDEIKTIEAEINGGGGSGGGGSGGGGSESQPDPKPD<br>ELHKSSKFTGLMENMKVLYDDNHVSAINVKSIDQF<br>RYFDLIYSIKDTKLGNYDNVRVEFKNKDLADKYKD<br>KYVDVFGANAYYQCAFSKKTNDINSHQTDKRKTC<br>MYGGVTEHNGNQLDKYRSITVRVFEDGKNLLSFDV<br>QTNKKKVTAQELDYLTRHYLVKNKKLYEFNNSPY<br>ETGYIKFIENENSFWYDMMPAPGDKFDQSKYLMM<br>YNDNKMVDSKDVKIEVYLTTKKKGGGGSGGGGSG<br>GGGSEKSEEINEKDLRKKSELQGTALGNLKQIYYYN<br>EKAKTENKESHDQFRQHTILFKGFFTDHSWYNDLL<br>VRFDSKDIVDKYKGKKVDLYGAYAGYQCAGGTPN<br>KTACMYGGVTLHDNNRLTEEKKVPINLWLDGKQN<br>TVPLETVKTNKKNVTVQELDTQARRYLQEKYNLY<br>NSDVFDGKVQRGLIVFHTSTEPSVNYDLFGAQGQY<br>SNTLLRIYRDNKTINSENMAIDIYLYTS | 6 |

In another aspect, the multivalent oligopeptide and/or SAg toxoid as provided herein can be attached to a heterologous polypeptide. Various heterologous polypeptides can be used, including, but not limited to an N- or C-terminal peptide imparting stabilization, secretion, or simplified purification, such as a hexa-Histidine-tag, a ubiquitin tag, a NusA tag, a chitin binding domain, ompT, ompA, pelB, DsbA, DsbC, c-myc, KSI, polyaspartic acid, (Ala-Trp-Trp-Pro)n, polyphenylalanine, polycysteine, polyarginine, a B-tag, a HSB-tag, green fluorescent protein (GFP), influenza virus hemagglutinin (HAI), a calmodulin binding protein (CBP), a galactose-binding protein, a maltose binding protein (MBP), a cellulose binding domains (CBD's), dihydrofolate reductase (DHFR), glutathione-S-transferase (GST), streptococcal protein G, staphylococcal protein A, T7gene10, an avidin/streptavidin/Strep-tag complex, trpE, chloramphenicol acetyltransferase, lacZ (β-Galactosidase), His-patch thioredoxin, thioredoxin, a FLAG™ peptide (Sigma-Aldrich), an S-tag, or a T7-tag. See, e.g., Stevens, R. C., Structure, 8:R177-R185 (2000). Heterologous polypeptides can also include any pre- and/or pro-sequences that facilitate the transport, translocations, processing and/or purification of a multivalent oligopeptide and/or SAg toxoid as described herein from a host cell or any useful immunogenic sequence, including but not limited to sequences that encode a T-cell epitope of a microbial pathogen, or other immunogenic proteins and/or epitopes.

In some aspects, the multivalent oligopeptide and/or SAg toxoid attached to a heterologous polypeptide, as described herein, can include a peptide linker sequence joining sequences that comprise two or more peptide regions. Suitable peptide linker sequences can be chosen based on their ability to adopt a flexible, extended conformation, or a secondary structure that could interact with joined epitopes, or based on their ability to increase overall solubility of the fusion polypeptide, or based on their lack of electrostatic or water-interaction effects that influence joined peptide regions.

In some aspects, the multivalent oligopeptide and/or SAg toxoid as described herein, is isolated. An "isolated" polypeptide is one that has been removed from its natural milieu. The term "isolated" does not connote any particular level of purification. Recombinantly produced multivalent oligopeptides and/or SAgs as described herein, expressed in non-native host cells is considered isolated for purposes of the disclosure, as is the polypeptide which have been separated, fractionated, or partially or substantially purified by any suitable technique, including by filtration, chromatography, centrifugation, and the like.

As provided for herein, the production of multivalent oligopeptides and/or SAgs as described herein, can be achieved by culturing a host cell comprising a polynucleotide that operably encodes a polypeptide of the disclosure, and recovering the polypeptide. Determining conditions for culturing such a host cell and expressing the polynucleotide are generally specific to the host cell and the expression system and are within the knowledge of one of skill in the art. Likewise, appropriate methods for recovering the polypeptide of the disclosure are known to those in the art, and include, but are not limited to, chromatography, filtration, precipitation, or centrifugation.

III. Polynucleotides

Also provided by this disclosure is an isolated polynucleotide comprising a nucleic acid encoding a multivalent oligopeptide and/or SAg toxoid as described elsewhere herein. In certain aspects, an isolated polynucleotide as provided herein further comprises non-coding regions such as promoters, operators, or transcription terminators as described elsewhere herein. In some aspects, the disclosure is directed to the polynucleotide as described herein, and further comprising a heterologous nucleic acid. The heterologous nucleic acid can, in some aspects, encode a heterologous polypeptide fused to the polypeptide as described herein. For example, the isolated polynucleotide as described herein can comprise additional coding regions encoding, e.g., a heterologous polypeptide fused to the polypeptide as described herein, or coding regions encoding heterologous polypeptides separate from the polypeptide as described herein such as, but not limited to, selectable markers, additional immunogens, immune enhancers, and the like.

Also provided are expression constructs, vectors, and/or host cells comprising the polynucleotides described herein. An example of an isolated polynucleotide is a recombinant polynucleotide contained in a vector. In certain aspects, the vector is an expression vector. Further examples of an isolated polynucleotide include recombinant polynucleotides maintained in heterologous host cells or purified (partially or substantially) polynucleotides in solution. In certain aspects of the disclosure a polynucleotide is "recombinant." Isolated polynucleotides or nucleic acids according to the disclosure further include such molecules produced synthetically. The relative degree of purity of a polynucleotide or polypeptide described herein is easily determined by well-known methods.

Also included within the scope of the disclosure are genetically engineered polynucleotides encoding the multivalent oligopeptides and/or SAgs as described herein. Modifications of nucleic acids encoding the multivalent oligopeptides and/or SAgs as described herein can readily be accomplished by those skilled in the art, for example, by oligonucleotide-directed site-specific mutagenesis or de novo nucleic acid synthesis.

Some aspects disclose an isolated polynucleotide comprising a nucleic acid that encodes a multivalent oligopeptide and/or SAg toxoid as described elsewhere herein, where the coding region encoding the polypeptide has been codon-optimized. As appreciated by one of ordinary skill m the art, various nucleic acid coding regions will encode the same polypeptide due to the redundancy of the genetic code. Deviations in the nucleotide sequence that comprise the codons encoding the amino acids of any polypeptide chain allow for variations in the sequence of the coding region. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 2. As a result, many amino acids are designated by more than one codon. For example, the amino acids alanine and proline are coded for by four triplets, serine and arginine by six, whereas tryptophan and methionine are coded by just one triplet. This degeneracy allows for DNA base composition to vary over a wide range without altering the amino acid sequence of the polypeptides encoded by the DNA.

TABLE 2

The Standard Genetic Code

| | T | | C | | A | | G | |
|---|---|---|---|---|---|---|---|---|
| T | TTT Phe (F) | | TCT Ser (S) | | TAT Tyr (Y) | | TGT Cys (C) | |
| | TTC Phe (F) | | TCC Ser (S) | | TAC Tyr (Y) | | TGC Cys (C) | |
| | TTA Leu (L) | | TCA Ser (S) | | TAA Ter | | TGA Ter | |
| | TTG Leu (L) | | TCG Ser (S) | | TAG Ter | | TGG Trp (W) | |
| C | CTT Leu (L) | | CCT Pro (P) | | CAT His (H) | | CGT Arg (R) | |
| | CTC Leu (L) | | CCC Pro (P) | | CAC His (H) | | CGC Arg (R) | |
| | CTA Leu (L) | | CCA Pro (P) | | CAA Gln (Q) | | CGA Arg (R) | |
| | CTG Leu (L) | | CCG Pro (P) | | CAG Gln (Q) | | CGG Arg (R) | |
| A | ATT Ile (I) | | ACT Thr (T) | | AAT Asn (N) | | AGT Ser (S) | |
| | ATC Ile (I) | | ACC Thr (T) | | AAC Asn (N) | | AGC Ser (S) | |
| | ATA Ile (I) | | ACA Thr (T) | | AAA Lys (K) | | AGA Arg (R) | |
| | ATG Met (M) | | ACG Thr (T) | | AAG Lys (K) | | AGG Arg (R) | |
| G | GTT Val (V) | | GCT Ala (A) | | GAT Asp (D) | | GGT Gly (G) | |
| | GTC Val (V) | | GCC Ala (A) | | GAC Asp (D) | | GGC Gly (G) | |
| | GTA Val (V) | | GCA Ala (A) | | GAA Glu (E) | | GGA Gly (G) | |
| | GTG Val (V) | | GCG Ala (A) | | GAG Glu (E) | | GGG Gly (G) | |

It is to be appreciated that any polynucleotide that encodes a polypeptide in accordance with the disclosure falls within the scope of this disclosure, regardless of the codons used.

Many organisms display a bias for use of particular codons to code for insertion of a particular amino acid in a growing polypeptide chain. Codon preference or codon bias, differences in codon usage between organisms, is afforded by degeneracy of the genetic code, and is well documented among many organisms.

Different factors have been proposed to contribute to codon usage preference, including translational selection, GC composition, strand-specific mutational bias, amino acid conservation, protein hydropathy, transcriptional selection and even RNA stability. One factor that determines codon usage is mutational bias that shapes genome GC composition. This factor is most significant in genomes with extreme base composition: species with high GC content (e.g., gram positive bacteria). Mutational bias is responsible not only for intergenetic difference in codon usage but also for codon usage bias within the same genome (Ermolaeva M, Curr. Issues Mol. Biol. 3(4):91-97, 2001).

Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

The present disclosure provides a polynucleotide comprising a codon-optimized coding region which encodes a multivalent oligopeptide and/or SAg toxoid as described herein. The codon usage is adapted for optimized expression in a given prokaryotic or eukaryotic host cell. In certain aspects the codon usage is adapted for optimized expression in *E. coli*.

For example, SEQ ID NO: 7 is a nucleotide sequence codon optimized for *E. coli* expression encoding the rTBA fusion protein:

(SEQ ID NO: 7)
atgtcgacgaatgacaacatcaaagacctgctggactggtactcctcggg ctcggatacgttcacgaatagcgaagtgctggcaaactcacgcggtagca tgcgtatcaaaaataccgatggtagcattagcctgatcgcttttccgtca ccgtattacagcccggcattcaccaaaggcgaaaaagtggatctgaatac caaacgcacgaaaaaatcacagcatacctcagaaggtacctacatccact ttcagatcagcggcgtgaccaacaccgaaaaactgccgaccccgattgaa ctgccgctgaaagtgaaagttcatggcaaagattcgccgctgaaatattg gccgaaatttgataaaaaacagctggcaatttcgaccctggatttcgaaa ttcgccaccagctgacccagatccatggtctgtaccgttcaagcgacaaa accggcggttattggaaaatcaccatgaatgatggttcgacgtaccagag cgatctgtcgaaaaaattcgaatacaacacggaaaaaccgccgattaata tcgatgaaatcaaaaccatcgaagcggaaatcaatggcggtggcggctcg ggtggtggcggtagcggtggcggcggtagtgaatcgcaaccggatccgaa accggacgaactgcacaaatcgtccaaatttaccggtctgatggaaaata tgaaagtgctgtatgatgacaaccatgtgtcggcaattaacgtgaaaagc atcgatcagtttcgctatttcgatctgatctatagcattaaagatacgaa actgggtaattacgataacgttcgtgtggaatttaaaaacaaagatctgg cggacaaatataaagacaaatacgtggacgttttcggtgcgaatgcgtat taccaatgcgcctttagcaaaaagaccaatgatatcaactcccatcagac cgacaaacgtaaaacctgcatgtacggtggtgtgaccgaacataacggta atcagctggacaaatatcgtagcatcacggtccgtgtgtttgaagacggc aaaaacctgctgtcatttgatgttcagacgaacaaaaagaaagttacggc tcaagaactggattacctgacccgccactatctggtgaaaaataaaaaac tgtacgaatttaacaatagcccgtacgaaaccggctacatcaaattcatt gaaaatgaaaatagctttggtacgatatgatgccggcaccgggtgacaa atttgaccaaagcaaatacctgatgatgtacaacgataacaaaatggtcg attcaaaagacgtgaaaatcgaagtctatctgacgaccaaaaagaaaggt ggcggtggttctggtggtggtggctcgggcggcggtggctcggaaaaatc cgaagaaattaacgaaaaagacctgcgtaaaaaatccgaactgcagggta cggcgctggtaatctgaaacagatttattactacaacgaaaaagccaaa accgaaaacaaagaaagccatgatcagttccgccagcatacgatcctgtt caaaggcttttcaccgatcattcgtggtataatgacctgctggtgcgtt tcgatagcaaagacattgtggataaatataaaggcaaaaagtggatctg tatgcgcatacgctggttatcagtgtgcgggcggtacgccgaataaaac ggcatgcatgtatggtggtgtgacgctgcatgacaataaccgcctgaccg aagaaagaaagtgccgattaatctgtggctggacggtaaacagaacacc gtgccgctggaaacggtgaaaaccaataaaaagaacgtgaccgtgcagga actggacctgcaagcacgccgttatctgcaggaaaaatataacctgtata acagcgacgtgtcgatggcaaagtgcagcgtggtctgatcgtcttccata ccagcaccgaaccgagcgttaactatgacctgtttggcgcacaaggccag tactccaatacccctgctgcgcatttatcgcgataacaaaaccattaactc cgaaaacatgCACattgacatttacctgtacacctcgtaacatcatcacc atcattgataataa For example, SEQ ID NO: 8 is a nucleotide sequence codon optimized for *E. coli* expression encoding the rTBA225 fusion protein:

(SEQ ID NO: 8)
atgtcgacgaatgacaacatcaaagacctgctggactggtactcctcggg ctcggatacgttcacgaatagcgaagtgctggcaaactcacgcggtagca tgcgtatcaaaaataccgatggtagcattagcctgatcgcttttccgtca ccgtattacagcccggcattcaccaaaggcgaaaaagtggatctgaatac caaacgcacgaaaaaatcacagcatacctcagaaggtacctacatccact ttcagatcagcggcgtgaccaacaccgaaaaactgccgaccccgattgaa ctgccgctgaaagtgaaagttcatggcaaagattcgccgctgaaatattg gccgaaatttgataaaaaacagctggcaatttcgaccctggatttcgaaa ttcgccacccagctgacccagatccatggtctgtaccgttcaagcgacaa aaccggcggttattggaaaatcaccatgaatgatggttcgacgtaccaga gcgatctgtcgaaaaaattcgaatacaacacggaaaaaccgccgattaat atcgatgaaatcaaaaccatcgaagcggaaatcaatggcggtggcggctc gggtggtggcggtagcggtggcggcggtagtgaatcgcaaccggatccga aaccggacgaactgcacaaatcgtccaaatttaccggtctgatggaaaat atgaaagtgctgtatgatgacaaccatgtgtcggcaattaacgtgaaaag catcgatcagtttcgctatttcgatctgatctatagcattaaagatacga aactgggtaattacgataacgttcgtgtggaatttaaaaacaaagatctg gcggacaaatataaagacaaatacgtggacgttttcggtgcgaatgcgta ttaccaatgcgcctttagcaaaaagaccaatgatatcaactcccatcaga ccgacaaacgtaaaacctgcatgtacggtggtgtgaccgaacataacggt aatcagctggacaaatatcgtagcatcacggtccgtgtgtttgaagacgg caaaaacctgctgtcatttgatgttcagacgaacaaaaagaaagttacgg ctcaagaactggattacctgacccgccactatctggtgaaaaataaaaaa ctgtacgaatttaacaatagcccgtacgaaaccggctacatcaaattcat tgaaaatgaaaatagctttggtacgatatgatgccggcaccgggtgaca aatttgaccaaagcaaatacctgatgatgtacaacgataacaaaatggtc gattcaaaagacgtgaaaatcgaagtctatctgacgaccaaaaagaaagg tggcggtggttctggtggtggtggctcgggcggcggtggctcggaaaaat ccgaagaaattaacgaaaaagacctgcgtaaaaaatccgaactgcagggt -continued

```
acggcgctgggtaatctgaaacagatttattactacaacgaaaaagccaa aaccgaaaacaaagaaagccatgatcagttccgccagcatacgatcctgt tcaaaggcttttcaccgatcattcgtggtataatgacctgctggtgcgt ttcgatagcaaagacattgtggataaatataaaggcaaaaaagtggatct gtatggcgcatacgctggttatcagtgtgcgggcggtacgccgaataaaa cggcatgcatgtatggtggtgtgacgctgcatgacaataaccgcctgacc gaagaaaagaaagtgccgattaatctgtggctggacggtaaacagaacac cgtgccgctggaaacggtgaaaaccaataaaaagaacgtgaccgtgcagg aactggacctgcaagcacgccgttatctgcaggaaaaatataacctgtat aacagcgacgtgttcgatggcaaagtgcagcgtggtctgatcgtcttcca taccagcaccgaaccgagcgttaactatgacctgtttggcgcacaaggcc agtactccaatacctgctgcgcatttatcgcgataacaaaaccattaac tccgaaaacatgGCCattgacatttacctgtacacctcgtaacatcatca ccatcattgataataa
```

Codon-optimized polynucleotides are prepared by incorporating codons preferred for use in the genes of a given species into the DNA sequence. Also provided are polynucleotide expression constructs, vectors, host cells comprising polynucleotides comprising codon-optimized coding regions which encode a multivalent oligopeptide and/or SAg toxoid as described herein.

Given the large number of gene sequences available for a wide variety of animal, plant and microbial species, it is possible to calculate the relative frequencies of codon usage. Codon usage tables are readily available, for example, at the "Codon Usage Database" available at http://www.kazusa.or.jp/codon/ (visited Oct. 12, 2011), and these tables can be adapted in a number of ways. (Nakamura, Y., et. al., "Codon usage tabulated from the international DNA sequence databases: status for foe year 2000" *Nucl. Acids Res.* 28:292, 2000).

By utilizing available tables, one of ordinary skill in the art can apply the frequencies to any given polypeptide sequence, and produce a nucleic acid fragment of a codon-optimized coding region which encodes a desired polypeptide, but which uses codons optimal for a given species. A number of options are available for synthesizing codon optimized coding regions designed by any of the methods described above, using standard and routine molecular biological manipulations well known to those of ordinary skill in the art. In addition, gene synthesis is readily available commercially.

IV. Vectors and Expression Systems

Further provided is a vector comprising a polynucleotide as provided herein. The term "vector," as used herein, refers to e.g., any of a number of nucleic acids into which a desired sequence con be inserted, e.g., by restriction and ligation, for transport between different genetic environments or for expression in a host cell. Nucleic acid vectors can be DNA or RNA. Vectors include, but are not limited to, plasmids, phage, phagemids, bacterial genomes, and virus genomes. A cloning vector is one which is able to replicate in a host cell, and which is further characterized by one or more endonuclease restriction sites at which the vector can be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host bacterium or just a single time per host before the host reproduces by mitosis. In the case of phage, replication can occur actively during a lytic phase or passively during a lysogenic phase. Certain vectors are capable of autonomous replication in a host cell into which they are introduced. Other vectors are integrated into the genome of a host cell upon introduction into the host cell, and thereby are replicated along with the host genome.

Any of a wide variety of suitable cloning vectors are known in the art and commercially available which can be used with appropriate hosts. As used herein, the term "plasmid" refers to a circular, double-stranded construct mode up of genetic material (i.e., nucleic acids), in which the genetic material is extrachromosomal and in some instances, replicates autonomously. A polynucleotide described herein can be in a circular or linearized plasmid or in any other sort of vector. Procedures for insetting a nucleotide sequence into a vector, e.g., an expression vector, and transforming or transfecting into an appropriate host cell and cultivating under conditions suitable for expression are generally known in the art.

The disclosure further provides a vector comprising a nucleic acid sequence encoding a multivalent oligopeptide and/or SAg toxoid as described elsewhere herein. In certain aspects the vector is an expression vector capable of expressing the multivalent oligopeptide and/or SAg toxoid as described herein in a suitable host cell. The term "expression vector" refers to a vector that is capable of expressing the polypeptide described herein, i.e., the vector sequence contains the regulatory sequences regulating transcription and translation of a polypeptide, including, but not limited to promoters, operators, transcription termination sites, ribosome binding sites, and the like. The term "expression" refers to the biological production of a product encoded by a coding sequence. In most cases a DNA sequence, including the coding sequence, is transcribed to form a messenger-RNA (mRNA). The messenger-RNA is then translated to form a polypeptide product which has a relevant biological activity. Also, the process of expression can involve further processing steps to the RNA product of transcription, such as splicing to remove introns, and/or post-translational processing of a polypeptide product.

Vector-host systems include, but are not limited to, systems such as bacterial, mammalian, yeast, insect or plant cell systems, either in vivo, e.g., in an animal or in vitro, e.g., in bacteria or in cell cultures. The selection of an appropriate host is deemed to be within the scope of those skilled in the art from the teachings herein. In certain aspects, the host cell is a bacterium, and insect cell, a mammalian cell, or a plant cell. In certain aspects, the bacterium is *E. coli*.

Host cells are genetically engineered (infected, transduced, transformed, or transfected) with vectors of the disclosure. Thus, one aspect of the disclosure is directed to a host cell comprising a vector which contains the polynucleotide as describe herein. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan. The term "transfect," as used herein, refers to any procedure whereby eukaryotic cells are induced to accept and incorporate into their genome isolated DNA, including but not limited to DNA in the form of a plasmid. The term "transform," as used herein, refers to any procedure whereby bacterial cells are induced to accept and incorporate into their genome isolated DNA, including but not limited to DNA in the form of a plasmid.

Bacterial host-expression vector systems include, but are not limited to, a prokaryote (e.g., E. coli), transformed with recombinant bacteriophage DNA, plasmid DNA or cosmid DNA. In some aspects, the plasmids used with E. coli use the T7 promoter-driven system regulated by the LacI protein via IPTG induction. A large number of suitable vectors are known to those of skill in the art, and are commercially available. The following bacterial vectors are provided by way of example: pET (Novagen), pET28, pBAD, pTrcHIS, pBR322, pQE70, pQE60, pQE-9 (Qiagen), phagescript, psiX174, pBluescript SK, pbsks, pNH8A, pNH16a, pNH18A, pNH46A (Stratagene), ptrc99a, pKK223-3, pKK243-3, pDR540, pBR322, pPS10, RSF1010, pRIT5 (Pharmacia); pCR (Invitrogen); pLex (Invitrogen), and pUC plasmid derivatives.

A suitable expression vector contains regulatory sequences that can be operably joined to an inserted nucleotide sequence encoding the multivalent oligopeptide and/or SAg toxoid as described herein. As used herein, the term "regulatory sequences" means nucleotide sequences which are necessary for or conducive to the transcription of an inserted sequence encoding a multivalent oligopeptide and/or SAg toxoid as described herein by a host cell and/or which are necessary for or conducive to the translation by a host cell of the resulting transcript into the desired multivalent oligopeptide and/or SAg toxoid. Regulatory sequences include, but are not limited to, 5' sequences such as operators, promoters and ribosome binding sequences, and 3' sequences such as polyadenylation signals or transcription terminators. Regulatory sequences can also include enhancer sequences or upstream activator sequences.

Generally, bacterial vectors will include origins of replication and selectable markers, e.g., the ampicillin, tetracycline, kanamycin, resistance genes of E. coli, permitting transformation of the host cell and a promoter derived from a highly-expressed gene to direct transcription of a downstream structural sequence. Suitable promoters include, but are not limited to, the T7 promoter, lambda (λ) promoter, T5 promoter, and lac promoter, or promoters derived from operons encoding glycolytic enzymes such as 3-phosphoglycerate kinase (PGK), acid phosphatase, or heat shock proteins, or inducible promoters like cadmium (pcad), and beta-lactamase (pbla).

Once an expression vector is selected, the polynucleotide as described herein can be cloned downstream of the promoter, for example, in a polylinker region. The vector is transformed into an appropriate bacterial strain, and DNA is prepared using standard techniques. The orientation and DNA sequence of the polynucleotide as well as all other elements included in the vector, are continued using restriction mapping, DNA sequence analysis, and/or PCR analysis. Bacterial cells harboring the correct plasmid can be stored as cell banks.

V. Immunogenic and Pharmaceutical Compositions

Further disclosed are compositions, e.g., immunogenic or pharmaceutical compositions that contain an effective amount of the multivalent oligopeptide and/or SAg toxoid as described herein, or a polynucleotide encoding the polypeptide of the disclosure. Compositions as described herein can further comprise additional immunogenic components, e.g., as a multivalent vaccine, as well as carriers, excipients or adjuvants.

Compositions as provided herein can be formulated according to known methods. Suitable preparation methods are described, for example, in *Remington's Pharmaceutical Sciences*, 19th Edition, A. R. Gennaro, ed., Mack Publishing Co., Easton, Pa. (1995), which is incorporated herein by reference in its entirety. Composition can be in a variety of forms, including, but not limited to an aqueous solution, an emulsion, a gel, a suspension, lyophilized form, or any other form known in the art. In addition, the composition can contain pharmaceutically acceptable additives including, for example, diluents, binders, stabilizers, and preservatives. Once formulated, compositions of the disclosure can be administered directly to the subject. The subjects to be treated can be animals; in particular, human subjects can be treated.

Carriers that can be used with compositions of the disclosure are well known in the art, and include, without limitation, e.g., thyroglobulin, albumins such as human serum albumin, tetanus toxoid, and polyamino acids such as poly L-lysine, poly L-glutamic acid, influenza, hepatitis B virus core protein, and the like. A variety of aqueous carriers can be used, e.g., water, buffered water, 0.8% saline, 0.3% glycine, hyaluronic acid and the like. Compositions can be sterilized by conventional, well known sterilization techniques, or can be sterile filtered. A resulting composition can be packaged for use as is, or lyophilized, the lyophilized preparation being combined with a sterile solution prior to administration. Compositions can contain pharmaceutically acceptable auxiliary substances as to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamineoleate, etc.

Certain compositions as provided herein further include one or more adjuvants, a substance added to an immunogenic composition to, for example, enhance, sustain, localize, or modulate an immune response to an immunogen. The term "adjuvant" refers to any material having the ability to (1) alter or increase the immune response to a particular antigen or (2) increase or aid an effect of a pharmacological agent. Any compound which can increase the expression, antigenicity or immunogenicity of the polypeptide is a potential adjuvant. The term "immunogenic carrier" as used herein refers to a first moiety, e.g., a polypeptide or fragment, variant, or derivative thereof which enhances the immunogenicity of a second polypeptide or fragment, variant, or derivative thereof.

A great variety of materials have been shown to have adjuvant activity through a variety of mechanisms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant can also alter or modulate an immune response, for example, by changing a primarily humoral or $Th_2$ response into a primarily cellular, or $Th_1$ response. Immune responses to a given antigen can be tested by various immunoassays well known to those of ordinary skill in the art, and/or described elsewhere herein.

A wide number of adjuvants are familiar to persons of ordinary skill in the art, and are described in numerous references. Adjuvants which can be used in compositions described herein include, but are not limited to: inert carriers, such as alum, bentonite, latex, and acrylic particles; incomplete Freund's adjuvant, complete Freund's adjuvant; aluminum-based salts such as aluminum hydroxide; Alhydrogel (Al(OH$_3$)); aluminum phosphate (AlPO$_4$); calcium-based salts; silica; any TLR biological ligand(s); IDC-1001 (also known as GLA-SE; glucopyranosyl lipid adjuvant stable emulsion) (Coler et al., PLoS One. 2010. 5(10): p. e13677; Coler et al., PLoS One, 2011. 6(1): p. e16333); CpG (Mullen et al., PLoS One, 2008. 3(8): p. e2940), or any combination thereof. In certain aspects, the adjuvant comprises Alhydrogel. The amount of adjuvant, how it is formulated, and how it is administered all parameters which are well within the purview of a person of ordinary skill in the art.

In some aspects, a composition of the disclosure further comprises a liposome or other particulate carrier, which can serve, e.g., to stabilize a formulation, to target the formulation to a particular tissue, such as lymphoid tissue, or to increase the half-life of the polypeptide composition. Such particulate carriers include emulsions, foams, micelles, insoluble monolayers, liquid crystals, phospholipid dispersions, lamellar layers, iscoms, and the like. In these preparations, the polypeptide described herein can be incorporated as part of a liposome or other particle, or can be delivered in conjunction with a liposome. Liposomes for use in accordance with the disclosure can be formed from standard vesicle-forming lipids, which generally include neutral and negatively charged phospholipids and a sterol, such as cholesterol. A composition comprising a liposome or other particulate suspension as well as the polypeptide as described herein can be administered intravenously, locally, topically, etc. in a dose which varies according to, inter alia, the manner of administration, the polypeptide being delivered, and the stage of the disease being treated.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, the polypeptide as described herein, often at a concentration of 25%-75%.

For aerosol or mucosal administration, the polypeptide as described herein can be supplied in finely divided form, optionally along with a surfactant and, propellant and/or a mucoadhesive, e.g., chitosan. In certain aspects, the surfactant is pharmaceutically acceptable, and in some aspects soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1%-20% by weight of the composition, in some aspects 0.25-5% by weight. The balance of the composition is ordinarily propellant, although an atomizer can be used in which no propellant is necessary and other percentages are adjusted accordingly. In some aspects, the immunogenic polypeptides can be incorporated within an aerodynamically light particle, such as those particles described in U.S. Pat. No. 6,942,868 or U.S. Pat. Pub. No. 2005/0008633. A carrier can also be included, e.g., lecithin for intranasal delivery.

The disclosure is also directed to a method of producing the composition according to the disclosure. In some aspects, the method of producing the composition comprises (a) isolating a polypeptide according to the disclosure; and (b) adding an adjuvant, carrier and/or excipient to the isolated polypeptide. Some aspects disclose further combining the polypeptide with other staphylococcal antigens.

Some aspects include a multivalent vaccine. A multivalent vaccine of the present disclosure can include a multivalent oligopeptide and/or SAg toxoid as described herein, or a polynucleotide encoding a multivalent oligopeptide and/or SAg toxoid, and one or more additional immunogenic components. Such components can be additional immunogens of the same infectious agent, e.g., *S. aureus*, or from other staphylococci, or can be immunogens derived from other infectious agents which can be effectively, conveniently, or economically administered together. In certain aspects, the multivalent oligopeptide and/or SAg toxoid as described herein, can be combined with other toxins or other virulent component-based vaccines to make a broad toxin-based multivalent vaccine capable of targeting multiple bacterial virulence determinants. In other aspects, the multivalent oligopeptide and/or SAg toxoid as described herein can be fused to other immunogenic, biologically significant, or protective epitope containing polypeptides to generate a multivalent vaccine in a single chain and induce an immune response against multiple antigens. In yet another aspect, the multivalent oligopeptide and/or SAg toxoid as described herein, can be fused to one or more T cell epitopes to induce T cell immunity.

VI. Methods of Treatment/Prevention and Regimens

Also provided is a method of treating or preventing *Staphylococcus* infection, e.g., *S. aureus* infection or treating or preventing a disease caused by *Staphylococcus*, e.g. *S. aureus* in a subject, comprising administering to a subject in need thereof a composition as described herein comprising a multivalent oligopeptide and/or SAg toxoid as described herein, or polynucleotides, vectors, or host cells encoding same. In certain aspects, the subject is an animal, e.g., a vertebrate, e.g., a mammal, e.g., a human. Some aspects include a method of inducing an immune response against a *S. aureus* strain, comprising administering to a subject in need of said immune response an effective amount of a composition comprising a multivalent oligopeptide and/or SAg toxoid as described herein, or polynucleotides, vectors, or host cells encoding same.

In some aspects, a subject is administered a composition comprising a multivalent oligopeptide and/or SAg toxoid as described herein, or polynucleotides, vectors, or host cells encoding same prophylactically, e.g., as a prophylactic vaccine, to establish or enhance immunity to *Staphylococcus*, e.g., *S. aureus*, in a healthy animal prior to potential or actual exposure to *Staphylococcus*, e.g., *S. aureus* or contraction of a *Staphylococcus*-related symptom, thus preventing disease, alleviating symptoms, reducing symptoms, or reducing the severity of disease symptoms. In one aspect the disease is a respiratory disease, e.g., pneumonia. Other diseases or conditions to be treated or prevented include, but are not limited to, bacteremia, sepsis, skin infections, wound infections, endocarditis, bone and joint infections, osteomyelitis, and/or meningitis. One or more compositions, polypeptides, polynucleotides, vectors, or host cells as described herein can also be used to treat a subject already exposed to *Staphylococcus*, e.g., *S. aureus*, or already suffering from a *Staphy-*

*lococcus* related symptom to further stimulate the immune system of the animal, thus reducing or eliminating the symptoms associated with that exposure. As defined herein, "treatment of an animal" refers to the use of one or more compositions, polypeptides, polynucleotides, vectors, or host cells of the disclosure to prevent, cure, retard, or reduce the severity of *S. aureus* symptoms in an animal and/or result in no worsening of *S. aureus* symptoms over a specified period of time, it is not required that any composition, polypeptide, polynucleotide, a vector, or a host cell as described herein provides total protection against a staphylococcal infection or totally cure or eliminate all *Staphylococcus* related symptoms.

As used herein, "a subject in need of therapeutic and/or preventative immunity" refers to a subject in which it is desirable to treat, i.e., to prevent, cure, retard, or reduce the severity of *Staphylococcus* related symptoms, or result in no worsening of *Staphylococcus* related symptoms over a specified period of time. As used herein, "a subject in need of the immune response" refers to a subject for which an immune response(s) against a *Staphylococcus* related disease is desired.

Treatment with pharmaceutical compositions comprising an immunogenic composition, polypeptide or polynucleotide as described herein can occur separately or in conjunction with other treatments, as appropriate.

In therapeutic applications, a composition, polypeptide or polynucleotide of the disclosure is administered to a patient in an amount sufficient to elicit an effective innate, humoral and/or cellular response to the multivalent oligopeptide and/or SAg toxoid to cure or at least partially arrest symptoms or complications.

An amount adequate to accomplish this is defined as "therapeutically effective dose" or "unit dose." Amounts effective for this use will depend on, e.g., the polypeptide or polynucleotide composition, the manner of administration, the stage and severity of the disease being treated, the weight and general state of health of the patient, and the judgment of the prescribing physician. In some aspects, a priming dose is followed by a boosting dose over a period of time.

In some aspects, generally for humans, an initial immunization (that is for therapeutic or prophylactic administration) is administered followed by boosting dosages in the same dose range pursuant to a boosting regimen over weeks to months depending upon the patient's response and condition by measuring the antibody or T lymphocyte response in the patient's blood.

Polypeptides and compositions as described herein can generally be employed in serious disease states, that is, life-threatening or potentially life threatening situations. In such cases, in view of the minimization of extraneous substances and the relative nontoxic nature of the polypeptides, it is possible and can be felt desirable by the treating physician to administer substantial excesses of these polypeptide compositions.

For therapeutic use, administration can begin at the first sign of *S. aureus* infection or risk factors. In certain aspects, the initial dose is followed by boosting doses until, e.g., symptoms are substantially abated and for a period thereafter. In frequent infection, loading doses followed by boosting doses can be indicated.

In certain aspects, the composition as described herein is delivered to a subject by methods described herein, thereby achieving an effective immune response, and/or an effective therapeutic or preventative immune response. Any mode of administration can be used so long as the mode results in the delivery and/or expression of the desired polypeptide in the desired tissue, in an amount sufficient to generate an immune response to *Staphylococcus*, e.g., *S. aureus*, and/or to generate a prophylactically or therapeutically effective immune response to *Staphylococcus*, e.g., to *S. aureus*, in an animal in need of such response. According to the disclosed methods, a composition described herein can be administered by mucosal delivery, transdermal delivery, subcutaneous injection, intravenous injection, oral administration, pulmonary administration, intramuscular (i.m.) administration, or via intraperitoneal injection. Other suitable routes of administration include, but not limited to intratracheal, transdermal, intraocular, intranasal, inhalation, intracavity, intraductal (e.g., into the pancreas) and intraparenchymal (i.e., into any tissue) administration. Transdermal delivery includes, but not limited to intradermal (e.g., into the dermis or epidermis), transdermal (e.g., percutaneous) and transmucosal administration (i.e., into or through skin or mucosal tissue). Intracavity administration includes, but not limited to administration into oral, vaginal, rectal, nasal, peritoneal, or intestinal cavities as well as, intrathecal (i.e., into spinal canal), intraventricular (i.e., into the brain ventricles or the heart ventricles), intra-arterial (i.e., into the heart atrium) and sub arachnoidal (i.e., into the sub arachnoid spaces of the brain) administration.

Any mode of administration can be used so long as the mode results in the delivery and/or expression of the desired polypeptide in an amount sufficient to generate an immune response to *Staphylococcus*, e.g., *S. aureus*, and/or to generate a prophylactically or therapeutically effective immune response to *Staphylococcus*, e.g., *S. aureus*, in an animal in need of such response. Administration as described herein can be by e.g., needle injection, or other delivery or devices known in the art.

In some aspects, a composition comprising a multivalent oligopeptide and/or SAg toxoid as described herein, or polynucleotides, vectors, or host cells encoding same, stimulate an antibody response or a cell-mediated immune response sufficient for protection of an animal against *Staphylococcus*, e.g., *S. aureus* infection. In other aspects, a composition comprising a multivalent oligopeptide and/or SAg toxoid as described herein, or polynucleotides, vectors, or host cells encoding same, stimulate both a humoral and a cell-mediated response, the combination of which is sufficient for protection of an animal against *Staphylococcus*, e.g., *S. aureus* infection. In some aspects, a composition comprising a multivalent oligopeptide and/or SAg toxoid as described herein, or polynucleotides, vectors, or host cells encoding same, further stimulates an innate, an antibody, and/or a cellular immune response.

In some aspects, a composition comprising a multivalent oligopeptide and/or SAg toxoid as described herein, or polynucleotides, vectors, or host cells encoding same, can induce antibody responses to *S. aureus*. In certain aspects, components that induce T cell responses (e.g., T cell epitopes) are combined with components such as the polypeptides as described herein that primarily induce an antibody response.

Further disclosed is a method for generating, enhancing, or modulating a protective and/or therapeutic immune response to *S. aureus* infection in a subject, comprising administering to a subject in need of therapeutic and/or preventative immunity one or more of the compositions as described herein.

The compositions as described herein can be administered to an animal at any time during the lifecycle of the animal to which it is being administered. In humans, administration of the composition as described herein can, and often advantageously occurs while other vaccines are being administered, e.g., as a multivalent vaccine as described elsewhere herein.

Furthermore, the composition as described herein can be used in any desired immunization or administration regimen; e.g., in a single administration or alternatively as part of periodic vaccination regimes such as annual vaccinations, or as in a prime-boost regime in which composition or polypeptide or polynucleotide of the disclosure is administered either before or after the administration of the same or of a different polypeptide or polynucleotide. Recent studies have indicated that a prime-boost protocol is often a suitable method of administering vaccines. In a prime-boost protocol, one or more compositions as described herein can be utilized in a "prime boost" regimen. An example of a "prime boost" regimen can be found in Yang, Z. et al. *J. Virol.* 77:799-803, 2002, which is incorporated herein by reference in its entirety.

Infections to be treated include, but are not limited to a localized or systemic infection of skin, soft tissue, blood, or an organ or an auto-immune disease. Specific diseases or conditions to be treated or prevented include, but are not limited to, respiratory diseases, e.g., pneumonia, sepsis, skin infections, wound infections, endocarditis, bone and joint infections, osteomyelitis, and/or meningitis.

A number of animal models for *S. aureus* infection are known in the art, and can be used with the methods disclosed herein without undue experimentation. For example, a hamster model of methicillin-resistant *Staphylococcus aureus* (MRSA) pneumonia has been described for the testing of antimicrobials. (Verghese A. et al., *Chemotherapy.* 34:497-503 (1988), Kephart P A. et al. *J Antimicrob Chemother.* 21:33-9, (1988)). Further, a model of *S. aureus*-induced pneumonia in adult, immunocompetent C57BL/6J mice is described, which closely mimics the clinical and pathological features of pneumonia in human patients. (Bubeck-Wardenburg J. et al., *Infect Immun.* 75:1040-4 (2007)). Additionally, virulence has been tested in a rat model of *S. aureus* pneumonia as described in McElroy et al. (McElroy M C. et al., *Infect Immun.* 67:5541-4 (1999)). Finally, a standardized and reproducible model of MRSA-induced septic pneumonia to evaluate new therapies was established in sheep. (Enkhbaatar P. et al., *Shock.* 29(5):642-9 (2008)).

The practice of the disclosure will employ, unless otherwise indicated, conventional techniques of cell biology, cell culture, molecular biology, transgenic biology, microbiology, recombinant DNA, and immunology, which are within the skill of the art. Such techniques are explained folly in the literature. See, for example. Molecular Cloning A Laboratory Manual, 2nd Ed., Sambrook et al., ed., Cold Spring Harbor Laboratory Press: (1989); Molecular Cloning: A Laboratory Manual, Sambrook et al., ed., Cold Springs Harbor Laboratory, New York (1992), DNA Cloning, D. N. Glover ed., Volumes I and II (1985); Oligonucleotide Synthesis. M. J. Gait ed., (1984); Mull et al. U.S. Pat. No. 4,683,195; Nucleic Acid Hybridization, B. D. Hames & S. J. Higgins eds. (1984); Transcription And Translation, B. D. Hames & S. J. Higgins eds. (1984); Culture Of Animal Cells, R. Freshney, Alan R. Liss, Inc., (1987); Immobilized Cells And Enzymes, IRL Press, (1986); B. Perbal, A Practical Guide To Molecular Cloning (1984); the treatise, Methods In Enzymology, Academic Press, Inc., N.Y.; Gene Transfer Vectors For Mammalian Cells, J. H. Miller and M. P. Calos eds., Cold Spring Harbor laboratory (1987); Methods In Enzymology. Vols. 154 and 155 (Wu et al. eds.); Immunochemical Methods In Cell And Molecular Biology, Mayer and Walker, eds., Academic Press, London (1987); Handbook Of Experimental Immunology, Volumes I-IV, D. M. Weir and C. C. Blackwell, eds., (1986); Manipulating the Mouse Embryo, Cold Spring Harbor Laboratory Press, Cold Spring Harbor, N.Y., (1986); and in Ausubel et al., Current Protocols in Molecular Biology, John Wiley and Sons, Baltimore, Md. (1989).

Standard reference works setting forth general principles of immunology include Current Protocols in Immunology, John Wiley & Sons, New York; Klein, J., Immunology: The Science of Self-Nonself Discrimination. John Wiley & Sons, New York (1982); Roitt, T., Brostoff, J. and Male D., Immunology, 6$^{th}$ ed. London: Mosby (2001); Abbas A., Abul, A. and Lichtman, A., Cellular and Molecular Immunology, Ed. 5, Elsevier Health Sciences Division (2005); and Harlow and Lane, Antibodies: A Laboratory Manual, Cold Spring Harbor Press (1988).

EXAMPLES

The breadth and scope of the present disclosure should not be limited by any of the above-described exemplary aspects or embodiments, but should be defined only in accordance with the following claims and their equivalents.

Example 1: rTBA225 Triple Fusion of Staphylococcal Superantigen Toxoids

While the safety of rSEB has been extensively evaluated including a phase I clinical trial, the safety of rSEA and rTSST-1 have not been extensively studied. In addition, to evaluate whether the fusion of the three superantigen toxoids exacerbate residual superantigenic activity, the response of PBMC from healthy human donors to rTBA using IFNγ release as readout for superantigenic activity was evaluated ("PBMC stimulation assay").

For the PBMC stimulation assay, PBMC were incubated in culture medium in individual wells of 96 well plates with various concentration of wild type TSST-1 or toxoids such as rTBA at 37° C. and 5% $CO_2$ in a humidified incubator. After 48 hours of culture, the plates were centrifuged for 5 minutes and supernatants removed. The IFNγ concentration in each well was measured using an ELISA kit from R&D Systems according to manufacturer's instructions. The concentration of induced IFNγ was plotted against the concentration of the toxin or toxoid to determine $EC_{50}$ (50 percent effective concentration) for each agent.

Three donors characterized as low, medium, and high responders were used. As shown in FIG. 4, at high concentrations, rTBA exhibited low Level of IFN-γ induction in the low responder, medium level in medium responder and high levels in high responders, although these responses were much lower than the responses of the same donor to wild-type superantigens.

These experiments suggested that rTBA retains some residual superantigenic activity. Further analysis indicated that this activity is due to residual activity of rSEAL48R/D70R/Y92A, while rTSSTL30R/D27A/146A was completely inactive. Therefore, an additional mutation was introduced into the rSEA portion of rTBA. A previous report suggested that mutation of H22S (SEA-H225A) binding site for MHC class 11 reduced the ability of SEA to stimulate T cells (Hudson et al., 1995, Journal/J Exp Med. 182(3):711-720; Kozono et al., 1995, Journal/Immunity, 3(2): 187-196). A mutation was introduced at position H225A into WT SEA, rSEAL48R/D70R/Y92A as well as rTBA. The new mutants are referred to herein as SEAH225A (SEQ ID NO: 11), rSEAVax225 (also as SEAL48R/D70R/Y92A/H225A)

(SEQ ID NO: 4), and rTBA225 (SEQ ID NO: 6), respectively, and were tested in the PBMC stimulation assay. Introduction of the single H225A mutation into wild-type SEA (SEAH225A) attenuated the toxin but left significant levels of residual toxicity (FIG. 4). The combination of H225A and the L48R/D70R/Y92A mutations (rSEAVax225), however, was completely inactive on low and medium responder cells and only marginally active on high responder cells at very high concentration (FIG. 4). Similarly, rTBA showed residual toxicity while rTBA225 was completely attenuated, even more so than rSFAVax225. These data indicate that a combination of these four mutations was required for full attenuation of rTBA and rSEAVax (FIG. 4).

Example 2: Method for Production and Tag-Free Purification of Fusion Protein of Superantigen Mutants The genes encoding the fusion of toxoids rTBA (SEQ ID NO: 5) and rTBA225 (SEQ ID NO: 6) were codon optimized, synthesized, cloned into the pET24a (+) expression vector, and transformed into BL21(DE3) E. coli cells. Overnight cultures were expanded in Luria Broth containing kanamycin until a mid-log phase culture (~0.5 OD at 600 nm), at which point the cells were chilled to ~25° C. and induced with 0.3 mM IPTG, followed by overnight culture at 25° C. The next day, the bacterial cells were harvested, weighed, and resuspended in cell lysis buffer (20 mM Tris pH 8.0, 50 mM NaCl, 1 mM EDTA, 0.1% Triton X-100). Lysozyme was added (1 mg/mL), and the cells were incubated at 37° C. for 30 minutes. The partially lysed cells were sonicated. Bacterial cell lysis was confirmed spectrophotometrically. The cell lysate was adjusted to 0.5 M NaCl, and the nucleic acid was precipitated by the addition of polyethyleneimine (PEI) under constant mixing. The PEI pellet was removed by centrifugation, and the supernatant containing the toxoid was subjected to ammonium sulfate (($NH_4)_2SO_4$) precipitation. The $(NH_4)_2SO_4$ pellet was recovered by centrifugation and stored at −80° C.

As shown in FIG. 2A, the following chromatography steps were performed. The $(NH_4)_2SO_4$ pellets were resuspended and desalted into the capture column equilibration buffer, clarified, and subjected to chromatography over a Poros 50 HS column. The column was equilibrated, loaded, washed and eluted using a 40-column volume (CV) gradient from 25 to 1,000 mM NaCl in phosphate buffer at pH 6.5. The column fractions were analyzed by SDS-PAGE to determine the toxoid containing fractions. The pooled material was dialyzed into the next column equilibration buffer and subjected to chromatography over a BioRad Ceramic Hydroxyapatite (HTP) Type I column. The column was equilibrated, loaded, washed and eluted using a 40 CV gradient of 50-1,000 mM NaCl in a phosphate buffer at pH 6.8. The fractions were analyzed by SDS-PAGE to detect the toxoid (FIG. 2B). The pooled HTP fractions were dialyzed into the appropriate storage buffer, filter sterilized, aliquoted and frozen at −80° C.

Example 3: Immunogenicity of the Fusion Construct rTBA

Groups of 5 BALB/c mice were immunized, 3 times with 14 day interval, with either rTBA or a cocktail of the three toxoids along with Sigma Adjuvant System (SAS) adjuvant. Day 35 sera from these mice were tested for total antibody ELISA and toxin neutralization (TNA) titers.

Peripheral blood mononuclear cells (PBMC) were isolated from heparinized blood of Healthy human donors by Ficoll gradient centrifugation. Isolated PBMCs were resuspended in RPMI 1640 with 5% fetal bovine serum (PBS), cells were washed, enumerated by Trypan blue exclusion and adjusted to $2\times10^6$ cells/ml. 75 µl of this cell suspension ($1.5\times10^5$ cells) with a viability of >95% was added to duplicate wells of 96-well flat-bottom plates containing 37.5 µl of semi-log diluted sera from vaccinated animals mixed with a fixed concentration of the superantigen. Wells containing medium with toxin only were used as controls. The cultures were incubated at 37° C. in an atmosphere of 5% $CO_2$-95% air for 48 hours. Cells were centrifuged at 1600×g for 10 minutes, culture supernatants were harvested and IFNγ production was assessed by ELISA (R&D Systems, Minneapolis, Minn.) following the manufacturers' protocol. Plates were read at 450 run using the VersaMax plate reader and data was transferred and analyzed in Microsoft Office Excel 2007. Cells stimulated with toxin in the absence of a neutralizing antibodies served as positive control and was considered as 0% IFNγ inhibition. Accordingly, inhibition of IFNγ production in the presence of immune sera was calculated as the difference between positive control and sample. $TC_{50}$ values for the neutralizing agents (human monoclonal antibodies) were determined using a 4-parameter logistic model (equation 205, XLFit v5.2).

rTBA induced much higher titers of total IgG binding to SEB and TSST-1 as well as higher toxin neutralization (TNA) titers as compared to the cocktail of the three toxoids (FIG. 3A). Thus, the fusion of the three toxoids into one molecule not only simplifies the vaccine, but also enhances the immunogenicity.

The immunogenicity of rTBA formulated in Alhydrogel or CpG was also compared. As shown in FIG. 3B, both adjuvants induced very high and balanced titers against all three toxins and the magnitude of antibody response was higher than those achieved with SAS adjuvant. The two adjuvants were equivalent with respect to induction of neutralizing antibodies against SEB and TSST-1 while Alhydrogel induced stronger neutralizing response against SEA.

Example 4: Immunogenicity of Fusion Construct rTBA225

The immunogenicity of rTBA22S was tested in Balb/c mice in comparison to rTBA to determine whether the additional mutation impacted the immunogenicity. Mice were immunized three times with 20 µg either of SAg cocktail (equimolar amounts of each individual toxoid), rTBA or rTBA225 along with Alhydrogel. After the third immunization, mouse sera were tested for binding and neutralization titers by ELISAs and toxin neutralization assay (TNA) for the antigens SEA, SEB and TSST-1. As shown in FIG. 5, mice vaccinated with the fusion constructs bad a strong total antibody (FIG. 5A) and neutralizing antibody response (FIG. 5B) to ail three superantigens. These data show that addition of the mutation did not reduce the immunogenicity of the fusion vaccine. Furthermore, the fusion protein rTBA225 is able to induce neutralizing activity towards superantigens that are not included in the antigen as shown in FIG. 5C.

It was observed that the SAg toxoid cocktail formulated in Alhydrogel was unable to induce any antibody response to TSST-1, while in sharp contrast, the fusion proteins rTBA and rTBA225 induced strong TSST-1 response (FIG. 5A left panel). These data show that fusion of TSST-1 was necessary for inducing strong immune response when formulated with Alhydrogel. The binding data indicated that this is due to inability of TSST-1 alone to adsorb Alhydrogel, while as a fusion protein the antigen adsorbs the Alhydrogel and therefore can induce strong antibody response (FIG. 6).

Example 5: Protective Efficacy of rTBA225 Vaccine Against Toxin Challenge with SEA, SEB, and TSST-1

The protective efficacy of rTBA225 against SAg toxin challenge was evaluated by immunizing Balb/c mice with 20 µg of rTBA225 thrice along with Alhydrogel as the adjuvant followed by challenge with an intraperitoneal lethal dose of SEA (10 µg/mouse), SEB (3.315 µg/mouse) or TSST-1 (10 µg/mouse) potentiated by 40 µg/mouse LPS. Weights and health scores of the mice were monitored for five days after the challenge. As shown in FIG. 7, immunization with rTBA225 provided 100% protection to SEB and TSST-1 challenge and 90% protection to SEA challenge. These data demonstrate the protective efficacy of rTBA225 against challenge with the respective toxins.

What is claimed is:

1. An attenuated *Staphylococcus aureus*-derived superantigen (SAg) SEA toxoid comprising an amino acid sequence that is at least 95% identical to SEQ ID NO: 4, wherein the toxoid comprises the four mutations relative to wild-type SEA corresponding to the L48R, D70R, Y92A, and H225A mutations; and wherein the toxoid has decreased superantigenic activity and/or is less virulent than a SEA toxoid comprising SEQ ID NO: 3.

2. The attenuated SEA toxoid of claim 1 comprising an amino acid sequence at least 97% identical to SEQ ID NO: 4.

3. The attenuated SEA toxoid of claim 1 comprising SEQ ID NO: 4.

4. The attenuated SEA toxoid of claim 1, which has less than 50% of the superantigenic activity of a SEA toxoid comprising SEQ ID NO: 3.

5. A multivalent oligopeptide comprising a fusion of two or more attenuated *Staphylococcus aureus*-derived superantigen (SAg) toxoids arranged in any order, wherein the SAg toxoids can be the same or different, and wherein at least one of the SAg toxoids is the SEA toxoid of claim 1.

6. The oligopeptide of claim 5, wherein the oligopeptide has decreased superantigenic activity and/or is less virulent than a SAg fusion protein comprising SEQ ID NO: 5.

7. The oligopeptide of claim 5, wherein the oligopeptide has less than 50% of the superantigenic activity of a SAg fusion protein comprising SEQ ID NO: 5.

8. The oligopeptide of claim 5, wherein the oligopeptide is completely attenuated.

9. The oligopeptide of claim 5, comprising three or more SAg toxoids.

10. The oligopeptide of claim 5, comprising one or more of a staphylococcal toxic shock syndrome toxin-1 (TSST-1) attenuated toxoid; a staphylococcal enterotoxin B (SEB) attenuated toxoid; or any combination thereof.

11. The oligopeptide of claim 10, wherein the TSST-1 attenuated toxoid comprises three mutations relative to wild-type TSST-1 corresponding to the L30R, D27A, and I46A mutations and an amino acid sequence at least 95% identical to SEQ ID NO: 1; the SEB attenuated toxoid comprises three mutations relative to wild-type SEB corresponding to the L45R, Y89A, and Y94A mutations and an amino acid sequence at least 95% identical to SEQ ID NO: 2; and the SEA attenuated toxoid comprises four mutations relative to wild-type SEA corresponding to the L48R, D70R, Y92A, and H225A mutations and an amino acid sequence at least 95% identical to SEQ ID NO: 4.

12. The oligopeptide of claim 10, wherein the TSST-1 toxoid comprises the amino acid sequence SEQ ID NO: 1; the SEB toxoid comprises the amino acid sequence SEQ ID NO: 2; and the SEA attenuated toxoid comprises the amino acid sequence SEQ ID NO: 4.

13. The oligopeptide of claim 5, wherein the two or more SAg toxoids are each associated via a linker.

14. The oligopeptide of claim 13, wherein the linker comprises (GGGS)$_n$ (SEQ ID NO: 13) or (GGGGS)$_n$ (SEQ ID NO: 14), wherein n is a integer from 1 to 10.

15. The oligopeptide of claim 5 comprising the amino acid sequence SEQ ID NO: 6.

16. The oligopeptide of claim 5, further comprising a heterologous polypeptide.

17. The oligopeptide of claim 16, wherein the heterologous polypeptide comprises an immunogen, a T-cell epitope, a B-cell epitope, a fragment thereof, or a combination thereof.

18. A composition comprising the attenuated SEA toxoid of claim 1 and a carrier.

19. The composition of claim 18, further comprising an adjuvant.

20. The composition of claim 18, further comprising an additional immunogen.

21. The composition of claim 20, wherein the additional immunogen is a bacterial antigen selected from the group consisting of a pore forming toxin or a fragment thereof, a superantigen or a fragment thereof, a cell surface protein or a fragment thereof, and a combination of two or more of the bacterial antigens.

22. A composition comprising the multivalent oligopeptide of claim 5 and a carrier.

23. The composition of claim 22, further comprising an adjuvant.

24. The composition of claim 22, further comprising an additional immunogen.

25. The composition of claim 24, wherein the additional immunogen is a bacterial antigen.

26. The composition of claim 25, wherein the bacterial antigen is selected from the group consisting of a pore forming toxin or a fragment thereof, a superantigen or a fragment thereof, a cell surface protein or a fragment thereof, and a combination of two or more of the bacterial antigens.

27. A method of producing a vaccine against *S. aureus* infection, the method comprising isolating the attenuated SEA toxoid of claim 1 and combining the toxoid with an adjuvant.

28. A method of producing a vaccine against *S. aureus* infection, the method comprising isolating the multivalent oligopeptide of claim 5 and combining the oligopeptide with an adjuvant.

29. A method of inducing a host immune response against *Staphylococcus aureus*, comprising administering to a subject in need of the immune response an effective amount of the composition of claim 18.

30. The method of claim 29, wherein the composition is administered via intramuscular injection, intradermal injection, intraperitoneal injection, subcutaneous injection, intravenous injection, oral administration, mucosal administration, intranasal administration, or pulmonary administration.

31. A method of preventing or treating a Staphylococcal disease or infection in a subject comprising administering to a subject in need thereof the composition of claim 18.

32. The method of claim 31, wherein the infection is a localized or systemic infection of skin, soft tissue, blood, or an organ, or is auto-immune in nature.

33. The method of claim 31, wherein the disease is a respiratory disease.

34. The method of claim 33, wherein the respiratory disease is pneumonia.

35. The method of claim 31, wherein the disease is sepsis.

36. The method of claim 35, wherein the subject is a human.

37. A method of inducing a host immune response against *Staphylococcus aureus*, comprising administering to a subject in need of the immune response an effective amount of the composition of claim 22.

38. A method of preventing or treating a Staphylococcal disease or infection in a subject comprising administering to a subject in need thereof the composition of claim 22.

39. The method of claim 38, wherein the infection is a localized or systemic infection of skin, soft tissue, blood, or an organ, or is auto-immune in nature.

40. The method of claim 38, wherein the disease is a respiratory disease.

41. The method of claim 40, wherein the respiratory disease is pneumonia.

42. The method of claim 38, wherein the disease is sepsis.

43. The method of claim 38, wherein the subject is a human.

44. The method of claim 38, wherein the composition is administered via intramuscular injection, intradermal injection, intraperitoneal injection, subcutaneous injection, intravenous injection, oral administration, mucosal administration, intranasal administration, or pulmonary administration.

* * * * *

UNITED STATES PATENT AND TRADEMARK OFFICE
CERTIFICATE OF CORRECTION

PATENT NO. : 11,260,120 B2
APPLICATION NO. : 16/633664
DATED : March 1, 2022
INVENTOR(S) : Mohammad Javad Aman et al.

It is certified that error appears in the above-identified patent and that said Letters Patent is hereby corrected as shown below:

In the Specification

Replace SEQ ID NO: 4 in Table 1 in Column 17 with the text in the attachment

Signed and Sealed this
Twenty-seventh Day of December, 2022

Katherine Kelly Vidal
*Director of the United States Patent and Trademark Office*

TABLE 1

SAgs and Multivalent Oligopeptide Protein Sequences

| | | SEQ ID NO |
|---|---|---|
| TSST-1<sub>L30R/D27A/I46A</sub> (Mutations relative to wild-type bold/underlined) | MSTNDNIKDLLDWYSSGSDTFTNSEVLANSRGSMRIKNTDGSI SLIAFPSPYYSPAFTKGEKVDLNTKRTKKSQHTSEGTYIHFQIS GVTNTEKLPTPIELPLKVKVHGKDSPLKYWPKFDKKQLAISTLD FEIRHQLTQIHGLYRSSDKTGGYWKITMNDGSTYQSDLSKKFE YNTEKPPINIDEIKTIEAEIN | 1 |
| Wild-type TSST-1 | MSTNDNIKDLLDWYSSGSDTFTNSEVLDNSLGSMRIKNTDGSI SLIIFPSPYYSPAFTKGEKVDLNTKRTKKSQHTSEGTYIHFQISG VTNTEKLPTPIELPLKVKVHGKDSPLKYWPKFDKKQLAISTLDF EIRHQLTQIHGLYRSSDKTGGYWKITMNDGSTYQSDLSKKFEY NTEKPPINIDEIKTIEAEIN | 9 |
| SEB<sub>L45R/Y89A/Y94A</sub> (Mutations bold/underlined) | MESQPDPKPDELHKSSKFTGLMENMKVLYDDNHVSAINVKSID QFRYFDLIYSIKDTKLGNYDNVRVEFKNKDLADKYKDKYVDVF GANAYYQCAFSKKTNDINSHQTDKRKTCMYGGVTEHNGNQL DKYRSITVRVFEDGKNLLSFDVQTNKKKVTAQELDYLTRHYLV KNKKLYEFNNSPYETGYIKFIENENSFWYDMMPAPGDKFDQS KYLMMYNDNKMVDSKDVKIEVYLTTKKK | 2 |
| Wild-type SEB | MESQPDPKPDELHKSSKFTGLMENMKVLYDDNHVSAINVKSID QFLYFDLIYSIKDTKLGNYDNVRVEFKNKDLADKYKDKYVDVFG ANYYYQCYFSKKTNDINSHQTDKRKTCMYGGVTEHNGNQLDK YRSITVRVFEDGKNLLSFDVQTNKKKVTAQELDYLTRHYLVKN KKLYEFNNSPYETGYIKFIENENSFWYDMMPAPGDKFDQSKYL MMYNDNKMVDSKDVKIEVYLTTKKK | 10 |
| SEA<sub>H225A</sub> (Mutation bold/underlined) | EKSEEINEKDLRKKSELQGTALGNLKQIYYYNEKAKTENKESH DQFLQHTILFKGFFTDHSWYNDLLVDFDSKDIVDKYKGKKVDL YGAYYGYQCAGGTPNKTACMYGGVTLHDNNRLTEEKKVPINL WLDGKQNTVPLETVKTNKKNVTVQELDLQARRYLQEKYNLYN SDVFDGKVQRGLIVFHTSTEPSVNYDLFGAQGQYSNTLLRIYR DNKTINSENMAIDIYLYTS | 11 |
| SEA<sub>L48R/D70R/Y92A</sub> (Mutations bold/underlined) | EKSEEINEKDLRKKSELQGTALGNLKQIYYYNEKAKTENKESH DQFRQHTILFKGFFTDHSWYNDLLVRFDSKDIVDKYKGKKVDL YGAYAGYQCAGGTPNKTACMYGGVTLHDNNRLTEEKKVPINL WLDGKQNTVPLETVKTNKKNVTVQELDLQARRYLQEKYNLYN SDVFDGKVQRGLIVFHTSTEPSVNYDLFGAQGQYSNTLLRIYR DNKTINSENMHIDIYLYTS | 3 |
| SEA<sub>L48R/D70R/Y92A/H225A</sub> (Mutations bold/underlined) | EKSEEINEKDLRKKSELQGTALGNLKQIYYYNEKAKTENKESH DQFRQHTILFKGFFTDHSWYNDLLVRFDSKDIVDKYKGKKVDL YGAYAGYQCAGGTPNKTACMYGGVTLHDNNRLTEEKKVPINL WLDGKQNTVPLETVKTNKKNVTVQELDLQARRYLQEKYNLYN SDVFDGKVQRGLIVFHTSTEPSVNYDLFGAQGQYSNTLLRIYR DNKTINSENMAIDIYLYTS | 4 |
| Wild-type SEA | EKSEEINEKDLRKKSELQGTALGNLKQIYYYNEKAKTENKESH DQFLQHTILFKGFFTDHSWYNDLLVDFDSKDIVDKYKGKKVDL YGAYYGYQCAGGTPNKTACMYGGVTLHDNNRLTEEKKVPINL WLDGKQNTVPLETVKTNKKNVTVQELDLQARRYLQEKYNLYN SDVFDGKVQRGLIVFHTSTEPSVNYDLFGAQGQYSNTLLRIYR DNKTINSENMHIDIYLYTS | 12 |

SEQUENCE LISTING

```
<160> NUMBER OF SEQ ID NOS: 15

<210> SEQ ID NO 1
<211> LENGTH: 195
<212> TYPE: PRT
<213> ORGANISM: Staphylococcus aureus
<220> FEATURE:
<221> NAME/KEY: SIMILAR
<222> LOCATION: (1)..(195)
<223> OTHER INFORMATION: TSST-1 L30R / D27A / I46A

<400> SEQUENCE: 1

Met Ser Thr Asn Asp Asn Ile Lys Asp Leu Leu Asp Trp Tyr Ser Ser
1               5                   10                  15

Gly Ser Asp Thr Phe Thr Asn Ser Glu Val Leu Ala Asn Ser Arg Gly
            20                  25                  30

Ser Met Arg Ile Lys Asn Thr Asp Gly Ser Ile Ser Leu Ile Ala Phe
        35                  40                  45

Pro Ser Pro Tyr Tyr Ser Pro Ala Phe Thr Lys Gly Glu Lys Val Asp
    50                  55                  60

Leu Asn Thr Lys Arg Thr Lys Lys Ser Gln His Thr Ser Glu Gly Thr
65                  70                  75                  80

Tyr Ile His Phe Gln Ile Ser Gly Val Thr Asn Thr Glu Lys Leu Pro
                85                  90                  95

Thr Pro Ile Glu Leu Pro Leu Lys Val Lys Val His Gly Lys Asp Ser
            100                 105                 110

Pro Leu Lys Tyr Trp Pro Lys Phe Asp Lys Lys Gln Leu Ala Ile Ser
        115                 120                 125

Thr Leu Asp Phe Glu Ile Arg His Gln Leu Thr Gln Ile His Gly Leu
    130                 135                 140

Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Lys Phe Glu Tyr Asn
                165                 170                 175

Thr Glu Lys Pro Pro Ile Asn Ile Asp Glu Ile Lys Thr Ile Glu Ala
            180                 185                 190

Glu Ile Asn
        195

<210> SEQ ID NO 2
<211> LENGTH: 240
<212> TYPE: PRT
<213> ORGANISM: Staphylococcus aureus
<220> FEATURE:
<221> NAME/KEY: SIMILAR
<222> LOCATION: (1)..(240)
<223> OTHER INFORMATION: SEB L45R / Y89A / Y94A

<400> SEQUENCE: 2
```

```
Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
            20                  25                  30

His Val Ser Ala Ile Asn Val Lys Ser Ile Asp Gln Phe Arg Tyr Phe
            35                  40                  45

Asp Leu Ile Tyr Ser Ile Lys Asp Thr Lys Leu Gly Asn Tyr Asp Asn
50                  55                  60

Val Arg Val Glu Phe Lys Asn Lys Asp Leu Ala Asp Lys Tyr Lys Asp
65                  70                  75                  80

Lys Tyr Val Asp Val Phe Gly Ala Asn Ala Tyr Tyr Gln Cys Ala Phe
            85                  90                  95

Ser Lys Lys Thr Asn Asp Ile Asn Ser His Gln Thr Asp Lys Arg Lys
            100                 105                 110

Thr Cys Met Tyr Gly Gly Val Thr Glu His Asn Gly Asn Gln Leu Asp
            115                 120                 125

Lys Tyr Arg Ser Ile Thr Val Arg Val Phe Glu Asp Gly Lys Asn Leu
            130                 135                 140

Leu Ser Phe Asp Val Gln Thr Asn Lys Lys Val Thr Ala Gln Glu
145                 150                 155                 160

Leu Asp Tyr Leu Thr Arg His Tyr Leu Val Lys Asn Lys Lys Leu Tyr
                165                 170                 175

Glu Phe Asn Asn Ser Pro Tyr Glu Thr Gly Tyr Ile Lys Phe Ile Glu
            180                 185                 190

Asn Glu Asn Ser Phe Trp Tyr Asp Met Met Pro Ala Pro Gly Asp Lys
            195                 200                 205

Phe Asp Gln Ser Lys Tyr Leu Met Met Tyr Asn Asp Asn Lys Met Val
    210                 215                 220

Asp Ser Lys Asp Val Lys Ile Glu Val Tyr Leu Thr Thr Lys Lys
225                 230                 235                 240

<210> SEQ ID NO 3
<211> LENGTH: 232
<212> TYPE: PRT
<213> ORGANISM: Staphylococcus aureus
<220> FEATURE:
<221> NAME/KEY: SIMILAR
<222> LOCATION: (1)..(232)
<223> OTHER INFORMATION: SEA L48R / D70R / Y92A

<400> SEQUENCE:

```
                    115                 120                 125
Trp Leu Asp Gly Lys Gln Asn Thr Val Pro Leu Glu Thr Val Lys Thr
    130                 135                 140

Asn Lys Lys Asn Val Thr Val Gln Glu Leu Asp Leu Gln Ala Arg Arg
145                 150                 155                 160

Tyr Leu Gln Glu Lys Tyr Asn Leu Tyr Asn Ser Asp Val Phe Asp Gly
                165                 170                 175

Lys Val Gln Arg Gly Leu Ile Val Phe His Thr Ser Thr Glu Pro Ser
            180                 185                 190

Val Asn Tyr Asp Leu Phe Gly Ala Gln Gly Gln Tyr Ser Asn Thr Leu
        195                 200                 205

Leu Arg Ile Tyr Arg Asp Asn Lys Thr Ile Asn Ser Glu Asn Met His
    210                 215                 220

Ile Asp Ile Tyr Leu Tyr Thr Ser
225                 230

<210> SEQ ID NO 4
<211> LENGTH: 232
<212> TYPE: PRT
<213> ORGANISM: Staphylococcus aureus
<220> FEATURE:
<221> NAME/KEY: SIMILAR
<222> LOCATION: (1)..(232)
<223> OTHER INFORMATION: SEA L48R / D70R / Y92A / H225A

<400> SEQUENCE: 4

Glu Lys Ser Glu Glu Ile Asn Glu Lys Asp Leu Arg Lys Lys Ser Glu
1               5                   10                  15

Leu Gln Gly Thr Ala Leu Gly Asn Leu Lys Gln Ile Tyr Tyr Tyr Asn
                20                  25                  30

Glu Lys Ala Lys Thr Glu Asn Lys Glu Ser His Asp Gln Phe Arg Gln
            35                  40                  45

His Thr Ile Leu Phe Lys Gly Phe Phe Thr Asp His Ser Trp Tyr Asn
        50                  55                  60

Asp Leu Leu Val Arg Phe Asp Ser Lys Asp Ile Val Asp Lys Tyr Lys
65                  70                  75                  80

Gly Lys Lys Val Asp Leu Tyr Gly Ala Tyr Ala Gly Tyr Gln Cys Ala
                85                  90                  95

Gly Gly Thr Pro Asn Lys Thr Ala Cys Met Tyr Gly Gly Val Thr Leu
            100                 105                 110

His Asp Asn Asn Arg Leu Thr Glu Glu Lys Lys Val Pro Ile Asn Leu
        115                 120                 125

Trp Leu Asp Gly Lys Gln Asn Thr Val Pro Leu Glu Thr Val Lys Thr
    130                 135                 140

Asn Lys Lys Asn Val Thr Val Gln Glu Leu Asp Leu Gln Ala Arg Arg
145                 150                 155                 160

Tyr Leu Gln Glu Lys Tyr Asn Leu Tyr Asn Ser Asp Val Phe Asp Gly
                165                 170                 175

Lys Val Gln Arg Gly Leu Ile Val Phe His Thr Ser Thr Glu Pro Ser
            180                 185                 190

Val Asn Tyr Asp Leu Phe Gly Ala Gln Gly Gln Tyr Ser Asn Thr Leu
        195                 200                 205

Leu Arg Ile Tyr Arg Asp Asn Lys Thr Ile Asn Ser Glu Asn Met Ala
    210                 215                 220

Ile Asp Ile Tyr Leu Tyr Thr Ser
225                 230
```

<210> SEQ ID NO 5
<211> LENGTH: 696
<212> TYPE: PRT
<213> ORGANISM: Artificial Sequence
<220> FEATURE:
<223> OTHER INFORMATION: Synthetic

<400> SEQUENCE: 5

```
Met Ser Thr Asn Asp Asn Ile Lys Asp Leu Leu Asp Trp Tyr Ser Ser
1               5                   10                  15

Gly Ser Asp Thr Phe Thr Asn Ser Glu Val Leu Ala Asn Ser Arg Gly
            20                  25                  30

Ser Met Arg Ile Lys Asn Thr Asp Gly Ser Ile Ser Leu Ile Ala Phe
        35                  40                  45

Pro Ser Pro Tyr Tyr Ser Pro Ala Phe Thr Lys Gly Glu Lys Val Asp
    50                  55                  60

Leu Asn Thr Lys Arg Thr Lys Lys Ser Gln His Thr Ser Glu Gly Thr
65                  70                  75                  80

Tyr Ile His Phe Gln Ile Ser Gly Val Thr Asn Thr Glu Lys Leu Pro
                85                  90                  95

Thr Pro Ile Glu Leu Pro Leu Lys Val Lys Val His Gly Lys Asp Ser
            100                 105                 110

Pro Leu Lys Tyr Trp Pro Lys Phe Asp Lys Gln Leu Ala Ile Ser
        115                 120                 125

Thr Leu Asp Phe Glu Ile Arg His Gln Leu Thr Gln Ile His Gly Leu
    130                 135                 140

Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Lys Phe Glu Tyr Asn
                165                 170                 175

Thr Glu Lys Pro Pro Ile Asn Ile Asp Glu Ile Lys Thr Ile Glu Ala
            180                 185                 190

Glu Ile Asn Gly Gly Gly Gly Ser Gly Gly Gly Gly Ser Gly Gly Gly
        195                 200                 205

Gly Ser Glu Ser Gln Pro Asp Pro Lys Pro Asp Glu Leu His Lys Ser
    210                 215                 220

Ser Lys Phe Thr Gly Leu Met Glu Asn Met Lys Val Leu Tyr Asp Asp
225                 230                 235                 240

Asn His Val Ser Ala Ile Asn Val Lys Ser Ile Asp Gln Phe Arg Tyr
                245                 250                 255

Phe Asp Leu Ile Tyr Ser Ile Lys Asp Thr Lys Leu Gly Asn Tyr Asp
            260                 265                 270

Asn Val Arg Val Glu Phe Lys Asn Lys Asp Leu Ala Asp Lys Tyr Lys
        275                 280                 285

Asp Lys Tyr Val Asp Val Phe Gly Ala Asn Ala Tyr Tyr Gln Cys Ala
    290                 295                 300

Phe Ser Lys Lys Thr Asn Asp Ile Asn Ser His Gln Thr Asp Lys Arg
305                 310                 315                 320

Lys Thr Cys Met Tyr Gly Gly Val Thr Glu His Asn Gly Asn Gln Leu
                325                 330                 335

Asp Lys Tyr Arg Ser Ile Thr Val Arg Val Phe Glu Asp Gly Lys Asn
            340                 345                 350

Leu Leu Ser Phe Asp Val Gln Thr Asn Lys Lys Val Thr Ala Gln
        355                 360                 365
```

```
Glu Leu Asp Tyr Leu Thr Arg His Tyr Leu Val Lys Asn Lys Lys Leu
        370                 375                 380

Tyr Glu Phe Asn Asn Ser Pro Tyr Glu Thr Gly Tyr Ile Lys Phe Ile
385                 390                 395                 400

Glu Asn Glu Asn Ser Phe Trp Tyr Asp Met Met Pro Ala Pro Gly Asp
                405                 410                 415

Lys Phe Asp Gln Ser Lys Tyr Leu Met Met Tyr Asn Asp Asn Lys Met
            420                 425                 430

Val Asp Ser Lys Asp Val Lys Ile Glu Val Tyr Leu Thr Thr Lys Lys
        435                 440                 445

Lys Gly Gly Gly Ser Gly Gly Gly Ser Gly Gly Gly Ser
        450                 455                 460

Glu Lys Ser Glu Glu Ile Asn Glu Lys Asp Leu Arg Lys Lys Ser Glu
465                 470                 475                 480

Leu Gln Gly Thr Ala Leu Gly Asn Leu Lys Gln Ile Tyr Tyr Tyr Asn
                485                 490                 495

Glu Lys Ala Lys Thr Glu Asn Lys Glu Ser His Asp Gln Phe Arg Gln
            500                 505                 510

His Thr Ile Leu Phe Lys Gly Phe Phe Thr Asp His Ser Trp Tyr Asn
        515                 520                 525

Asp Leu Leu Val Arg Phe Asp Ser Lys Asp Ile Val Asp Lys Tyr Lys
530                 535                 540

Gly Lys Lys Val Asp Leu Tyr Gly Ala Tyr Ala Gly Tyr Gln Cys Ala
545                 550                 555                 560

Gly Gly Thr Pro Asn Lys Thr Ala Cys Met Tyr Gly Gly Val Thr Leu
                565                 570                 575

His Asp Asn Asn Arg Leu Thr Glu Glu Lys Lys Val Pro Ile Asn Leu
            580                 585                 590

Trp Leu Asp Gly Lys Gln Asn Thr Val Pro Leu Glu Thr Val Lys Thr
        595                 600                 605

Asn Lys Lys Asn Val Thr Val Gln Glu Leu Asp Leu Gln Ala Arg Arg
        610                 615                 620

Tyr Leu Gln Glu Lys Tyr Asn Leu Tyr Asn Ser Asp Val Phe Asp Gly
625                 630                 635                 640

Lys Val Gln Arg Gly Leu Ile Val Phe His Thr Ser Thr Glu Pro Ser
                645                 650                 655

Val Asn Tyr Asp Leu Phe Gly Ala Gln Gly Gln Tyr Ser Asn Thr Leu
            660                 665                 670

Leu Arg Ile Tyr Arg Asp Asn Lys Thr Ile Asn Ser Glu Asn Met His
        675                 680                 685

Ile Asp Ile Tyr Leu Tyr Thr Ser
        690                 695

<210> SEQ ID NO 6
<211> LENGTH: 696
<212> TYPE: PRT
<213> ORGANISM: Artificial Sequence
<220> FEATURE:
<223> OTHER INFORMATION: Synthetic

<400> SEQUENCE: 6

Met Ser Thr Asn Asp Asn Ile Lys Asp Leu Leu Asp Trp Tyr Ser Ser
1               5                   10                  15

Gly Ser Asp Thr Phe Thr Asn Ser Glu Val Leu Ala Asn Ser Arg Gly
            20                  25                  30
```

-continued

Ser Met Arg Ile Lys Asn Thr Asp Gly Ser Ile Ser Leu Ile Ala Phe
         35                  40                  45

Pro Ser Pro Tyr Tyr Ser Pro Ala Phe Thr Lys Gly Glu Lys Val Asp
 50                  55                  60

Leu Asn Thr Lys Arg Thr Lys Lys Ser Gln His Thr Ser Glu Gly Thr
 65                  70                  75                  80

Tyr Ile His Phe Gln Ile Ser Gly Val Thr Asn Thr Glu Lys Leu Pro
                 85                  90                  95

Thr Pro Ile Glu Leu Pro Leu Lys Val Lys Val His Gly Lys Asp Ser
                100                 105                 110

Pro Leu Lys Tyr Trp Pro Lys Phe Asp Lys Lys Gln Leu Ala Ile Ser
            115                 120                 125

Thr Leu Asp Phe Glu Ile Arg His Gln Leu Thr Gln Ile His Gly Leu
        130                 135                 140

Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Lys Phe Glu Tyr Asn
                165                 170                 175

Thr Glu Lys Pro Pro Ile Asn Ile Asp Glu Ile Lys Thr Ile Glu Ala
            180                 185                 190

Glu Ile Asn Gly Gly Gly Gly Ser Gly Gly Gly Gly Ser Gly Gly Gly
        195                 200                 205

Gly Ser Glu Ser Gln Pro Asp Pro Lys Pro Asp Glu Leu His Lys Ser
210                 215                 220

Ser Lys Phe Thr Gly Leu Met Glu Asn Met Lys Val Leu Tyr Asp Asp
225                 230                 235                 240

Asn His Val Ser Ala Ile Asn Val Lys Ser Ile Asp Gln Phe Arg Tyr
                245                 250                 255

Phe Asp Leu Ile Tyr Ser Ile Lys Asp Thr Lys Leu Gly Asn Tyr Asp
            260                 265                 270

Asn Val Arg Val Glu Phe Lys Asn Lys Asp Leu Ala Asp Lys Tyr Lys
        275                 280                 285

Asp Lys Tyr Val Asp Val Phe Gly Ala Asn Ala Tyr Tyr Gln Cys Ala
290                 295                 300

Phe Ser Lys Lys Thr Asn Asp Ile Asn Ser His Gln Thr Asp Lys Arg
305                 310                 315                 320

Lys Thr Cys Met Tyr Gly Gly Val Thr Glu His Asn Gly Asn Gln Leu
                325                 330                 335

Asp Lys Tyr Arg Ser Ile Thr Val Arg Val Phe Glu Asp Gly Lys Asn
            340                 345                 350

Leu Leu Ser Phe Asp Val Gln Thr Asn Lys Lys Val Thr Ala Gln
        355                 360                 365

Glu Leu Asp Tyr Leu Thr Arg His Tyr Leu Val Lys Asn Lys Lys Leu
370                 375                 380

Tyr Glu Phe Asn Asn Ser Pro Tyr Glu Thr Gly Tyr Ile Lys Phe Ile
385                 390                 395                 400

Glu Asn Glu Asn Ser Phe Trp Tyr Asp Met Met Pro Ala Pro Gly Asp
                405                 410                 415

Lys Phe Asp Gln Ser Lys Tyr Leu Met Met Tyr Asn Asp Asn Lys Met
            420                 425                 430

Val Asp Ser Lys Asp Val Lys Ile Glu Val Tyr Leu Thr Thr Lys Lys
        435                 440                 445

```
Lys Gly Gly Gly Ser Gly Gly Gly Ser Gly Gly Gly Ser
    450             455             460

Glu Lys Ser Glu Glu Ile Asn Glu Lys Asp Leu Arg Lys Lys Ser Glu
465                 470                 475                 480

Leu Gln Gly Thr Ala Leu Gly Asn Leu Lys Gln Ile Tyr Tyr Tyr Asn
                485                 490                 495

Glu Lys Ala Lys Thr Glu Asn Lys Glu Ser His Asp Gln Phe Arg Gln
                500                 505                 510

His Thr Ile Leu Phe Lys Gly Phe Phe Thr Asp His Ser Trp Tyr Asn
            515                 520                 525

Asp Leu Leu Val Arg Phe Asp Ser Lys Asp Ile Val Asp Lys Tyr Lys
        530                 535                 540

Gly Lys Lys Val Asp Leu Tyr Gly Ala Tyr Ala Gly Tyr Gln Cys Ala
545                 550                 555                 560

Gly Gly Thr Pro Asn Lys Thr Ala Cys Met Tyr Gly Gly Val Thr Leu
                565                 570                 575

His Asp Asn Asn Arg Leu Thr Glu Glu Lys Lys Val Pro Ile Asn Leu
            580                 585                 590

Trp Leu Asp Gly Lys Gln Asn Thr Val Pro Leu Glu Thr Val Lys Thr
        595                 600                 605

Asn Lys Lys Asn Val Thr Val Gln Glu Leu Asp Leu Gln Ala Arg Arg
610                 615                 620

Tyr Leu Gln Glu Lys Tyr Asn Leu Tyr Asn Ser Asp Val Phe Asp Gly
                630                 635                 640
625

Lys Val Gln Arg Gly Leu Ile Val Phe His Thr Ser Thr Glu Pro Ser
                645                 650                 655

Val Asn Tyr Asp Leu Phe Gly Ala Gln Gly Gln Tyr Ser Asn Thr Leu
                660                 665                 670

Leu Arg Ile Tyr Arg Asp Asn Lys Thr Ile Asn Ser Glu Asn Met Ala
            675                 680                 685

Ile Asp Ile Tyr Leu Tyr Thr Ser
        690                 695

<210> SEQ ID NO 7
<211> LENGTH: 2115
<212> TYPE: DNA
<213> ORGANISM: Artificial Sequence
<220> FEATURE:
<223> OTHER INFORMATION: Synthetic

<400> SEQUENCE: 7
atgtcgacga atgacaacat caaagacctg ctggactggt actcctcggg ctcggatacg      60
ttcacgaata gcgaagtgct ggcaaactca cgcggtagca tgcgtatcaa aaataccgat     120
ggtagcatta gcctgatcgc ttttccgtca ccgtattaca gcccggcatt caccaaaggc     180
gaaaaagtgg atctgaatac caaacgcacg aaaaaaatca ccagcatacc tca gaaggtacc     240 tacatccact ttcagatcag cggcgtgacc aacaccgaaa aactgccgac cccgattgaa     300
ctgccgctga aagtgaaagt tcatggcaaa gattcgccgc tgaaatattg gccgaaattt     360
gataaaaaac agctggcaat ttcgaccctg gatttcgaaa ttcgccacca gctgacccag     420
atccatggtc tgtaccgttc aagcgacaaa accggcggtt attggaaaat caccatgaat     480
gatggttcga cgtaccagag cgatctgtcg aaaaaattcg aatacaacac ggaaaaaccg     540
ccgattaata tcgatgaaat caaaaccatc gaagcgaaaa tcaatggcgg tggcggctcg     600
ggtggtggcg gtagcggtgg cggcggtagt gaatcgcaac cggatccgaa accggacgaa     660
```

```
ctgcacaaat cgtccaaatt taccggtctg atggaaaata tgaaagtgct gtatgatgac        720
aaccatgtgt cggcaattaa cgtgaaaagc atcgatcagt tcgctatttt cgatctgatc        780
tatagcatta aagatacgaa actgggtaat tacgataacg ttcgtgtgga atttaaaaac        840
aaagatctgg cggacaaata taaagacaaa tacgtggacg ttttcggtgc gaatgcgtat        900
taccaatgcg cctttagcaa aaagaccaat gatatcaact cccatcagac cgacaaacgt        960
aaaacctgca tgtacggtgg tgtgaccgaa cataacggta atcagctgga caaatatcgt       1020
agcatcacgg tccgtgtgtt tgaagacggc aaaaacctgc tgtcatttga tgttcagacg       1080
aacaaaaaga aagttacggc tcaagaactg gattacctga cccgccacta tctggtgaaa       1140
aataaaaaac tgtacgaatt taacaatagc ccgtacgaaa ccggctacat caaattcatt       1200
gaaaatgaaa atagcttttg gtacgatatg atgccggcac cgggtgacaa atttgaccaa       1260
agcaaatacc tgatgatgta caacgataac aaaatggtcg attcaaaaga cgtgaaaatc       1320
gaagtctatc tgacgaccaa aaagaaaggt ggcggtggtt ctggtggtgg tggctcgggc       1380
ggcggtggct cggaaaaatc cgaagaaatt aacgaaaaag acctgcgtaa aaaatccgaa       1440
ctgcagggta cggcgctggg taatctgaaa cagatttatt actacaacga aaaagccaaa       1500
accgaaaaca agaaagccca tgatcagttc cgccagcata cgatcctgtt caaaggcttt       1560
ttcaccgatc attcgtggta taatgacctg ctggtgcgtt tcgatagcaa agacattgtg       1620
gataaatata aaggcaaaaa agtggatctg tatggcgcat acgctggtta tcagtgtgcg       1680
ggcggtacgc cgaataaaac ggcatgcatg tatggtggtg tgacgctgca tgacaataac       1740
cgcctgaccg aagaaaagaa agtgccgatt aatctgtggc tggacggtaa acagaacacc       1800
gtgccgctgg aaacggtgaa aaccaataaa agaacgtga ccgtgcagga actggacctg        1860
caagcacgcc gttatctgca ggaaaaatat aacctgtata cagcgacgt gttcgatggc        1920 aaagtgcagc gtggtctgat cgtcttccat accagcaccg aaccgagcgt taactatgac       1980
ctgtttggcg cacaaggcca gtactccaat accctgctgc gcatttatcg cgataacaaa       2040
accattaact ccgaaaacat gcacattgac atttacctgt acacctcgta acatcatcac       2100
catcattgat aataa                                                        2115
```

<210> SEQ ID NO 8
<211> LENGTH: 2115
<212> TYPE: DNA
<213> ORGANISM: Artificial Sequence
<220> FEATURE:
<223> OTHER INFORMATION: Synthetic

<400> SEQUENCE: 8

```
atgtcgacga atgacaacat caaagacctg ctggactggt actcctcggg ctcggatacg         60
ttcacgaata gcgaagtgct ggcaaactca cgcggtagca tgcgtatcaa aaataccgat        120
ggtagcatta gcctgatcgc ttttccgtca ccgtattaca gcccggcatt caccaaaggc        180
gaaaaagtgg atctgaatac caaacgcacg aaaaaatcac agcataccts agaaggtacc        240
tacatccact ttcagatcag cggcgtgacc aacaccgaaa aactgccgac cccgattgaa        300
ctgccgctga aagtgaaagt tcatggcaaa gattcgccgc tgaaatattg gccgaaattt        360
gataaaaaac agctggcaat ttcgaccctg gatttcgaaa ttcgccacca gctgacccag        420
atccatggtc tgtaccgttc aagcgacaaa accggcggtt attggaaaat caccatgaat       480
gatggttcga cgtaccagag cgatctgtcg aaaaaattcg aatacaacac ggaaaaaccg       540
```

-continued

```
ccgattaata tcgatgaaat caaaaccatc gaagcggaaa tcaatggcgg tggcggctcg      600
ggtggtggcg gtagcggtgg cggcggtagt gaatcgcaac cggatccgaa accggacgaa      660
ctgcacaaat cgtccaaatt taccggtctg atggaaaata tgaaagtgct gtatgatgac      720
aaccatgtgt cggcaattaa cgtgaaaagc atcgatcagt ttcgctattt cgatctgatc      780
tatagcatta aagatacgaa actgggtaat tacgataacg ttcgtgtgga atttaaaaac      840
aaagatctgg cggacaaata taaagacaaa tacgtggacg ttttcggtgc gaatgcgtat      900
taccaatgcg cctttagcaa aaagaccaat gatatcaact cccatcagac cgacaaacgt      960
aaaacctgca tgtacggtgg tgtgaccgaa cataacggta atcagctgga caaatatcgt     1020
agcatcacgg tccgtgtgtt tgaagacggc aaaaacctgc tgtcatttga tgttcagacg     1080
aacaaaaaga agttacggc tcaagaactg gattacctga cccgccacta tctggtgaaa      1140
aataaaaaac tgtacgaatt taacaatagc ccgtacgaaa ccggctacat caaattcatt     1200
gaaaatgaaa atagcttttg gtacgatatg atgccggcac cgggtgacaa atttgaccaa     1260
agcaaatacc tgatgatgta caacgataac aaaatggtcg attcaaaaga cgtgaaaatc     1320
gaagtctatc tgacgaccaa aaagaaaggt ggcggtggtt ctggtggtgg tggctcgggc     1380
ggcggtggct cggaaaaatc cgaagaaatt aacgaaaaag acctgcgtaa aaaatccgaa     1440
ctgcagggta cggcgctggg taatctgaaa cagatttatt actacaacga aaaagccaaa     1500
accgaaaaca aagaaagcca tgatcagttc cgccagcata cgatcctgtt caaaggcttt     1560
ttcaccgatc attcgtggta taatgacctg ctggtgcgtt tcgatagcaa agacattgtg     1620
gataaatata aaggcaaaaa agtggatctg tatggcgcat acgctggtta tcagtgtgcg     1680
ggcggtacgc cgaataaaac ggcatgcatg tatggtggtg tgacgctgca tgacaataac     1740
cgcctgaccg aagaaaagaa agtgccgatt aatctgtggc tggacggtaa acagaacacc     1800
gtgccgctgg aaacggtgaa aaccaataaa agaacgtga ccgtgcagga actggacctg      1860
caagcacgcc gttatctgca ggaaaaatat aacctgtata cagcgacgt gttcgatggc      1920 aaagtgcagc gtggtctgat cgtcttccat accagcaccg aaccgagcgt taactatgac     1980
ctgtttggcg cacaaggcca gtactccaat accctgctgc gcatttatcg cgataacaaa     2040
accattaact ccgaaaacat ggccattgac atttacctgt acacctcgta acatcatcac     2100
catcattgat aataa                                                      2115
```

<210> SEQ ID NO 9
<211> LENGTH: 195
<212> TYPE: PRT
<213> ORGANISM: Staphylococcus aureus

<400> SEQUENCE: 9

```
Met Ser Thr Asn Asp Asn Ile Lys Asp Leu Leu Asp Trp Tyr Ser Ser
1               5                   10                  15

Gly Ser Asp Thr Phe Thr Asn Ser Glu Val Leu Asp Asn Ser Leu Gly
            20                  25                  30

Ser Met Arg Ile Lys Asn Thr Asp Gly Ser Ile Ser Leu Ile Ile Phe
        35                  40                  45

Pro Ser Pro Tyr Tyr Ser Pro Ala Phe Thr Lys Gly Glu Lys Val Asp
    50                  55                  60

Leu Asn Thr Lys Arg Thr Lys Lys Ser Gln His Thr Ser Glu Gly Thr
65                  70                  75                  80

Tyr Ile His Phe Gln Ile Ser Gly Val Thr Asn Thr Glu Lys Leu Pro
                85                  90                  95
```

-continued

Thr Pro Ile Glu Leu Pro Leu Lys Val Lys Val His Gly Lys Asp Ser
                100                 105                 110

Pro Leu Lys Tyr Trp Pro Lys Phe Asp Lys Lys Gln Leu Ala Ile Ser
            115                 120                 125

Thr Leu Asp Phe Glu Ile Arg His Gln Leu Thr Gln Ile His Gly Leu
        130                 135                 140

Tyr Arg Ser Ser Asp Lys Thr Gly Gly Tyr Trp Lys Ile Thr Met Asn
145                 150                 155                 160

Asp Gly Ser Thr Tyr Gln Ser Asp Leu Ser Lys Lys Phe Glu Tyr Asn
                165                 170                 175

Thr Glu Lys Pro Pro Ile Asn Ile Asp Glu Ile Lys Thr Ile Glu Ala
            180                 185                 190

Glu Ile Asn
        195

<210> SEQ ID NO 10
<211> LENGTH: 240
<212> TYPE: PRT
<213> ORGANISM: Staphylococcus aureus

<400> SEQUENCE: 10

Met Glu Ser Gln Pro Asp Pro Lys Pro Asp Glu Leu His Lys Ser Ser
1               5                   10                  15

Lys Phe Thr Gly Leu Met Glu Asn Met Lys Val Leu Tyr Asp Asp Asn
                20                  25                  30

His Val Ser Ala Ile Asn Val Lys Ser Ile Asp Gln Phe Leu Tyr Phe
            35                  40                  45

Asp Leu Ile Tyr Ser Ile Lys Asp Thr Lys Leu Gly Asn Tyr Asp Asn
        50                  55                  60

Val Arg Val Glu Phe Lys Asn Lys Asp Leu Ala Asp Lys Tyr Lys Asp
65                  70                  75                  80

Lys Tyr Val Asp Val Phe Gly Ala Asn Tyr Tyr Gln Cys Tyr Phe
                85                  90                  95

Ser Lys Lys Thr Asn Asp Ile Asn Ser His Gln Thr Asp Lys Arg Lys
                100                 105                 110

Thr Cys Met Tyr Gly Gly Val Thr Glu His Asn Gly Asn Gln Leu Asp
            115                 120                 125

Lys Tyr Arg Ser Ile Thr Val Arg Val Phe Glu Asp Gly Lys Asn Leu
        130                 135                 140

Leu Ser Phe Asp Val Gln Thr Asn Lys Lys Lys Val Thr Ala Gln Glu
145                 150                 155                 160

Leu Asp Tyr Leu Thr Arg His Tyr Leu Val Lys Asn Lys Lys Leu Tyr
                165                 170                 175

Glu Phe Asn Asn Ser Pro Tyr Glu Thr Gly Tyr Ile Lys Phe Ile Glu
            180                 185                 190

Asn Glu Asn Ser Phe Trp Tyr Asp Met Met Pro Ala Pro Gly Asp Lys
        195                 200                 205

Phe Asp Gln Ser Lys Tyr Leu Met Met Tyr Asn Asp Asn Lys Met Val
    210                 215                 220

Asp Ser Lys Asp Val Lys Ile Glu Val Tyr Leu Thr Thr Lys Lys Lys
225                 230                 235                 240

<210> SEQ ID NO 11
<211> LENGTH: 232
<212> TYPE: PRT

<213> ORGANISM: Staphylococcus aureus
<220> FEATURE:
<221> NAME/KEY: SIMILAR
<222> LOCATION: (1)..(232)
<223> OTHER INFORMATION: SEA H225A

<400> SEQUENCE: 11

```
Glu Lys Ser Glu Glu Ile Asn Glu Lys Asp Leu Arg Lys Lys Ser Glu
1               5                   10                  15

Leu Gln Gly Thr Ala Leu Gly Asn Leu Lys Gln Ile Tyr Tyr Tyr Asn
            20                  25                  30

Glu Lys Ala Lys Thr Glu Asn Lys Glu Ser His Asp Gln Phe Leu Gln
        35                  40                  45

His Thr Ile Leu Phe Lys Gly Phe Phe Thr Asp His Ser Trp Tyr Asn
    50                  55                  60

Asp Leu Leu Val Asp Phe Asp Ser Lys Asp Ile Val Asp Lys Tyr Lys
65                  70                  75                  80

Gly Lys Lys Val Asp Leu Tyr Gly Ala Tyr Tyr Gly Tyr Gln Cys Ala
                85                  90                  95

Gly Gly Thr Pro Asn Lys Thr Ala Cys Met Tyr Gly Gly Val Thr Leu
            100                 105                 110

His Asp Asn Asn Arg Leu Thr Glu Glu Lys Lys Val Pro Ile Asn Leu
        115                 120                 125

Trp Leu Asp Gly Lys Gln Asn Thr Val Pro Leu Glu Thr Val Lys Thr
130                 135                 140

Asn Lys Lys Asn Val Thr Val Gln Glu Leu Asp Leu Gln Ala Arg Arg
145                 150                 155                 160

Tyr Leu Gln Glu Lys Tyr Asn Leu Tyr Asn Ser Asp Val Phe Asp Gly
                165                 170                 175

Lys Val Gln Arg Gly Leu Ile Val Phe His Thr Ser Thr Glu Pro Ser
            180                 185                 190

Val Asn Tyr Asp Leu Phe Gly Ala Gln Gly Gln Tyr Ser Asn Thr Leu
        195                 200                 205

Leu Arg Ile Tyr Arg Asp Asn Lys Thr Ile Asn Ser Glu Asn Met Ala
210                 215                 220

Ile Asp Ile Tyr Leu Tyr Thr Ser
225                 230
```

<210> SEQ ID NO 12
<211> LENGTH: 232
<212> TYPE: PRT
<213> ORGANISM: Staphylococcus aureus

<400> SEQUENCE: 12

```
Glu Lys Ser Glu Glu Ile Asn Glu Lys Asp Leu Arg Lys Lys Ser Glu
1               5                   10                  15

Leu Gln Gly Thr Ala Leu Gly Asn Leu Lys Gln Ile Tyr Tyr Tyr Asn
            20                  25                  30

Glu Lys Ala Lys Thr Glu Asn Lys Glu Ser His Asp Gln Phe Leu Gln
        35                  40                  45

His Thr Ile Leu Phe Lys Gly Phe Phe Thr Asp His Ser Trp Tyr Asn
    50                  55                  60

Asp Leu Leu Val Asp Phe Asp Ser Lys Asp Ile Val Asp Lys Tyr Lys
65                  70                  75                  80

Gly Lys Lys Val Asp Leu Tyr Gly Ala Tyr Tyr Gly Tyr Gln Cys Ala
                85                  90                  95
```

```
Gly Gly Thr Pro Asn Lys Thr Ala Cys Met Tyr Gly Gly Val Thr Leu
            100                 105                 110

His Asp Asn Asn Arg Leu Thr Glu Glu Lys Lys Val Pro Ile Asn Leu
        115                 120                 125

Trp Leu Asp Gly Lys Gln Asn Thr Val Pro Leu Glu Thr Val Lys Thr
        130                 135                 140

Asn Lys Lys Asn Val Thr Val Gln Glu Leu Asp Leu Gln Ala Arg Arg
145                 150                 155                 160

Tyr Leu Gln Glu Lys Tyr Asn Leu Tyr Asn Ser Asp Val Phe Asp Gly
                165                 170                 175

Lys Val Gln Arg Gly Leu Ile Val Phe His Thr Ser Thr Glu Pro Ser
                180                 185                 190

Val Asn Tyr Asp Leu Phe Gly Ala Gln Gly Gln Tyr Ser Asn Thr Leu
        195                 200                 205

Leu Arg Ile Tyr Arg Asp Asn Lys Thr Ile Asn Ser Glu Asn Met His
        210                 215                 220

Ile Asp Ile Tyr Leu Tyr Thr Ser
225                 230

<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Gly Gly Gly Ser
1

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Gly Gly Gly Gly Ser
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Gly Gly Gly Gly Ser Gly Gly Gly Gly Ser Gly Gly Gly Gly Ser
1               5                   10                  15
```